US012782355B2

(12) United States Patent
Shanmugam et al.

(10) Patent No.: US 12,782,355 B2
(45) Date of Patent: Nov. 3, 2026

(54) METHODS AND SYSTEMS FOR EVALUATION OF IMMUNE CELL INFILTRATE IN STAGE IV COLORECTAL CANCER

(71) Applicants: Ventana Medical Systems, Inc., Tucson, AZ (US); Mayo Foundation for Medical Education and Research, Rochester, MN (US)

(72) Inventors: Kandavel Shanmugam, Tucson, AZ (US); Frank A. Sinicrope, Rochester, MN (US)

(73) Assignees: Ventana Medical Systems, Inc., Tucson, AZ (US); Mayo Foundation for Medical Education and Research, Rochester, MN (US)

( * ) Notice: Subject to any disclaimer, the term of this patent is extended or adjusted under 35 U.S.C. 154(b) by 1205 days.

(21) Appl. No.: 17/389,910

(22) Filed: Jul. 30, 2021

(65) Prior Publication Data

US 2021/0373024 A1 Dec. 2, 2021

Related U.S. Application Data

(63) Continuation of application No. PCT/EP2020/052737, filed on Feb. 4, 2020.

(60) Provisional application No. 62/801,482, filed on Feb. 5, 2019.

(51) Int. Cl.
*G01N 33/57535* (2026.01)

(52) U.S. Cl.
CPC .................. *G01N 33/57535* (2026.01); *G01N 2333/70517* (2013.01)

(58) Field of Classification Search
CPC ... G01N 33/57419; G01N 2333/70517; G01N 2333/7051; G01N 2800/52; G01N 33/57535
See application file for complete search history.

(56) References Cited

U.S. PATENT DOCUMENTS

| | | | |
|---|---|---|---|
| 8,481,271 | B2 | 7/2013 | Galon |
| 9,298,968 | B1 | 3/2016 | Peljto |
| 11,079,382 | B2 | 8/2021 | Sebastiao |
| 2013/0164762 | A1 | 6/2013 | Emile et al. |
| 2013/0310267 | A1 | 11/2013 | HistoRx |
| 2015/0153349 | A1 | 6/2015 | Galon et al. |
| 2020/0234442 | A1 | 7/2020 | Barnes et al. |
| 2020/0355688 | A1 | 11/2020 | Shanmugam et al. |
| 2021/0311060 | A1 | 10/2021 | Barnes et al. |

FOREIGN PATENT DOCUMENTS

| | | | |
|---|---|---|---|
| CN | 106999582 | A | 8/2017 |
| EP | 1777523 | A1 | 4/2007 |
| WO | 2013186374 | A1 | 12/2013 |
| WO | 2015121465 | A1 | 8/2015 |
| WO | 2015124737 | A1 | 8/2015 |
| WO | 2015164501 | A2 | 10/2015 |
| WO | 2016/077553 | A1 | 5/2016 |
| WO | 2017/103086 | A1 | 6/2017 |
| WO | 2017151755 | A1 | 9/2017 |
| WO | 2017194556 | A1 | 11/2017 |
| WO | 2019020556 | A1 | 1/2019 |

OTHER PUBLICATIONS

Kwak, Yoonjin, et al. "Immunoscore encompassing CD3+ and CDS+ T cell densities in distant metastasis is a robust prognostic marker for advanced colorectal cancer". Oncotarget, Jan. 1, 2016, pp. 81778-81790. (Year: 2016).*

Kikuchi, Tomohiro, et al. "A subset of patients with MSS/MSI-low-colorectal cancer showed increased CD8(+) TILs together with up-regulated IFN-γ", 2019, Oncology Letters, 18:5977-5985. (Year: 2019).*

Narayanan, Sumana, et al., "Tumor Infiltrating Lymphocytes and Macrophages Improve Survival in Microsatellite Unstable Colorectal Cancer" 2019, Scientific Reports, 9:13455. (Year: 2019).*

Tumeh, P. C., "PD-1 blockade induces responses by inhibiting adaptive immune resistance", 2014, Nature, 515: 568-571. (Year: 2014).*

Pages, Franck et al., "International validation of the consensus Immunoscore for the classification of colon cancer: a prognostic and accuracy study", The Lancet, 2018, 391:10135, pp. 2128-2139,. (Year: 2018).*

Overman MJ, et al. "Nivolumab in patients with metastatic DNA mismatch repair deficient or microsatellite instability high colorectal cancer (CheckMate 142): An open label, multicentre, phase 2 study." 2017, Lancet Oncol 18: 1182-1191. (Year: 2017).*

Galon, J. et al., "Type, density, and location of immune cells within human colorectal tumors predict clinical outcome", 2006, Science, 313(5795):1960-4. (Year: 2006).*

Basile et al. Immunotherapy for colorectal cancer: where are we heading? Expert Opin Biol Ther. Jun. 2017;17(6):709-721. (Year: 2017).*

(Continued)

*Primary Examiner* — Gary B Nickol
*Assistant Examiner* — Amber K Faust
(74) *Attorney, Agent, or Firm* — Charney IP Law LLC; Thomas M. Finetti

(57) ABSTRACT

Immune context scores are calculated for stage IV colorectal tumor tissue samples using non-continuous scoring functions. Feature metrics for at least one immune cell marker are calculated for a region or regions of interest, the feature metrics including at least a density of human CD8+ cells in a region of interest including a tumor core to generate an immune context score. The immune context score can then be used as a predictive metric (e.g. likelihood of response to a particular treatment course). The immune context score may then be incorporated into diagnostic and/or treatment decisions.

12 Claims, 5 Drawing Sheets

Specification includes a Sequence Listing.

(56) References Cited

OTHER PUBLICATIONS

Kareva I. A Combination of Immune Checkpoint Inhibition with Metronomic Chemotherapy as a Way of Targeting Therapy-Resistant Cancer Cells. Int J Mol Sci. Oct. 13, 2017;18(10):2134. (Year: 2017).*
Galon, J. et al. MSI status plus immunoscore to select metastatic colorectal cancer patients for immunotherapies. 2018. Annals of Oncology, vol. 29, x4. (Year: 2018).*
Schönmeyer R, Schape A, Schmidt G. Image-based data mining. In Tissue Phenomics—Profiling Cancer Patients for Treatment Decisions, G Binnig, R Huss, G Schmidt (eds). Pan Stanford Publishing Pte. Ltd: Singapore, 2018; 101-130. (Year: 2018).*
Lorsakul, Auranuch et al., "Validation of Multiplex Immunohistochemistry Assays using Automated Image Analysis", Proc. SPIE 10581, Medical Imaging 2018: Digital Pathology, Mar. 6, 2018, 105810J.
Anitei et al., Prognostic and Predictive Values of the Immunoscore in Patients with Rectal Cancer, Clinical Cancer Research, Apr. 1, 2014, pp. 1891-1899, vol. 20, Issue 7.
Chen et al., Automatic Lymphocyte Detection in H&E Images with Deep Neural Networks, Dec. 9, 2016, arXiv:1612.03217v1, https://arxiv.org/abs/1612.03217.
Forrest et al., Comparison of visual and automated assessment of tumour inflammatory infiltrates in patients with colorectal cancer, European Journal of Cancer, Dec. 16, 2013, pp. 544-552, vol. 50, Issue 3.
Galon et al., Towards the introduction of the 'Immunoscore' in the classification of malignant tumours, Journal of Pathology, Dec. 10, 2013, pp. 199-209, vol. 232, Issue 2.
Galon et al., Validation of the Immunoscore (IM) as a prognostic marker in stage I/II/III colon cancer: Results of a worldwide consortium-based analysis of 1,336 patients., Journal of Clinical Oncology, May 20, 2016, vol. 34, suppl. Abstract No. 3500.
Galon et al., Validation of the Immunoscore (IM) as a prognostic marker in stage I/II/III colon cancer: Results of a worldwide consortium-based analysis of 1,336 patients., American Society of Clinical Oncology, Jun. 5, 2016, Powerpoint presentation, http://meetinglibrary.asco.org/content/123627?media=sl.
Jass, Lymphocytic infiltration and survival in rectal cancer, Journal of Clinical Pathology, Jun. 1, 1986, pp. 585-589, vol. 39, Issue 6.
Jass et al., A new prognostic classification of rectal cancer, The Lancet, pp. 1303-1306, Jun. 6, 1987, vol. 329, Issue 8545.
Mei et al., Tumour-infiltrating inflammation and prognosis in colorectal cancer: systematic review and meta-analysis, British Journal of Cancer, Feb. 6, 2014, pp. 11595-1605 , vol. 110.
Pages et al., Immune infiltration in human tumors: a prognostic factor that should not be ignored, Oncogene, Nov. 30, 2009, pp. 1093-1102, vol. 29.
Zou et al., PD-L1 (B7-H1) and PD-1 pathway blockade for cancer therapy: Mechanisms, response biomarkers, and combinations, Science Translation Medicine, Mar. 2, 2016, pp. 328rv324, vol. 8, Issue 328.
Llosa et al., The vigorous immune microenvironment of microsatellite instable colon cancer is balanced by multiple counter-inhibitory checkpoints, Cancer discovery, Jan. 1, 2015, pp. 43-51, vol. 5, Issue 1.
Le et al., Mismatch repair deficiency predicts response of solid tumors to PD-1 blockade, Science, Jul. 28, 2017, pp. 40-413, vol. 357, Issue 6349.
Pages et al., International validation of the consensus Immunoscore for the classification of colon cancer: a prognostic and accuracy study, The Lancet, May 10, 2018, pp. 2128-2139, vol. 391, Issue 10135.
Yoon et al., Inter-tumoral heterogeneity of CD3(+) and CD8(+) T-cell densities in the microenvironment of DNA mismatch repair-deficient colon cancers: implications for prognosis, Clinical Cancer Research, Oct. 9, 2018, pp. 125-133, vol. 25, Issue 1.
Eisenhauer et al., New response evaluation criteria in solid tumours: revised RECIST guideline (version 1.1), European Journal of Cancer, Dec. 22, 2008, pp. 228-247, vol. 45, Issue 2.
Sinicrope et al., Prognostic impact of deficient DNA mismatch repair in patients with stage III colon cancer from a randomized trial of FOLFOX-based adjuvant chemotherapy, Journal of Clinical Oncology, Oct. 10, 2013, pp. 3664-3672, vol. 31, Issue 29.
El Jabbour et al., PD-L1 protein expression in tumour cells and immune cells in mismatch repair protein-deficient and -proficient colorectal cancer: the foundation study using the SP142 antibody and whole section immunohistochemistry, Journal of Clinical Pathology, Jun. 30, 2018, pp. 46-51, vol. 71, Issue 1.
Sarkar et al., A robust method for inter-marker whole slide registration of digital pathology images using lines based features, IEEE 11th International Symposium on Biomedical Imaging (ISBI), Jul. 31, 2014, pp. 762-765.
Kwak et al., Immunoscore encompassing CD3+ and CD8+ T cell densities in distant metastasis is a robust prognostic marker for advanced colorectal cancer, Oncotarget, Nov. 8, 2016, pp. 81778-81790, vol. 7, No. 49.
Lee et al., Clinical impact of tumor-infiltrating lymphocytes for survival in curatively resected stage IV colon cancer with isolated liver or lung metastasis, Annals of Surgical Oncology, Dec. 6, 2021, pp. 697-702, vol. 20.
International Search Report for International Patent Application No. PCT/EP2020/052737 dated Apr. 30, 2020.
Anitei Clin Cancer Res 2014 20 7 1891-1899 including Supp Data Tables 1-5.
Donnem Ann Oncol 2016 27 225 232.
Hermitte J Immunother Cancer 2016 4 57 Supp abstract.
Int'l Search Report and WO P34640 (PCT/EP2019/052373) mailed on Jun. 17, 2019.
Int'l Search Report and WO P34353 (PCT/EP2020/069896) mailed on Sep. 28, 2020.
Obeid Cancer Immunol Immunother 2017 6 33 43.
Venook J Clin Oncol 2016 34 15 Supp Abstr 3504 1-24.
Ward-Hartstonge Cancer Immunol Immunother 2017 66 4 515-522.
Wen Cancer Immunol Res 2017 5 7 524 534.
Eisenhauer, E. A. et al., New response evaluation criteria in solid tumours: Revised RECIST guideline (version 1.1), European Journal of Cancer, 2009, pp. 228-247, vol. 45.
El Jabbour, Tony et al., PD-L1 protein expression in tumour cells and immune cells in mismatch repair protein-deficient and -proficient colorectal cancer: the foundation study using the SP142 antibody and whole section immunohistochemistry, J Clin Pathol 2018 71 46 51.
Galon, Jerome et al., Type, density, and location of immune cells within human colorectal tumors predict clinical outcome, Science, vol. 313, pp. 1960-1964, 2006.
Kikuchi, Tomohiro, et al. A subset of patients with MSS/MSI-low-colorectal cancer showed increased CD8(+) TILs together with up-regulated IFN-γ, 2019, Oncology Letters, 18:5977-5985.
Llosa, N. J. et al., The vigorous immune microenvironment of microsatellite instable colon cancer is balanced by multiple counter-inhibitory checkpoints, Cancer Discovery, Jan. 1, 2015, pp. 43-51, vol. 5, No. 1.
Narayanan, Sumana, et al., Tumor Infiltrating Lymphocytes and Macrophages Improve Survival in Microsatellite Unstable Colorectal Cancer, Nature Research, vol. 9, Article 13455, 10 pp., 2019.
Overman, Michael J. et al., Nivolumab in patients with metastatic DNA mismatch repair deficient or microsatellite instability high colorectal cancer (CheckMate 142): An open label, multicentre, phase 2 study, The Lancet Oncology, vol. 18, pp. 1182-1191, Sep. 2, 2017.
Pages, Franck et al., International validation of the consensus Immunoscore for the classification of colon cancer: a prognostic and accuracy study, The Lancet, vol. 391, No. 10135, pp. 2128-2139, 2018.
Sinicrope, Frank A. et al., Prognostic Impact of Deficient DNA Mismatch Repair in Patients With Stage III Colon Cancer From a Randomized Trial of FOLFOX-Based Adjuvant Chemotherapy, Journal of Clinical Oncology, vol. 31, No. 29, pp. 3664-3672, 2013.
Tumeh et al, 2014, "PD-1 blockade induces responses by inhibiting adaptive immune resistance", Nature, 515 (7528):568-571.

(56) References Cited

OTHER PUBLICATIONS

Zou, Weiping et al., PD-L1 (B7-H1) and PD-1 Pathway Blockade for Cancer Therapy: Mechanisms, Response Biomarkers and Combinations, Science Translational Medicine, vol. 8, No. 328, Article 328rv4, 34 pp., 2016.

* cited by examiner

METHODS AND SYSTEMS FOR EVALUATION OF IMMUNE CELL INFILTRATE IN STAGE IV COLORECTAL CANCER

CROSS-REFERENCE TO RELATED APPLICATIONS

This is a bypass continuation of International Application No. PCT/EP2020/052737, filed Feb. 4, 2020, which claims the benefit of U.S. Provisional Patent Application No. 62/801,482, filed Feb. 5, 2019, the content of each of which is incorporated herein by reference in its entirety.

REFERENCE TO SEQUENCE LISTING SUBMITTED AS A COMPLIANT ASCII TEXT FILE (.TXT)

Pursuant to the EFS-Web legal framework and 37 C.F.R. § 1.821-825 (see M.P.E.P. § 2442.03(a)), a Sequence Listing in the form of an ASCII-compliant text file (entitled "Sequence_Listing_3000022-005001_ST25.txt" created on 22 Jul. 2021, and 56,810 bytes in size) is submitted concurrently with the instant application, and the entire contents of the Sequence Listing are incorporated herein by reference.

BACKGROUND OF THE INVENTION

Field of the Invention

The invention relates to detection, characterization and enumeration of discrete populations of immune cells in tumor samples for use in prognosing and treating proliferative diseases, such as colorectal cancers.

Description of Related Art

The presence or absence of an inflammatory response is known to be a prognostic factor in a number of different cancer types, including colorectal cancer, melanoma, breast cancer, ovarian cancer, non-Hodgkin's lymphoma, head and neck cancer, non-small-cell lung cancer (NSCLC), esophageal cancer, and urothelial carcinoma, among others. See Pagès et al. (2010). In colorectal cancer, for example, the relative amount of immune cell infiltrate has been considered an independent prognostic factor for colorectal cancers since at least 1986. See Jass (1986).

Programmed death ligand 1 (PD-L1) is an immune checkpoint protein that regulates the immune system through binding of the programmed cell death protein 1 (PD-1) receptor. PD-L1 is expressed on multiple immune cell types and is also expressed in many cancer cell types, including colorectal cancer (CRC) cells. PD-L1 can bind to PD-1 receptors on activated T cells, which leads to the inhibition of the cytotoxic T cells and enables immune evasion of cancer. See Zou et al (2016). Antibodies against immune checkpoint proteins PD-1/PD-L1 can reactivate cytotoxic T-cells to attack cancer cells and have revolutionized the treatment of solid tumors. CRCs with deficient DNA mismatch repair (dMMR) have microsatellite instability (MSI) that results in hypermutation and expression of mutation-specific neopeptides. See Llosa et al. (2015). Treatment of metastatic CRCs with the anti-PD-1 antibody, pembrolizumab, produced frequent and durable responses in these patients which led to its approval by the U.S. Food and Drug Administration for this tumor subgroup after progression following treatment with a fluoropyrimidine, oxaliplatin, and irinotecan. However, more than half of dMMR mCRC patients display resistance to PD-1 blockade due to mechanisms that remain unknown. See Le et al. (2017). To date, there is no biomarker that has yet been identified to predict response to PD-1 blockade within dMMR tumors.

BRIEF SUMMARY OF THE INVENTION

This disclosure relates generally to the assessment of immune cells in stage IV colorectal tumors including, for example, T-lymphocytes (immune cells positive for the CD3 biomarker and the CD8 biomarker), using a scoring function to calculate an immune context score (ICS) for a sample of the tumor.

In an embodiment, one or more types of immune cells are detected morphologically (such as in an image of a sample stained with hematoxylin and eosin) and/or on the basis of cells expression of one or more immune cell markers. In an exemplary embodiment immune context score is used to predict the outcome of treatment of a deficient DNA mismatch repair (dMMR) stage IV colorectal cancer with an immune checkpoint-directed therapy.

In various embodiments, the method comprises obtaining an immune context score (ICS) from a tissue sample collected from a stage IV colorectal tumor: identifying a tumor core (CT) region of interest (ROI) in the tissue sample; detecting $CD8^+$ cells in at least a portion of the ROI; and obtaining a $CD8^+$ cell density within the ROI to calculate the ICS; and then selecting a treatment for the subject based upon the ICS. The method further comprises selecting a treatment comprising a full course of adjuvant chemotherapy and optionally a checkpoint inhibitor-directed therapy if the CD8+ cell density is low and a treatment comprising a checkpoint inhibitor-directed therapy and optionally a reduced course of an adjuvant chemotherapy if the CD8+ cell density is high.

In another embodiment, a computer-implemented method is provided comprising causing a computer processor to execute a set of computer-executable functions stored on a memory, the set of computer-executable functions comprising: (A) obtaining a digital image of a tissue section of a stage IV colorectal tumor, wherein the tissue section is histochemically stained for at least human CD8; (B) annotating one or more regions of interest (ROI) in the digital image, the ROI comprising a tumor core (CT); and (C) applying a scoring function to the ROI, wherein the scoring function comprises calculating a feature vector comprising a density of CD8+ cells in the CT to obtain an immune context score for the tissue section. In some embodiments, the CD8+ density is obtained as a total metric. In other embodiments, the CD8+ density is obtained as a mean or median of a plurality of control regions of the ROI. In some embodiments, the CD8+ density is normalized by applying a normalization factor to the CD8+ density, the normalization factor being equal to a pre-determined upper limit or lower limit of the feature metric. In an embodiment, the normalization factor is obtained by evaluating a distribution of CD8+ densities across a representative population of samples, identifying a skew in the distribution of feature metric values, and identifying a value at which a pre-determined number of samples fall beyond, wherein the value is selected as the normalization factor.

In another specific embodiment, a method is provided comprising: (a) annotating a one or more region(s) of interest (ROI) on a digital image of a tumor tissue section, wherein at least one of the ROIs includes at least a portion of a CT region; (b) detecting and quantitating cells expressing human CD8 in the ROI; (c) calculating a density of CD8+ cells within the ROI, and optionally normalizing the CD8+ cell density or tumor-infiltrating lymphocyte (TIL) cell density to the feature vector to obtain an immune context score (ICS) for the tumor. In an embodiment, the densities are area cell densities or linear cell densities.

Also provided herein are systems for scoring an immune context of a tumor tissue sample, the systems including at least a computer processor and a memory, wherein the memory stores a set of computer executable instructions to be executed by the computer processor, the set of computer executable instructions including any of the processes and methods described herein. In some embodiments, the systems include automated slide stainers for histochemically labelling sections of the tumor tissue sample, and/or means for generating digital images of the histochemically stained sections, such as microscopes operably linked to digital cameras or scanner systems. In further embodiments, the systems may further include a laboratory information system (LIS) for tracking and/or controlling processes to be performed on the samples, sections, and digital images.

DETAILED DESCRIPTION OF THE INVENTION

I. Definitions

Figure 1:
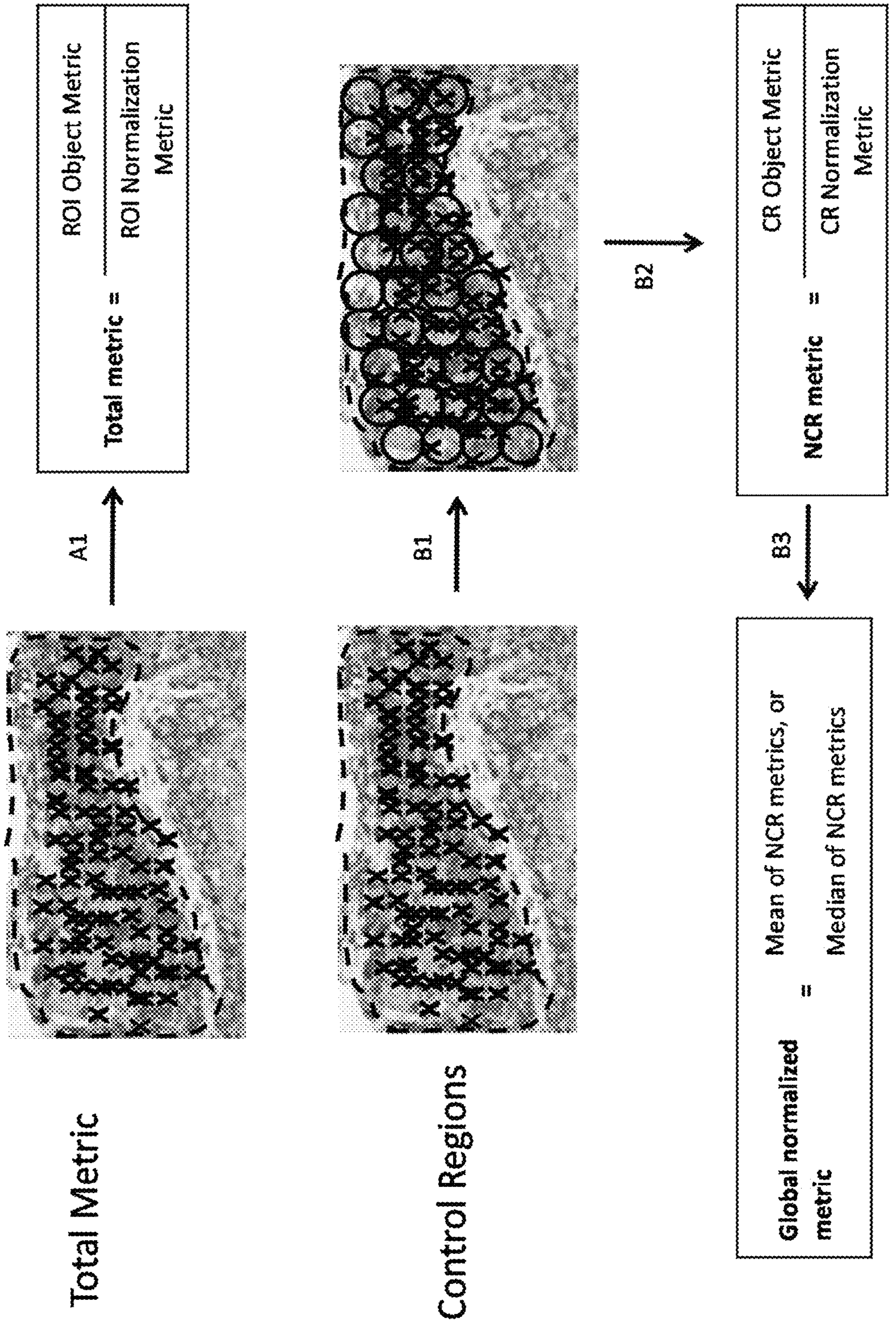
FIG. 1 illustrates two different methods of calculating feature metrics for ROIs. Dashed line in the images illustrates the boundary of an ROI. "X"s in the image indicate objects of interest marked in the image. Circles in the image are control regions that may be used to calculate global metrics for the control region.

Unless defined otherwise, technical and scientific terms used herein have the same meaning as commonly understood by a person of ordinary skill in the art. See, e.g., Lackie, DICTIONARY OF CELL AND MOLECULAR BIOLOGY, Elsevier (4th ed. 2007); Sambrook et al., MOLECULAR CLONING, A LABORATORY MANUAL, Cold Springs Harbor Press (Cold Springs Harbor, N.Y. 1989). The term "a" or "an" is intended to mean "one or more." The terms "comprise," "comprises," and "comprising," when preceding the recitation of a step or an element, are intended to mean that the addition of further steps or elements is optional and not excluded.

Antibody: The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

Antibody fragment: An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')2; diabodies; linear antibodies; single-chain antibody molecules (e.g. scFv); and multispecific antibodies formed from antibody fragments.

Biomarker: As used herein, the term "biomarker" shall refer to any molecule or group of molecules found in a biological sample that can be used to characterize the biological sample or a subject from which the biological sample is obtained. For example, a biomarker may be a molecule or group of molecules whose presence, absence, or relative abundance is:

- characteristic of a particular cell or tissue type or state;
- characteristic of a particular pathological condition or state; or
- indicative of the severity of a pathological condition, the likelihood of progression or regression of the pathological condition, and/or the likelihood that the pathological condition will respond to a particular treatment.

As another example, the biomarker may be a cell type or a microorganism (such as a bacteria, mycobacteria, fungi, viruses, and the like), or a substituent molecule or group of molecules thereof.

Biomarker-specific reagent: A specific detection reagent that is capable of specifically binding directly to one or more biomarkers in the cellular sample, such as a primary antibody.

Cellular sample: As used herein, the term "cellular sample" refers to any sample containing intact cells, such as cell cultures, bodily fluid samples or surgical specimens taken for pathological, histological, or cytological interpretation.

Continuous scoring function: A "continuous scoring function" is a mathematical formula into which the actual magnitude for one or more variables is input (optionally subject to upper and/or lower limits on the value and/or application of a normalization factor). In some examples, the value input into the continuous scoring function is the actual magnitude of the variable. In other examples, the value input into the continuous scoring function is the absolute value of the variable up to (and/or down to, as appropriate) a predetermined cutoff, wherein all absolute values beyond the cutoff value are assigned the cutoff value. In other examples, the value input into the continuous scoring function is a normalized value of the variable.

Complete response (CR): As used herein, a "complete response" refers to the disappearance of all target lesions in a subject following a particular therapy.

Cox proportional hazard model: A model of formula 1:

$$\frac{h(t)}{h_0(t)} = \exp(b_1 X_1 + b_2 X_2 + \ldots b_p X_p) \quad \text{Formula 1}$$

wherein $$\frac{h(t)}{h_0(t)}$$

is the ratio between the expected hazard at time t (h(t)) and a baseline hazard ($h_0(t)$, and $b_1$, $b_2$ . . . $b_p$ are constants extrapolated for each of the independent variables. As used throughout, the ratio $$\text{"}\frac{h(t)}{h_0(t)}\text{"}$$

will be referred to as the "Cox immune context score" or "$ICS_{cox}$."

Detection reagent: A "detection reagent" is any reagent that is used to deposit a stain in proximity to a biomarker-specific reagent in a cellular sample. Non-limiting examples include biomarker-specific reagents (such as primary antibodies), secondary detection reagents (such as secondary antibodies capable of binding to a primary antibody), tertiary detection reagents (such as tertiary antibodies capable of binding to secondary antibodies), enzymes directly or indirectly associated with the biomarker specific reagent, chemicals reactive with such enzymes to effect deposition of a fluorescent or chromogenic stain, wash reagents used between staining steps, and the like.

Detectable moiety: A molecule or material that can produce a detectable signal (such as visually, electronically or otherwise) that indicates the presence (i.e. qualitative analysis) and/or concentration (i.e. quantitative analysis) of the detectable moiety deposited on a sample. A detectable signal can be generated by any known or yet to be discovered mechanism including absorption, emission and/or scattering of a photon (including radio frequency, microwave frequency, infrared frequency, visible frequency and ultra-violet frequency photons). The term "detectable moiety" includes chromogenic, fluorescent, phosphorescent, and luminescent molecules and materials, catalysts (such as enzymes) that convert one substance into another substance to provide a detectable difference (such as by converting a colorless substance into a colored substance or vice versa, or by producing a precipitate or increasing sample turbidity). In some examples, the detectable moiety is a fluorophore, which belongs to several common chemical classes including coumarins, fluoresceins (or fluorescein derivatives and analogs), rhodamines, resorufins, luminophores and cyanines. Additional examples of fluorescent molecules can be found in Molecular Probes Handbook—A Guide to Fluorescent Probes and Labeling Technologies, Molecular Probes, Eugene, OR, ThermoFisher Scientific, $11^{th}$ Edition. In other embodiments, the detectable moiety is a molecule detectable via brightfield microscopy, such as dyes including diaminobenzidine (DAB), 4-(dimethylamino) azobenzene-4'-sulfonamide (DABSYL), tetramethylrhodamine (DISCOVERY Purple), N,N'-biscarboxypentyl-5,5'-disulfonato-indo-dicarbocyanine (Cy5), and Rhodamine 110 (Rhodamine).

Feature metric: A value indicative of an expression level of a biomarker in a sample. Examples include: expression intensity (for example, on a 0+, 1+, 2+, 3+ scale), number of cells positive for the biomarker, cell density (for example, number of biomarker-positive cells over an area of an ROI, number of biomarker-positive cells over a linear distance of an edge defining an ROI, and the like), pixel density (i.e. number of biomarker-positive pixels over an area of an ROI, number of biomarker-positive pixels over a linear distance of an edge defining an ROI, and the like), etc. A feature metric can be a total metric or a global metric.

Histochemical detection: A process involving labelling biomarkers or other structures in a tissue sample with biomarker-specific reagents and detection reagents in a manner that permits microscopic detection of the biomarker or other structures in the context of the cross-sectional relationship between the structures of the tissue sample. Examples include immunohistochemistry (IHC), chromogenic in situ hybridization (CISH), fluorescent in situ hybridization (FISH), silver in situ hybridization (SISH), and hematoxylin and eosin (H&E) staining of formalin-fixed, paraffin-embedded tissue sections.

Immune checkpoint-directed therapy: Any therapy that inhibits activation of an immune checkpoint molecule.

Immune checkpoint molecule: A protein expressed by an immune cell whose activation down-regulates a cytotoxic T-cell response. Examples include PD-1, TIM-3, LAG-4, and CTLA-4.

Immune escape biomarker: A biomarker expressed by a tumor cell that helps the tumor avoid a T-cell mediated immune response. Examples of immune escape biomarkers include PD-L1, PD-L2, and IDO.

Invasive margin (IM): The interface between invasive neoplastic tissue and normal tissue. When used in the context of an ROI, "IM" refers to an ROI restricted to a region of a tumor identified by an expert reader as an invasive margin.

Monoclonal antibody: An antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, or a combination thereof.

Non-linear continuous scoring function: A continuous scoring function having the general structure of anything other than f(x)=a+bx, wherein x is a variable and a and b are constants. Thus, for example, "non-linear continuous scoring function" includes non-linear algebraic functions (such as non-constant, non-linear polynomial functions; rational functions; and nth root functions) and transcendental functions (such as exponential functions, hyperbolic functions, logarithmic functions, and power functions).

Non-continuous scoring function: A "non-continuous scoring function" (also referred to herein as a "binary scoring function"), is a scoring function in which each variable is assigned to a pre-determined "bin" (for example, "high," "medium," or "low"), and the same value is input into the mathematical function for all members of the same bin. For example, assume that the variable being assessed is a density of CD8+ T-cells. In a non-continuous or binary scoring function, the density value is first analyzed to determine whether it falls into a "high density" or a "low density" bin, and the value that is input into the non-continuous scoring function is whatever arbitrary value is assigned to members of that bin (for example, 0 for low, 1 for high). Thus, consider two samples, a first having a density of 500 CD8+ cells/mm$^2$ and a second having a density of 700 CD8+ cells/mm$^2$. The values input into a non-continuous scoring function would depend on the bin in which they fall. If the "high bin" encompasses both 500 and 700 cells/mm$^2$, then a value of 1 would be input into the non-continuous scoring function for each sample. If the cutoff between "high" and "low" bins fell somewhere between 500 and 700 cells/mm$^2$, then a value of 0 would be input into a non-continuous scoring function for the first sample, and a value of 1 would be input into a non-continuous scoring function for the second sample. If the "low bin" encompasses both 500 and 700 cells/mm$^2$, then a value of 0 would be input into the non-continuous scoring function for each sample.

Normalize: To adjust a feature metric by a fixed factor so that different feature metrics are expressed on the same scale.

Normalization factor: A fixed factor applied to a feature metric to obtain a normalized feature metric.

Normalized feature metric: A feature metric, the value of which has been adjusted by a normalization factor.

Objective response rate: The proportion of subjects with reduction in tumor burden of a predefined amount.

Partial response (PR): As used herein, a subject is characterized as having a "partial response" after a particular therapy when there is at least a 30% decrease in the sum of the longest diameter (LD) of target lesions, taking as reference the baseline sum LD.

PD-1-axis directed therapy: Therapy that prevents PD-1-induced T-cell anergy, exhaustion, and/or senescence. Examples include PD-1-specific antibodies (such as nivolumab, pembrolizumab, cemiplimab, tislelizumab, spartalizumab, MEDI0680 (AstraZeneca), JS001 (Shanghai Junshi Biosciences), IBI308 (Innovent Biologics), JNJ-63723283), PD-L1-specific antibodies (such as atezolizumab, durvalumab, avelumab), PD-1 ligand fragments and fusion proteins (such as AMP-224 (a fusion between the extracellular domain of PD-L2 and the Fc region of human IgG1)), and small molecule inhibitors (such as CA-170 (small molecule with binding specificity for PD-L1, PD-L2 and VISTA, and BMS-1001 & BMS-1166 (small molecules predicted to dimerize PD-L1, see, e.g., WO2015034820 & WO2015160641).

Peri-tumoral (PT) region: The region of a tumor in the immediate vicinity of the invasive margin, which may also include a portion of the extra-tumoral tissue and a portion of the tumor core.

Peri-tumoral (PT) ROI: An ROI including at least a portion of the IM region, and optionally extra-tumoral tissue in the immediate vicinity of the IM region and/or a portion of the tumor core region in the immediate vicinity of the IM. For example, "PT ROI" may encompass all pixels within a defined distance of any point on the interface between tumor cells and non-tumor cells, or it may encompass an ROI of a defined width centered on the interface between tumor cells and non-tumor cells, or it may encompass an plurality of defined shapes each centered at a point on the interface between tumor cells and non-tumor cells (such as a plurality of overlapping circles, each centered at a discrete point on the interface between tumor cells and non-tumor cells).

Progressive disease (PD): As used herein, "progressive disease" is used to describe a subject who, following a particular therapy, has at least a 20% increase in the sum of the longest diameter (LD) of target lesions, taking as reference the smallest sum LD recorded since the therapy started or the appearance of one or more new lesions.

Sample: As used herein, the term "sample" shall refer to any material obtained from a subject capable of being tested for the presence or absence of a biomarker.

Secondary detection reagent: A specific detection reagent capable of specifically binding to a biomarker-specific reagent.

Section: When used as a noun, a thin slice of a tissue sample suitable for microscopic analysis, typically cut using a microtome. When used as a verb, the process of generating a section.

Serial section: As used herein, the term "serial section" shall refer to any one of a series of sections cut in sequence by a microtome from a tissue sample. For two sections to be considered "serial sections" of one another, they do not necessarily need to be consecutive sections from the tissue, but they should generally contain sufficiently similar tissue structures in the same spatial relationship, such that the structures can be matched to one another after histological staining.

Specific detection reagent: Any composition of matter that is capable of specifically binding to a target chemical structure in the context of a cellular sample. As used herein, the phrase "specific binding," "specifically binds to," or "specific for" or other similar iterations refers to measurable and reproducible interactions between a target and a specific detection reagent, which is determinative of the presence of the target in the presence of a heterogeneous population of molecules including biological molecules. For example, an antibody that specifically binds to a target is an antibody that binds this target with greater affinity, avidity, more readily, and/or with greater duration than it binds to other targets. In one embodiment, the extent of binding of a specific detection reagent to an unrelated target is less than about 10% of the binding of the antibody to the target as measured, e.g., by a radioimmunoassay (RIA). In certain embodiments, a biomarker-specific reagent that specifically binds to a target has a dissociation constant (Kd) of ≤1 μM, ≤100 nM, ≤10 nM, ≤1 nM, or ≤0.1 nM. In another embodiment, specific binding can include, but does not require exclusive binding. Exemplary specific detection reagents include nucleic acid probes specific for particular nucleotide sequences; antibodies and antigen binding fragments thereof; and engineered specific binding compositions, including ADNECTINS™ (scaffold based on 10th FN3 fibronectin; Bristol-Myers-Squibb Co.), AFFIBODYs™ (scaffold based on Z domain of protein A from *S. aureus*; Affibody AB, Solna, Sweden), AVIMERs™ (scaffold based on domain A/LDL receptor; Amgen, Thousand Oaks, CA), dAbs (scaffold based on VH or VL antibody domain; GlaxoSmithKline PLC, Cambridge, UK), DARPins™ (scaffold based on Ankyrin repeat proteins; Molecular Partners AG, Zürich, CH), ANTICALINs® (scaffold based on lipocalins; *Pieris* AG, Freising, DE), NANOBODYs® (scaffold based on VHH (camelid Ig); Ablynx N/V, Ghent, BE), TRANS-BODYs™ (scaffold based on Transferrin; Pfizer Inc., New York, NY), SMIPs (Emergent Biosolutions, Inc., Rockville, MD), and TETRANECTINs™ (scaffold based on C-type lectin domain (CTLD), tetranectin; Borean Pharma A/S, Aarhus, DK). Descriptions of such engineered specific binding structures are reviewed by Wurch et al., Development of Novel Protein Scaffolds as Alternatives to Whole Antibodies for Imaging and Therapy: Status on Discovery Research and Clinical Validation, Current Pharmaceutical Biotechnology, Vol. 9, pp. 502-509 (2008), the content of which is incorporated by reference.

Stable disease (SD): As used herein, a subject is characterized as having "stable disease" when there is neither sufficient shrinkage to qualify for partial response (PR) nor sufficient increase to qualify for progressive disease (PD) following a particular therapy, taking as reference the smallest sum LD since the therapy started.

Stain: When used as a noun, the term "stain" shall refer to any substance that can be used to visualize specific molecules or structures in a cellular sample for microscopic analysis, including brightfield microscopy, fluorescent microscopy, electron microscopy, and the like. When used as a verb, the term "stain" shall refer to any process that results in deposition of a stain on a cellular sample.

Subject: As used herein, the term "subject" or "individual" is a mammal. Mammals include, but are not limited to, domesticated animals (e.g., cows, sheep, cats, dogs, and horses), primates (e.g., humans and non-human primates such as monkeys), rabbits, and rodents (e.g., mice and rats). In certain embodiments, the individual or subject is a human.

Test sample: A tumor sample obtained from a subject having an unknown outcome at the time the sample is obtained.

Tissue sample: As used herein, the term "tissue sample" shall refer to a cellular sample that preserves the cross-sectional spatial relationship between the cells as they existed within the subject from which the sample was obtained.

Tumor core (CT): The region of an invasive neoplastic lesion that is not the invasive margin. In the context of an ROI, "CT" refers to a portion of a whole tumor region that is neither IM nor excluded from the ROI as an artifact.

Tumor sample: A tissue sample obtained from a tumor.

Whole tumor (WT) region: A portion of a tissue section characterized by one or more contiguous regions composed substantially entirely of invasive neoplastic cells, including both CT and IM regions.

Whole tumor ROI: An ROI limited to a whole tumor region.

II. Biomarker Descriptions

CD3: CD3 is a cell surface receptor complex that is frequently used as a defining biomarker for cells having a T-cell lineage. The CD3 complex is composed of 4 distinct polypeptide chains: CD3-gamma chain, CD3-delta chain, CD3epsilon chain, and CD3-zeta chain. CD3-gamma and CD3-delta each form heterodimers with CD3-epsilon (εγ-homodimer and εδ-heterodimer) while CD3-zeta forms a homodimer (ζζ-homodimer). Functionally, the εγ-homodimer, εδ-heterodimer, and ζζ-homodimer form a signaling complex with T-cell receptor complexes. Exemplary sequences for (and isoforms and variants of) the human CD3-gamma chain, CD3-delta chain, CD3epsilon chain, and CD3-zeta chain can be found at Uniprot Accesion Nos. P09693 (the canonical amino acid sequence for which is disclosed herein at SEQ ID NO: 1), P04234 (the canonical amino acid sequence for which is disclosed herein at SEQ ID NO: 2), P07766 (the canonical amino acid sequence for which is disclosed herein at SEQ ID NO: 3), and P20963 (the canonical amino acid sequence for which is disclosed herein at SEQ ID NO: 4), respectively. As used herein, the term "human CD3 protein biomarker" encompasses any CD3-gamma chain, CD3-delta chain, CD3epsilon chain, and CD3-zeta chain polypeptide having a canonical human sequence and natural variants thereof that maintain the function of the canonical sequence; εγ-homodimers, εδ-heterodimers, and ζζ-homodimers including one of more of CD3-gamma chain, CD3-delta chain, CD3epsilon chain, and CD3-zeta chain polypeptide having a canonical human sequence and natural variants thereof that maintain the function of the canonical sequence; and any signaling complex including one or more of the foregoing CD3 homodimers or heterodimers. In some embodiments, a human CD3 protein biomarker-specific agent encompasses any biomarker-specific agent that specifically binds a structure (such as an epitope) within CD3-gamma chain polypeptide (such as the polypeptide at SEQ ID NO: 1), CD3-delta chain polypeptide (such as the polypeptide at SEQ ID NO: 2), CD3epsilon chain polypeptide (such as the polypeptide at SEQ ID NO: 3), or CD3-zeta chain polypeptide (such as the polypeptide at SEQ ID NO: 4), or that binds to a structure (such as an epitope) located within εγ-homodimer, εδ-heterodimer, or ζζ-homodimer.

CD8: CD8 is a heterodimeric, disulphide linked, transmembrane glycoprotein found on the cytotoxic-suppressor T cell subset, on thymocytes, on certain natural killer cells, and in a subpopulation of bone marrow cells. Exemplary sequences for (and isoforms and variants of) the human alpha- and beta-chain of the CD8 receptor can be found at Uniprot Accession Nos. P01732 (the canonical amino acid sequence for which is disclosed herein at SEQ ID NO: 5) and P10966 (the canonical amino acid sequence for which is disclosed herein at SEQ ID NO: 6), respectively. As used herein, the term "human CD8 protein biomarker" encompasses any CD8-alpha chain polypeptide having a canonical human sequence and natural variants thereof that maintain the function of the canonical sequence; any CD8-beta chain polypeptide having a canonical human sequence and natural variants thereof that maintain the function of the canonical sequence; any dimers including a CD8-alpha chain polypeptide having a canonical human sequence and natural variants thereof that maintain the function of the canonical sequence and/or a CD8-beta chain polypeptide having a canonical human sequence and natural variants thereof that maintain the function of the canonical sequence. In some embodiments, a human CD8 protein biomarker-specific agent encompasses any biomarker-specific agent that specifically binds a structure (such as an epitope) within CD8-alpha chain polypeptide (such as the polypeptide at SEQ ID NO: 5), CD8-beta chain polypeptide (such as the polypeptide at SEQ ID NO: 6), or that binds to a structure (such as an epitope) located within a CD8 dimer.

CTLA-4: CTLA-4 (also known as CD152), is an immune checkpoint protein expressed by the CTLA4 gene on chromosome 2 of humans. Exemplary sequences for (and isoforms and variants of) the human CTLA-4 protein can be found at Uniprot Accesion No. P16410 (the canonical amino acid sequence for which is disclosed herein at SEQ ID NO: 7).

PD-1: Programmed death-1 (PD-1) is a member of the CD28 family of receptors encoded by the PDCDI gene on chromosome 2. Exemplary sequences for (and isoforms and variants of) the human PD-1 protein can be found at Uniprot Accesion No. Q15116 (the canonical amino acid sequence for which is disclosed herein at SEQ ID NO: 8). In some embodiments, a human PD-1 protein biomarker-specific agent encompasses any biomarker-specific agent that specifically binds a structure (such as an epitope) within a human PD-1 polypeptide (such as the polypeptide at SEQ ID NO: 8).

PD-L1: Programmed death ligand 1 (PD-L1) is a type 1 transmembrane protein encoded by the CD274 gene on chromosome 9. PD-L1 acts as a ligand for PD-1 and CD80. Exemplary sequences for (and isoforms and variants of) the human PD-L1 protein can be found at Uniprot Accesion No. Q9NZQ7 (the canonical amino acid sequence for which is disclosed herein at SEQ ID NO: 9). In some embodiments, a human PD-L1 protein biomarker-specific agent encompasses any biomarker-specific agent that specifically binds a structure (such as an epitope) within a human PD-L1 polypeptide (such as the polypeptide at SEQ ID NO: 9).

PD-L2: Programmed death ligand 2 (PD-L2) is a transmembrane protein encoded by the PDCDILG2 gene on chromosome 9. PD-L2 acts as a ligand for PD-1. Exemplary sequences for (and isoforms and variants of) the human PD-L2 protein can be found at Uniprot Accesion No. Q9BQ51 (the canonical amino acid sequence for which is disclosed herein at SEQ ID NO: 10). In some embodiments, a human PD-L2 protein biomarker-specific agent encompasses any biomarker-specific agent that specifically binds a structure (such as an epitope) within a human PD-L2 polypeptide (such as the polypeptide at SEQ ID NO: 10).

III. Scoring Function

The scoring functions of the present methods and systems are applied to tumor samples from patients having stage IV colorectal cancer with deficient DNA mismatch repair. A panel of biomarkers to test is selected, the samples are stained for the biomarkers, and feature metrics for the biomarkers are calculated from one or more ROIs (which feature metrics optionally may be normalized and/or subject to upper or lower limits).

The present scoring functions are based on a density of CD8+ cells located within a tumor core (CT). Additional biomarkers may be included in the scoring function (e.g., CD3+ densities) and/or from different tissue compartments (e.g., invasive margin), so long as they do not significantly reduce the ability of the scoring function to predict the subject's response to a particular treatment course.

In one embodiment, the scoring function described herein is a non-continuous scoring function in which the density of CD3+ and CD8+ T-cells within each compartment (e.g., CT) is calculated by dividing the cell count by the area ($mm^2$) of the tumor compartment. Density values are used to calculate a density score ranging from 0 to 100 for each T-cell subtype and compartment (CD3+ IM, CD3+ CT, CD8+ IM, CD8+ CT) and a threshold value is determined to distinguish between "high" and "low" ICS. In an exemplary embodiment, the threshold value is determined by receiver operating characteristic (ROC) curve analysis.

In another embodiment, the scoring function described herein is a continuous scoring function comprising at least CD8+ T-cell density in a CT, wherein the CD8+ T-cell density in the CT region has the highest weight of the variables in the continuous scoring function. Exemplary continuous scoring function models useful in the current invention include Cox proportional hazard models and logistic regression models. In an embodiment, a multivariate continuous scoring model is provided comprising CD8+ T-cell density in a CT region as the variable having the highest weight in the model.

III.A. Samples and Sample Preparation

The non-continuous scoring function is executed on an image of a tissue section obtained from a stage IV colorectal tumor. The samples are typically tissue samples processed in a manner compatible with histochemical staining, including, for example, fixation (such as with a formalin-based fixative), embedding in a wax matrix (such as paraffin), and sectioning (such as with a microtome). No specific processing step is required by the present disclosure, so long as the sample obtained is compatible with histochemical staining of the sample for the biomarkers of interest. In a specific embodiment, the sample is a microtome section of a formalin-fixed, paraffin-embedded (FFPE) tissue samples of a stage IV colorectal cancer tumor.

III.B. Biomarker Panels

In an embodiment, at least one tissue section of the stage IV colorectal sample is labeled with a human CD8 protein biomarker-specific reagent in combination with appropriate detection reagents, and a density of CD8+ cells is evaluated. Additionally, the tumor may be classified on the basis of mismatch repair and/or microsatellite stability status.

Mismatch repair status (also termed "MMR") typically involves evaluating the expression and/or methylation status of four genes involved in mismatch repair: hPMS2, hMLH1, hMSH2, and hMSH6. Canonical protein sequences are disclosed at SEQ ID NO: 11-14, respectively. A tumor having deficient expression of any one of these four is determined to have deficient mismatch repair (termed "dMMR"), while a tumor that is not deficient in expression of any of these genes is determined to have proficient MMR (termed "pMMR"). MMR status may be determined, for example, a protein-based assay (such as by immunoassay, such as a solid-phase enzyme immunoassay (e.g., ELISA) or immunohistochemical assay) or a polymerase chain reaction (PCR) assay (such as a real-time reverse transcriptase PCR assay).

Microsatellite instability ("MSI") is caused by MMR deficiency. As a result, alterations in the length of microsatellite loci begin to accumulate. Assays for evaluating MSI status are well known in the art. See, e.g., Murphy et al., J. Mol. Diagn., Vol. 8, Issue 3, pp. 305-11 (July 2006); Esemuede et al., Ann. Surg. Oncol., vol. 17, Issue 12, pp. 3370-78 (December 2010); Mukherjee et al., Hereditary Cancer in Clinical Practice, Vol. 8, Issue 9 (2010); MSI Analysis System (Promega) (evaluation of seven markers for MSI-high phenotype, including five nearly monomorphic mononucleotide repeat markers (BAT-25, BAT-26, MONO-27, NR-21 and NR-24) and two highly polymorphic pentanucleotide repeat markers (Penta C and Penta D)).

III.C. Histochemical Staining of Samples

Sections of the samples are stained by applying one or more biomarker-specific reagents in combination with a set of appropriate detection reagents to generate a biomarker-stained section. Biomarker staining is typically accomplished by contacting a section of the sample with a biomarker-specific reagent under conditions that facilitate specific binding between the biomarker and the biomarker-specific reagent. The sample is then contacted with a set of detection reagents that interact with the biomarker-specific reagent to facilitate deposition of a detectable moiety in close proximity to the biomarker, thereby generating a detectable signal localized to the biomarker. Typically, wash steps are performed between application of different reagents to prevent unwanted non-specific staining of tissues.

The biomarker-specific reagent facilitates detection of the biomarker by mediating deposition of a detectable moiety in close proximity to the biomarker-specific reagent.

In some embodiments, the detectable moiety is directly conjugated to the biomarker-specific reagent, and thus is deposited on the sample upon binding of the biomarker-specific reagent to its target (generally referred to as a direct labeling method). Direct labeling methods are often more directly quantifiable, but often suffer from a lack of sensitivity. In other embodiments, deposition of the detectable moiety is effected by the use of a detection reagent associated with the biomarker-specific reagent (generally referred to as an indirect labeling method). Indirect labeling methods have the increase the number of detectable moieties that can be deposited in proximity to the biomarker-specific reagent, and thus are often more sensitive than direct labeling methods, particularly when used in combination with dyes.

In some embodiments, an indirect method is used, wherein the detectable moiety is deposited via an enzymatic reaction localized to the biomarker-specific reagent. Suitable enzymes for such reactions are well-known and include, but are not limited to, oxidoreductases, hydrolases, and peroxidases. Specific enzymes explicitly included are horseradish peroxidase (HRP), alkaline phosphatase (AP), acid phosphatase, glucose oxidase, β-galactosidase, β-glucuronidase, and β-lactamase. The enzyme may be directly conjugated to the biomarker-specific reagent, or may be indirectly associated with the biomarker-specific reagent via a labeling conjugate. As used herein, a "labeling conjugate" comprises:

(a) a specific detection reagent; and (b) an enzyme conjugated to the specific detection reagent, wherein the enzyme is reactive with the chromogenic substrate, signaling conjugate, or enzyme-reactive dye under appropriate reaction conditions to effect in situ generation of the dye and/or deposition of the dye on the tissue sample.

In non-limiting examples, the specific detection reagent of the labeling conjugate may be a secondary detection reagent (such as a species-specific secondary antibody bound to a primary antibody, an anti-hapten antibody bound to a hapten-conjugated primary antibody, or a biotin-binding protein bound to a biotinylated primary antibody), a tertiary detection reagent (such as a species-specific tertiary antibody bound to a secondary antibody, an anti-hapten antibody bound to a hapten-conjugated secondary antibody, or a biotin-binding protein bound to a biotinylated secondary antibody), or other such arrangements. An enzyme thus localized to the sample-bound biomarker-specific reagent can then be used in a number of schemes to deposit a detectable moiety.

In some cases, the enzyme reacts with a chromogenic compound/substrate. Particular non-limiting examples of chromogenic compounds/substrates include 4-nitrophenylphospate (pNPP), fast red, bromochloroindolyl phosphate (BCIP), nitro blue tetrazolium (NBT), BCIP/NBT, fast red, AP Orange, AP blue, tetramethylbenzidine (TMB), 2,2'-azino-di-[3-ethylbenzothiazoline sulphonate](ABTS), o-dianisidine, 4-chloronaphthol (4-CN), nitrophenyl-β-D-galactopyranoside (ONPG), o-phenylenediamine (OPD), 5-bromo-4-chloro-3-indolyl-β-galactopyranoside (X-Gal), methylumbelliferyl-β-D-galactopyranoside (MU-Gal), p-nitrophenyl-α-D-galactopyranoside (PNP), 5-bromo-4-chloro-3-indolyl-β-D-glucuronide (X-Gluc), 3-amino-9-ethyl carbazol (AEC), fuchsin, iodonitrotetrazolium (INT), tetrazolium blue, or tetrazolium violet.

In some embodiments, the enzyme can be used in a metallographic detection scheme. Metallographic detection methods include using an enzyme such as alkaline phosphatase in combination with a water-soluble metal ion and a redox-inactive substrate of the enzyme. In some embodiments, the substrate is converted to a redox-active agent by the enzyme, and the redox-active agent reduces the metal ion, causing it to form a detectable precipitate. (see, for example, U.S. patent application Ser. No. 11/015,646, filed Dec. 20, 2004, PCT Publication No. 2005/003777 and U.S. Patent Application Publication No. 2004/0265922; each of which is incorporated by reference herein in its entirety). Metallographic detection methods include using an oxido-reductase enzyme (such as horseradish peroxidase) along with a water soluble metal ion, an oxidizing agent and a reducing agent, again to for form a detectable precipitate. (See, for example, U.S. Pat. No. 6,670,113, which is incorporated by reference herein in its entirety).

In some embodiments, the enzymatic action occurs between the enzyme and the dye itself, wherein the reaction converts the dye from a non-binding species to a species deposited on the sample. For example, reaction of DAB with a peroxidase (such as horseradish peroxidase) oxidizes the DAB, causing it to precipitate.

In yet other embodiments, the detectable moiety is deposited via a signaling conjugate comprising a latent reactive moiety configured to react with the enzyme to form a reactive species that can bind to the sample or to other detection components. These reactive species are capable of reacting with the sample proximal to their generation, i.e. near the enzyme, but rapidly convert to a non-reactive species so that the signaling conjugate is not deposited at sites distal from the site at which the enzyme is deposited. Examples of latent reactive moieties include: quinone methide (QM) analogs, such as those described at WO2015124703A1, and tyramide conjugates, such as those described at, WO2012003476A2, each of which is hereby incorporated by reference herein in its entirety. In some examples, the latent reactive moiety is directly conjugated to a dye, such as N,N'-biscarboxypentyl-5,5'-disulfonato-indo-dicarbocyanine (Cy5), 4-(dimethylamino) azobenzene-4'-sulfonamide (DABSYL), tetramethylrhodamine (DISCO Purple), and Rhodamine 110 (Rhodamine). In other examples, the latent reactive moiety is conjugated to one member of a specific binding pair, and the dye is linked to the other member of the specific binding pair. In other examples, the latent reactive moiety is linked to one member of a specific binding pair, and an enzyme is linked to the other member of the specific binding pair, wherein the enzyme is (a) reactive with a chromogenic substrate to effect generation of the dye, or (b) reactive with a dye to effect deposition of the dye (such as DAB). Examples of specific binding pairs include:

(1) a biotin or a biotin derivative (such as desthiobiotin) linked to the latent reactive moiety, and a biotin-binding entity (such as avidin, streptavidin, deglycosylated avidin (such as NEUTRAVIDIN), or a biotin binding protein having a nitrated tyrosine at its biotin binding site (such as CAPTAVIDIN)) linked to a dye or to an enzyme reactive with a chromogenic substrate or reactive with a dye (for example, a peroxidase linked to the biotin-binding protein when the dye is DAB); and (2) a hapten linked to the latent reactive moiety, and an anti-hapten antibody linked to a dye or to an enzyme reactive with a chromogenic substrate or reactive with a dye (for example, a peroxidase linked to the biotin-binding protein when the dye is DAB).

Non-limiting examples of biomarker-specific reagent and detection reagent combinations are set forth in Table 1 are specifically included.

TABLE 1

| | |
|---|---|
| A. Biomarker-specific reagent linked directly to detectable moiety | |
| | Biomarker-specific reagent-Dye conjugate |
| B. Biomarker-specific reagent linked to enzyme reacting with detectable moiety | |
| | Biomarker-specific reagent-Enzyme conjugate + DAB |
| | Biomarker-specific reagent-Enzyme conjugate + Chromogen |
| C. Biomarker-specific reagent linked to Enzyme reacting with signaling conjugate | |
| C1. Signaling conjugate comprises detectable moiety | Biomarker-specific reagent-Enzyme conjugate + QM-Dye conjugate |
| | Biomarker-specific reagent-Enzyme conjugate + Tyramide-Dye conjugate |
| C2. Signaling conjugate comprises enzyme that reacts directly with detectable moiety | Biomarker-specific reagent-Enzyme conjugate + QM-Enzyme conjugate + DAB |
| | Biomarker-specific reagent-Enzyme conjugate + QM-Enzyme conjugate + Chromogen |
| | Biomarker-specific reagent-Enzyme conjugate + Tyramide-Enzyme conjugate + DAB |
| | Biomarker-specific reagent-Enzyme conjugate + Tyramide-Enzyme conjugate + Chromogen |
| C3. Signaling conjugate comprises enzyme that reacts with second signaling conjugate comprising detectable moiety | Biomarker-specific reagent-Enzyme conjugate + QM-Enzyme conjugate + QM-Dye conjugate |
| | Biomarker-specific reagent-Enzyme conjugate + QM-Enzyme conjugate + Tyramide-Dye conjugate |
| | Biomarker-specific reagent-Enzyme conjugate + Tyramide-Enzyme conjugate + QM-Dye conjugate |
| | Biomarker-specific reagent-Enzyme conjugate + Tyramide-Enzyme conjugate + Tyramide-Dye conjugate |
| C4. Signaling conjugate comprises member of a specific binding pair and other member of binding pair is linked to detectable moiety | Biomarker-specific reagent-Enzyme conjugate + Tyramide-(biotin/hapten) conjugate + Dye-(avidin/anti-hapten biomarker-specific reagent) conjugate |
| | Biomarker-specific reagent-Enzyme conjugate + QM-(biotin/hapten) conjugate + Dye-(avidin/anti-hapten biomarker-specific reagent) conjugate |
| C5. Signaling conjugate comprises member of a specific binding pair and other member of binding pair is linked to enzyme reactive with detectable moiety | Biomarker-specific reagent-Enzyme conjugate + QM-(biotin/hapten) conjugate + Enzyme-(avidin/anti-hapten biomarker-specific reagent) conjugate + DAB |
| | Biomarker-specific reagent-Enzyme conjugate + QM-(biotin/hapten) conjugate + Enzyme-(avidin/anti-hapten biomarker-specific reagent) conjugate + Chromogen |
| | Biomarker-specific reagent-Enzyme conjugate + Tyramide-(biotin/hapten) conjugate + Enzyme-(avidin/anti-hapten biomarker-specific reagent) conjugate + DAB |
| | Biomarker-specific reagent-Enzyme conjugate + Tyramide-(biotin/hapten) conjugate + Enzyme-(avidin/anti-hapten biomarker-specific reagent) conjugate + Chromogen |
| C6. Signaling conjugate comprises member of a specific binding pair and other member of binding pair is linked to enzyme reactive with second detectable moiety linked to a detectable moiety | Biomarker-specific reagent-Enzyme conjugate + QM-(biotin/hapten) conjugate + Enzyme-(avidin/anti-hapten biomarker-specific reagent) conjugate + Tyramide-Dye conjugate |
| | Biomarker-specific reagent-Enzyme conjugate + QM-(biotin/hapten) conjugate + Enzyme-(avidin/anti-hapten biomarker-specific reagent) conjugate + QM-Dye conjugate |
| | Biomarker-specific reagent-Enzyme conjugate + Tyramide-(biotin/hapten) conjugate + Enzyme-(avidin/anti-hapten biomarker-specific reagent) conjugate + Tyramide-Dye conjugate |
| | Biomarker-specific reagent-Enzyme conjugate + Tyramide-(biotin/hapten) conjugate + Enzyme-(avidin/anti-hapten biomarker-specific reagent) conjugate + QM-Dye conjugate |
| D. Biomarker-specific reagent linked to member of specific binding pair | |
| D1. Dye linked to other member of specific binding pair | Biomarker-specific reagent-(biotin/hapten) conjugate + Dye-(avidin/anti-hapten biomarker-specific reagent) conjugate |
| D2. Enzyme linked to other member of specific binding pair, wherein the enzyme is reactive with detectable moiety | Biomarker-specific reagent-(biotin/hapten) conjugate + Enzyme-(avidin/anti-hapten biomarker-specific reagent) conjugate + DAB |
| | Biomarker-specific reagent-(biotin/hapten) conjugate + Enzyme-(avidin/anti-hapten biomarker-specific reagent) |

TABLE 1-continued

| | |
|---|---|
| | conjugate + Chromogen |
| | Biomarker-specific reagent-(biotin/hapten) conjugate + Enzyme-(avidin/anti-hapten biomarker-specific reagent) conjugate + QM-Dye conjugate |
| | Biomarker-specific reagent-(biotin/hapten) conjugate + Enzyme-(avidin/anti-hapten biomarker-specific reagent) conjugate + Tyramide-Dye conjugate |
| E. Secondary detection reagent linked directly to detectable moiety | |
| Biomarker-specific reagent + 2° specific detection reagent-Dye conjugate | |
| F. Secondary detection reagent linked to Enzyme reacting with detectable moiety | |
| Biomarker-specific reagent + 2° specific detection reagent-Enzyme conjugate + DAB | |
| Biomarker-specific reagent + 2° specific detection reagent-Enzyme conjugate + Chromogen | |
| G. Secondary detection reagent linked to Enzyme reacting with signaling conjugate | |
| G1. Signaling conjugate comprises detectable moiety | Biomarker-specific reagent + 2° specific detection reagent-Enzyme conjugate + QM-Dye conjugate |
| | Biomarker-specific reagent + 2° specific detection reagent-Enzyme conjugate + Tyramide-Dye conjugate |
| G2. Signaling conjugate comprises enzyme that reacts directly with detectable moiety | Biomarker-specific reagent + 2° specific detection reagent-Enzyme conjugate + QM-Enzyme conjugate + DAB |
| | Biomarker-specific reagent + 2° specific detection reagent-Enzyme conjugate + QM-Enzyme conjugate + Chromogen |
| | Biomarker-specific reagent + 2° specific detection reagent-Enzyme conjugate + Tyramide-Enzyme conjugate + DAB |
| | Biomarker-specific reagent + 2° specific detection reagent-Enzyme conjugate + Tyramide-Enzyme conjugate + Chromogen |
| G3. Signaling conjugate comprises enzyme that reacts with second signaling conjugate comprising detectable moiety | Biomarker-specific reagent + 2° specific detection reagent-Enzyme conjugate + QM-Enzyme conjugate + QM-Dye conjugate |
| | Biomarker-specific reagent + 2° specific detection reagent-Enzyme conjugate + QM-Enzyme conjugate + Tyramide-Dye conjugate |
| | Biomarker-specific reagent + 2° specific detection reagent-Enzyme conjugate + Tyramide-Enzyme conjugate + QM-Dye conjugate |
| | Biomarker-specific reagent + 2° specific detection reagent-Enzyme conjugate + Tyramide-Enzyme conjugate + Tyramide-Dye conjugate |
| G4. Signaling conjugate comprises member of a specific binding pair and other member of binding pair is linked to detectable moiety | Biomarker-specific reagent + 2° specific detection reagent-Enzyme conjugate + Tyramide-(biotin/hapten) conjugate + Dye-(avidin/anti-hapten biomarker-specific reagent) conjugate |
| | Biomarker-specific reagent + 2° specific detection reagent-Enzyme conjugate + QM-(biotin/hapten) conjugate + Dye-(avidin/anti-hapten biomarker-specific reagent) conjugate |
| G5. Signaling conjugate comprises member of a specific binding pair and other member of binding pair is linked to enzyme reactive with detectable moiety | Biomarker-specific reagent + 2° specific detection reagent-Enzyme conjugate + QM-(biotin/hapten) conjugate + Enzyme-(avidin/anti-hapten biomarker- specific reagent) conjugate + DAB |
| | Biomarker-specific reagent + 2° specific detection reagent-Enzyme conjugate + QM-(biotin/hapten) conjugate + Enzyme-(avidin/anti-hapten biomarker-specific reagent) conjugate + Chromogen |
| | Biomarker-specific reagent + 2° specific detection reagent-Enzyme conjugate + Tyramide-(biotin/hapten) conjugate + Enzyme-(avidin/anti-hapten biomarker-specific reagent) conjugate + DAB |
| | Biomarker-specific reagent + 2° specific detection reagent-Enzyme conjugate + Tyramide-(biotin/hapten) conjugate + Enzyme-(avidin/anti-hapten biomarker-specific reagent) conjugate + Chromogen |
| G6. Signaling conjugate comprises member of a specific binding pair and other member of binding pair is linked to enzyme reactive with second detectable moiety linked to a detectable moiety | Biomarker-specific reagent + 2° specific detection reagent-Enzyme conjugate + QM-(biotin/hapten) conjugate + Enzyme-(avidin/anti-hapten biomarker- specific reagent) conjugate + Tyramide-Dye conjugate |
| | Biomarker-specific reagent + 2° specific detection reagent-Enzyme conjugate + QM-(biotin/hapten) conjugate + Enzyme-(avidin/anti-hapten biomarker- specific reagent) conjugate + QM-Dye conjugate |
| | Biomarker-specific reagent + 2° specific detection reagent-Enzyme conjugate + Tyramide-(biotin/hapten) conjugate + Enzyme-(avidin/anti-hapten biomarker-specific reagent) conjugate + Tyramide-Dye conjugate |
| | Biomarker-specific reagent + 2° specific detection reagent-Enzyme conjugate + Tyramide-(biotin/hapten) conjugate + Enzyme-(avidin/anti-hapten biomarker-specific reagent) conjugate + QM-Dye conjugate |

TABLE 1-continued

| | |
|---|---|
| H. Secondary detection reagent linked to member of specific binding pair | |
| H1. Dye linked to other member of specific binding pair | Biomarker-specific reagent + 2° specific detection reagent-(biotin/hapten) conjugate + Dye-(avidin/anti-hapten biomarker-specific reagent) conjugate |
| H2. Enzyme linked to other member of specific binding pair, wherein the enzyme is reactive with detectable moiety | Biomarker-specific reagent + 2° specific detection reagent-(biotin/hapten) conjugate + Enzyme-(avidin/anti-hapten biomarker-specific reagent) conjugate + DAB |
| | Biomarker-specific reagent + 2° specific detection reagent-(biotin/hapten) conjugate + Enzyme-(avidin/anti-hapten biomarker-specific reagent) conjugate + Chromogen |
| | Biomarker-specific reagent + 2° specific detection reagent-(biotin/hapten) conjugate + Enzyme-(avidin/anti-hapten biomarker-specific reagent) conjugate + QM-Dye conjugate |
| | Biomarker-specific reagent + 2° specific detection reagent-(biotin/hapten) conjugate + Enzyme-(avidin/anti-hapten biomarker-specific reagent) conjugate + Tyramide-Dye conjugate |
| I. Tertiary specific detection reagent linked directly to detectable moiety | |
| Biomarker-specific reagent + 2° specific detection reagent + 3° specific detection reagent-Dye conjugate | |
| J. Tertiary specific detection reagent linked to Enzyme reacting with detectable moiety | |
| Biomarker-specific reagent + 2° specific detection reagent + 3° specific detection reagent-Enzyme conjugate + DAB | |
| Biomarker-specific reagent + 2° specific detection reagent + 3° specific detection reagent-Enzyme conjugate + Chromogen | |
| K. Tertiary specific detection reagent linked to Enzyme reacting with signaling conjugate | |
| K1. Signaling conjugate comprises detectable moiety | Biomarker-specific reagent + 2° specific detection reagent + 3° specific detection reagent-Enzyme conjugate + QM-Dye conjugate |
| | Biomarker-specific reagent + 2° specific detection reagent + 3° specific detection reagent-Enzyme conjugate + Tyramide-Dye conjugate |
| K2. Signaling conjugate comprises enzyme that reacts directly with detectable moiety | Biomarker-specific reagent + 2° specific detection reagent + 3° specific detection reagent-Enzyme conjugate + QM-Enzyme conjugate + DAB |
| | Biomarker-specific reagent + 2° specific detection reagent + 3° specific detection reagent-Enzyme conjugate + QM-Enzyme conjugate + Chromogen |
| | Biomarker-specific reagent + 2° specific detection reagent + 3° specific detection reagent-Enzyme conjugate + Tyramide-Enzyme conjugate + DAB |
| | Biomarker-specific reagent + 2° specific detection reagent + 3° specific detection reagent-Enzyme conjugate + Tyramide-Enzyme conjugate + Chromogen |
| K3. Signaling conjugate comprises enzyme that reacts with second signaling conjugate comprising detectable moiety | Biomarker-specific reagent + 2° specific detection reagent + 3° specific detection reagent-Enzyme conjugate + QM-Enzyme conjugate + QM-Dye conjugate |
| | Biomarker-specific reagent + 2° specific detection reagent + 3° specific detection reagent-Enzyme conjugate + QM-Enzyme conjugate + Tyramide-Dye conjugate |
| | Biomarker-specific reagent + 2° specific detection reagent + 3° specific detection reagent-Enzyme conjugate + Tyramide-Enzyme conjugate + QM-Dye conjugate |
| | Biomarker-specific reagent + 2° specific detection reagent + 3° specific detection reagent-Enzyme conjugate + Tyramide-Enzyme conjugate + Tyramide-Dye conjugate |
| K4. Signaling conjugate comprises member of a specific binding pair and other member of binding pair is linked to detectable moiety | Biomarker-specific reagent + 2° specific detection reagent + 3° specific detection reagent-Enzyme conjugate + Tyramide-(biotin/hapten) conjugate + Dye-(avidin/anti-hapten biomarker-specific reagent) conjugate |
| | Biomarker-specific reagent + 2° specific detection reagent + 3° specific detection reagent-Enzyme conjugate + QM-(biotin/hapten) conjugate + Dye-(avidin/anti-hapten biomarker-specific reagent) conjugate |
| K5. Signaling conjugate comprises member of a QM-(biotin/hapten) specific binding pair and other member of binding pair is linked to enzyme reactive with detectable moiety | Biomarker-specific reagent + 2° specific detection reagent + 3° specific detection reagent-Enzyme conjugate + conjugate + Enzyme-(avidin/anti-hapten biomarker-specific reagent) conjugate + DAB |
| | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + Chromogen |
| | Biomarker-specific reagent + 2° specific detection reagent + 3° specific detection reagent-Enzyme conjugate + Tyramide-(biotin/hapten) conjugate + Enzyme- |

TABLE 1-continued

| | |
|---|---|
| | (avidin/anti-hapten biomarker-specific reagent) conjugate + DAB |
| | Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + Chromogen |
| K6. Signaling conjugate comprises member of a specific binding pair and other member of binding pair is linked to enzyme reactive with second detectable moiety linked to a detectable moiety | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + Tyramide-Dye conjugate |
| | Biomarker-specific reagent + 2° specific detection reagent + 3° specific detection reagent-Enzyme conjugate + QM-(biotin/hapten) conjugate + Enzyme-(avidin/anti-hapten biomarker-specific reagent) conjugate + QM-Dye conjugate |
| | Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + Tyramide-Dye conjugate |
| | Biomarker-specific reagent + 2° specific detection reagent + 3° specific detection reagent-Enzyme conjugate + Tyramide-(biotin/hapten) conjugate + Enzyme-(avidin/anti-hapten biomarker-specific reagent) conjugate + QM-Dye conjugate |
| L. Tertiary specific detection reagent linked to member of specific binding pair | |
| L1. Dye linked to other member of specific binding pair | Biomarker-specific reagent + 2° specific detection reagent + 3° specific detection reagent-(biotin/hapten) conjugate + Dye-(avidin/anti-hapten biomarker-specific reagent) conjugate |
| L2. Enzyme linked to other member of specific binding pair, wherein the enzyme is reactive with detectable moiety | Biomarker-specific reagent + 2° specific detection reagent + 3° specific detection reagent-(biotin/hapten) conjugate + Enzyme-(avidin/anti-hapten biomarker-specific reagent) conjugate + DAB |
| | Biomarker-specific reagent + 2° specific detection reagent + 3° specific detection reagent-(biotin/hapten) conjugate + Enzyme-(avidin/anti-hapten biomarker-specific reagent) conjugate + Chromogen |
| | Biomarker-specific reagent + 2° specific detection reagent + 3° specific detection reagent-(biotin/hapten) conjugate + Enzyme-(avidin/anti-hapten biomarker-specific reagent) conjugate + QM-Dye conjugate |
| | Biomarker-specific reagent + 2° specific detection reagent + 3° specific detection reagent-(biotin/hapten) conjugate + Enzyme-(avidin/anti-hapten biomarker-specific reagent) conjugate + Tyramide-Dye conjugate |

In a specific embodiment, the biomarker-specific reagents and the specific detection reagents set forth in Table 1 are antibodies. As would be appreciated by a person having ordinary skill in the art, the detection scheme for each of the biomarker-specific reagents may be the same, or it may be different.

Non-limiting examples of commercially available detection reagents or kits comprising detection reagents suitable for use with present methods include: VENTANA ultra View detection systems (secondary antibodies conjugated to enzymes, including HRP and AP); VENTANA iVIEW detection systems (biotinylated anti-species secondary antibodies and streptavidin-conjugated enzymes); VENTANA OptiView detection systems (OptiView) (anti-species secondary antibody conjugated to a hapten and an anti-hapten tertiary antibody conjugated to an enzyme multimer); VENTANA Amplification kit (unconjugated secondary antibodies, which can be used with any of the foregoing VENTANA detection systems to amplify the number of enzymes deposited at the site of primary antibody binding); VENTANA OptiView Amplification system (Anti-species secondary antibody conjugated to a hapten, an anti-hapten tertiary antibody conjugated to an enzyme multimer, and a tyramide conjugated to the same hapten. In use, the secondary antibody is contacted with the sample to effect binding to the primary antibody. Then the sample is incubated with the anti-hapten antibody to effect association of the enzyme to the secondary antibody. The sample is then incubated with the tyramide to effect deposition of additional hapten molecules. The sample is then incubated again with the anti-hapten antibody to effect deposition of additional enzyme molecules. The sample is then incubated with the detectable moiety to effect dye deposition); VENTANA DISCOVERY, DISCOVERY OmniMap, DISCOVERY UltraMap anti-hapten antibody, secondary antibody, chromogen, fluorophore, and dye kits, each of which are available from Ventana Medical Systems, Inc. (Tucson, Arizona); PowerVision and PowerVision+ IHC Detection Systems (secondary antibodies directly polymerized with HRP or AP into compact polymers bearing a high ratio of enzymes to antibodies); and DAKO EnVision™+ System (enzyme labeled polymer that is conjugated to secondary antibodies).

III.D Counterstaining

If desired, the biomarker-stained slides may be counterstained to assist in identifying morphologically relevant areas for identifying ROIs, either manually or automatically. Examples of counterstains include chromogenic nuclear counterstains, such as hematoxylin (stains from blue to violet), Methylene blue (stains blue), toluidine blue (stains nuclei deep blue and polysaccharides pink to red), nuclear fast red (also called Kernechtrot dye, stains red), and methyl green (stains green); non-nuclear chromogenic stains, such as eosin (stains pink); fluorescent nuclear stains, including 4', 6-diamino-2-pheylindole (DAPI, stains blue), propidium iodide (stains red), Hoechst stain (stains blue), nuclear green DCS1 (stains green), nuclear yellow (Hoechst S769121, stains yellow under neutral pH and stains blue under acidic pH), DRAQ5 (stains red), DRAQ7 (stains red); fluorescent non-nuclear stains, such as fluorophore-labelled phalloidin, (stains filamentous actin, color depends on conjugated fluorophore).

III.E. Morphological Staining of Samples

In certain embodiments, it may also desirable to morphologically stain a serial section of the biomarker-stained section. This section can be used to identify the ROIs from which scoring is conducted. Basic morpohological staining techniques often rely on staining nuclear structures with a first dye, and staining cytoplasmic structures with a second stain. Many morphological stains are known, including but not limited to, hematoxylin and eosin (H&E) stain and Lee's Stain (Methylene Blue and Basic Fuchsin). In a specific embodiment, at least one serial section of each biomarker-stained slide is H&E stained. Any method of applying H&E stain may be used, including manual and automated methods. In an embodiment, at least one section of the sample is an H&E stained sampled stained on an automated staining system. Automated systems for performing H&E staining typically operate on one of two staining principles: batch staining (also referred to as "dip 'n dunk") or individual slide staining. Batch stainers generally use vats or baths of reagents in which many slides are immersed at the same time. Individual slide stainers, on the other hand, apply reagent directly to each slide, and no two slides share the same aliquot of reagent. Examples of commercially available H&E stainers include the VENTANA SYMPHONY (individual slide stainer) and VENTANA HE 600 (individual slide stainer) series H&E stainers from Roche; the Dako CoverStainer (batch stainer) from Agilent Technologies; the Leica ST4020 Small Linear Stainer (batch stainer), Leica ST5020 Multistainer (batch stainer), and the Leica ST5010 Autostainer XL series (batch stainer) H&E stainers from Leica Biosystems Nussloch GmbH.

III.F. ROI Selection and Feature Metric Calculation

In an embodiment, the scoring function is applied to a feature vector derived from a digital image of one or more sections of the tumor, wherein the feature vector includes a density of CD8+ cells in a tumor core (CT) region of the tumor section.

In some embodiments, the ROI may be manually identified by a trained reader, who delineates area(s) corresponding to a CT region, which delineated regions may then be used as the ROI for calculation of the CD8+ cell density. In other embodiments, a computer-implemented system may assist the user in annotating the ROI (termed, "semi-automated ROI annotation"). For example, the user may mark a whole tumor region in the digital image. The computer-implemented system may then automatically define a region inside of the tumor region delineated by the trained user, which is then used as the ROI (in this case referred to as a tumor core (CT) ROI). See Yoon et al. (2019). In other embodiments, the computer-implemented system may automatically define a region extending a pre-defined distance (for example, 0.5 mm, 1 mm, or 1.5 mm) beyond the edge of the tumor region delineated by the trained user, which is used as the IM. In each embodiment set forth in this paragraph, the ROI may be identified directly in a biomarker-stained section, or may be identified in a serial section of the biomarker-stained section.

The feature metric is calculated by applying a metric of the ROI to the CD8+ expression data within the ROI. Examples of ROI metrics that could be used for feature metric calculation include, for example, area of the ROI or length of an edge defining the ROI (such as length of an edge of a whole tumor region around which the CT region is defined). Specific examples of feature metrics include:

(a) an area density of CD8+ cells within the ROI (number of positive cells over area of ROI), and (b) a linear density of CD8+ cells (total number of cells expressing the biomarker within the ROI over the linear length of an edge defining the ROI, such as a line denoting a tumor region around which the CT region is calculated), The feature metric may be based directly on the raw counts in the ROI (referred to hereafter as a "Total metric"), or based on a mean or median feature metric of a plurality of control regions within the ROI (hereafter referred to as a "global metric"). These two approaches are illustrated at FIG. 1. In both cases, an image of an IHC slide is provided having an ROI annotated (denoted as the region within the dashed line) and objects of interest identified (e.g., CD8+ cells). For the total metric approach, the feature metric is calculated by quantitating the relevant metric of all the marked features within the ROI ("ROI object metric") and dividing the ROI object metric (such as total marked objects or total area of marked biomarker expression, etc.) by the ROI metric (such as the area of the ROI, number of total cells within ROI, etc.) (step A1). For the global metric approach, a plurality of control regions (illustrated by the open circles) is overlaid on the ROI (step B1). A control region metric ("CR metric") is calculated by quantitating the relevant metric of the control region ("CR Object Metric") (such as total marked objects within the control region or total area of marked biomarker expression within the control region, etc.) and dividing it by a control region ROI metric ("CR ROI Metric") (such as the area of the control region, number of total cells within the control region, etc.) (step B2). A separate CR metric is calculated for each control region. The global metric is obtained by calculating the mean or the median of all CR metrics (Step B3).

Where control regions are used, any method of overlaying control regions for metric processing may be used. In a specific embodiment, the ROI may be divided into a plurality of grid spaces (which may be equal sized, randomly sized, or some combination of varying sizes), each grid space constituting a control region. Alternatively, a plurality of control regions having known sizes (which may be the same or different) may be placed adjacent to each other or overlapping one another to cover substantially the entire ROI. Other methods and arrangements may also be used, so long as the output is a feature metric for the ROI that can be compared across different samples.

If desired, the calculated feature metrics may optionally be converted to a normalized feature vector.

In the typical example, the feature metrics calculated for the samples from the subject are plotted, and the distribution is evaluated to identify any rightward or leftward skew. Biologically meaningful cutoffs (maximum cutoffs for right-skewed distributions, and/or minimum cutoffs for left-skewed distributions) are identified, and each sample having a value beyond the cutoff (above in the case of a right-skewed distribution, or below in the case of left-skewed distribution) is assigned a feature metric equal to the cutoff value. The cutoff value (hereafter referred to as the "normalization factor") is then applied to each feature metric. In the case of a right-skewed distribution, the feature metric is divided by the normalization factor to obtain the normalized feature metric, in which case the feature metric is expressed on a maximum scale (i.e. the value of the normalized metric will not exceed a pre-determined maximum, such as 1, 10, 100, etc.). Similarly, in the case of a left-skewed distribution, the feature metric is divided by the normalization factor to obtain the normalized feature metric, in which case the feature metric is expressed on a minimum scale (i.e. the value of the normalized metric will not fall below a pre-determined minimum, such as 1, 10, 100, etc.). If desired, the normalized feature metric may also be multiplied by or divided by a pre-determined constant value to obtain the desired scale (for example, for right skewed distributions, multiplied by 100 to obtain a percentage of the normalization factor instead of a fraction of the normalization factor). Normalized feature metrics may be calculated for test samples by applying the normalization factor and/or maximum and/or minimum cutoffs identified for modeling to the feature metric calculated for the test sample.

III.G. Modeling a Continuous Scoring Function

In order to generate a continuous scoring function, the feature metrics from a cohort of patients are modeled for their ability to predict the relative tumor prognosis, risk of progression, and/or likelihood of responding to a particular treatment course. In an embodiment, a "time-to-event" model is used. These models test each variable for the ability to predict the relative risk of a defined event occurring at any given time point. The "event" in such a case is typically overall survival, disease-free survival, and progression-free survival. In one example, the "time-to event" model is a Cox proportional hazard model for overall survival, disease-free survival, or progression-free survival. The Cox proportional hazard model can be written as formula 1:

$$ICS_{cox}=\exp(b^1X_1+b_2X_2+ \ldots b_pX_p) \qquad \text{Formula 1}$$

in each case, wherein $X_1$, $X_2$, . . . $X_p$ are the values of the feature metric(s) (which optionally may be subject to maximum and/or minimum cutoffs, and/or normalization), $b_1$, $b_2$ . . . $b_p$ are constants extrapolated from the model for each of the feature metric(s). For each patient sample of the test cohort, data is obtained regarding the outcome being tracked (time to death, time to recurrence, or time to progression) and the feature metric for each biomarker being analyzed. Candidate Cox proportional models are generated by entering the feature metric data and survival data for each individual of the cohort into a computerized statistical analysis software suite (such as The R Project for Statistical Computing, SAS, MATLAB, among others). Each candidate model is tested for predictive ability using a concordance index, such as C-index. The model having the highest concordance score using the selected concordance index is selected as the continuous scoring function.

Additionally, one or more stratification cutoffs may be selected to separate the patients into "risk bins" according to relative risk of non-responsiveness to immune checkpoint-directed therapy (such as "high risk" and "low risk," quartiles, deciles, etc.). In one example, stratification cutoffs are selected using receiver operating characteristic (ROC) curves. ROC curves allow users to balance the sensitivity of the model (i.e. prioritize capturing as many "positive" or "responder" candidates as possible) with the specificity of the model (i.e. minimizing false-positives for "non-responders"). In an embodiment, a cutoff between responder and non-responder bins for overall survival, disease-free survival or progression-free survival is selected, the cutoff chosen having the sensitivity and specificity balanced.

IV. Immune Context Scoring

One or more test samples from a dMMR stage IV cancer patient are stained for one or more biomarkers relevant to the scoring function (e.g., human CD8 protein) and the relevant feature metrics are calculated, and if they are being used, the normalization factor(s) and/or maximum and/or minimum cutoffs are applied to the feature metrics to obtain the normalized feature metrics (i.e., the immune context score). The immune context score may then be integrated into diagnostic and/or treatment decisions by a clinician.

IV.A. Clinical Applications of Certain Immune Context Scores

Stage IV colorectal cancers are cancers that have spread to distant organs and tissues. The present invention is developed for stage IV colorectal cancer for determining whether certain types of therapies are indicated for a specific subject.

Current treatment protocols typically include, in cases where tumor counts are low, surgical removal of the tumor and nearby lymph nodes along with surgical removal of the distant metastases, and adjuvant chemotherapy before and/or after surgical removal. For stage IV colon cancers that are not indicated for surgery, chemotherapy is typically administered as a primary treatment, optionally in combination with a targeted therapy where indicated. Some of the most commonly used regimens include: FOLFOX: leucovorin, fluorouracil (5-FU), and oxaliplatin (ELOXATIN); FOLFIRI: leucovorin, 5-FU, and irinotecan (CAMPTOSAR); CAPEOX or CAPOX: capecitabine (XELODA) and oxaliplatin; FOLFOXIRI: leucovorin, 5-FU, oxaliplatin, and irinotecan; One of the above combinations plus either a drug that targets VEGF, (bevacizumab [AVASTIN], ziv-aflibercept [ZALTRAP], or ramucirumab [CYRAMZA]), or a drug that targets EGFR (cetuximab [ERBITUX] or panitumumab [VECTIBIX]); 5-FU and leucovorin, with or without a targeted drug; Capecitabine, with or without a targeted drug; Irinotecan, with or without a targeted drug; Cetuximab alone; Panitumumab alone; Regorafenib (Stivarga) alone; Trifluridine and tipiracil (Lonsurf).

In the present invention, the scoring function is used for identifying dMMR stage IV colorectal cancer patients who are indicated for immune checkpoint-directed therapy based on the CD8+ cell densities within a tumor core.

In one embodiment, the scoring function uses a CD8+ cell density in an ROI comprising a tumor core (which density may be normalized and/or subject to maximum and/or minimum cutoffs). In an embodiment, the densities are area densities or linear densities. In an embodiment, each density is derived from a total metric or global metric.

In an embodiment, the scoring function is used as follows:

(a) for subjects with dMMR stage IV colorectal cancer having low immune context score (ICS), administering a standard therapeutic course; or (b) for subjects with dMMR stage IV colorectal cancer having a high ICS, administering a therapy course that includes an immune checkpoint-directed therapy.

In some embodiments, the ICS is based on the CD8+ cell density. In various embodiments, the cell density is measured in the tumor core.

In some embodiments, for subjects with dMMR stage IV colorectal cancer having a low ICS, immune checkpoint-directed therapy is omitted. In another embodiment, the standard therapeutic course of chemotherapy further includes treatment with an immunotherapy that is not checkpoint-directed therapy.

In some embodiments, for subjects with dMMR stage IV colorectal cancer having a high ICS, a reduced course of chemotherapy is combined with the immune checkpoint-directed therapy. A "reduced" course of chemotherapy could include a reduction in the number of different chemotherapy agents used, the dose of one or more chemotherapy agent(s), and/or the duration of treatment with the one or more chemotherapy agent(s). A reduced course of chemotherapy may also include selection of a chemotherapy agent that has a lower toxicity profile relative to other chemotherapy agents for the treatment of CRC.

Exemplary immune checkpoint-directed therapies include checkpoint inhibitors that target PD-1 (such as nivolumab, pembrolizumab, cemiplimab, tislelizumab, spartalizumab, MEDI0680 (AstraZeneca), JS001 (Shanghai Junshi Biosciences), IBI308 (Innovent Biologics), JNJ-63723283), PD-L1 (such as atezolizumab, durvalumab, avelumab), PD-L1 (such as atezolizumab, avelumab, or durvalumab), CTLA-4 (such as ipilimumab), IDO inhibitors (such as NLG919), etc. In an embodiment, the immune checkpoint-directed therapy is a PD-1-axis directed therapy. In various embodiments, the PD-1 axis directed therapy is PD-1 or a PD-L1 directed therapy.

IV.B. Immune Context Scoring Systems

In an embodiment, the scoring function as described herein is implemented by an immune context scoring system. An exemplary immune context scoring system is illustrated at FIG. 2.

The immune context scoring system includes an image analysis system 100. Image analysis system 100 may include one or more computing devices such as desktop computers, laptop computers, tablets, smartphones, servers, application-specific computing devices, or any other type(s) of electronic device(s) capable of performing the techniques and operations described herein. In some embodiments, image analysis system 100 may be implemented as a single device. In other embodiments, image analysis system 100 may be implemented as a combination of two or more devices together achieving the various functionalities discussed herein. For example, image analysis system 100 may include one or more server computers and a one or more client computers communicatively coupled to each other via one or more local-area networks and/or wide-area networks such as the Internet.

Figure 2:
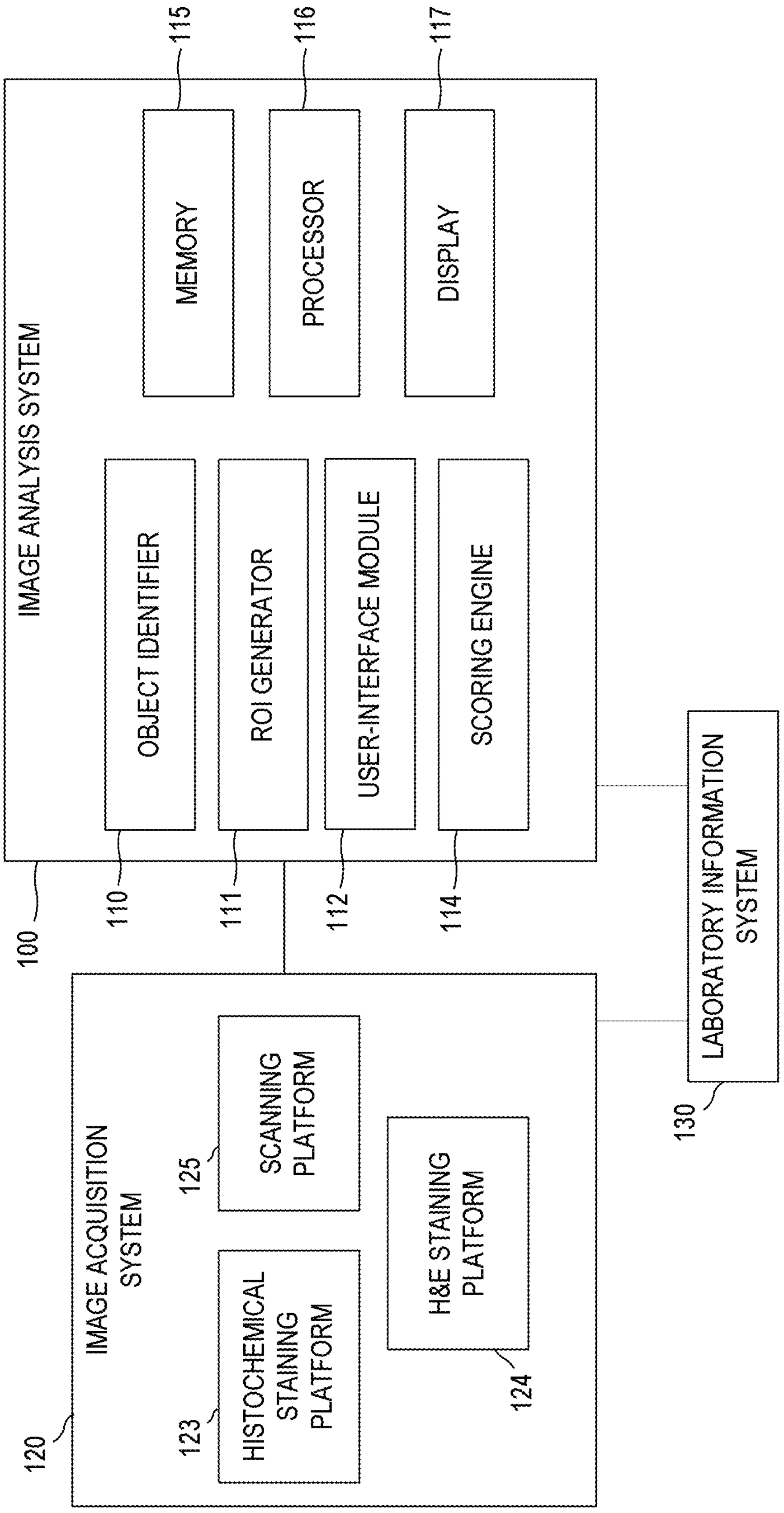
FIG. 2 illustrates an exemplary immune context scoring systems as disclosed herein.

As illustrated in FIG. 2, image analysis system 100 may include a memory 116, a processor 117, and a display 118. Memory 116 may include any combination of any type of volatile or non-volatile memories, such as random-access memories (RAMs), read-only memories such as an Electrically-Erasable Programmable Read-Only Memory (EEPROM), flash memories, hard drives, solid state drives, optical discs, and the like. For brevity purposes memory 116 is depicted in FIG. 2 as a single device, but it is appreciated that memory 116 can also be distributed across two or more devices.

Processor 117 may include one or more processors of any type, such as central processing units (CPUs), graphics processing units (GPUs), special-purpose signal or image processors, field-programmable gate arrays (FPGAs), tensor processing units (TPUs), and so forth. For brevity purposes processor 117 is depicted in FIG. 2 as a single device, but it is appreciated that processor 117 can also be distributed across any number of devices.

Display 118 may be implemented using any suitable technology, such as LCD, LED, OLED, TFT, Plasma, etc. In some implementations, display 118 may be a touch-sensitive display (a touchscreen).

As illustrated in FIG. 2, image analysis system 100 may also include an object identifier 110, a region of interest (ROI) generator 111, a user-interface module 112, and a scoring engine 114. While these modules are depicted in FIG. 2 as standalone modules, it will be evident to persons having ordinary skill in the art that each module may instead be implemented as a number of sub-modules, and that in some embodiments any two or more modules can be combined into a single module. Furthermore, in some embodiments, system 100 may include additional engines and modules (e.g., input devices, networking and communication modules, etc.) not depicted in FIG. 2 for brevity. Furthermore, in some embodiments, some of the blocks depicted in FIG. 2 may be disabled or omitted. As will be discussed in more detail below, the functionality of some or all modules of system 100 can be implemented in hardware, software, firmware, or as any combination thereof. Exemplary commercially-available software packages useful in implementing modules as disclosed herein include VENTANA VIRTUOSO; Definiens TISSUE STUDIO, DEVELOPER XD, and IMAGE MINER; and Visopharm BIOTOPIX, ONCOTOPIX, and STEREOTOPIX software packages.

After acquiring the image, image analysis system 100 may pass the image to an object identifier 110, which functions to identify and mark relevant objects and other features within the image that will later be used for scoring. Object identifier 110 may extract from (or generate for) each image a plurality of image features characterizing the various objects in the image as a well as pixels representing expression of the biomarker(s). The extracted image features may include, for example, texture features such as Haralick features, bag-of-words features and the like. The values of the plurality of image features may be combined into a high-dimensional vector, hereinafter referred to as the "feature vector" characterizing the expression of the biomarker. For example, if M features are extracted for each object and/or pixel, each object and/or pixel can be characterized by an M-dimensional feature vector. The output of object identifier 110 is effectively a map of the image annotating the position of objects and pixels of interest and associating those objects and pixels with a feature vector describing the object or pixels. The features extracted by object identifier 110 include at least features or feature vectors sufficient to distinguish CD3+ cells from CD3− cells in an image histochemically stained with a human CD3 biomarker specific reagent.

The image analysis system 100 may also pass the image to ROI generator 111. ROI generator 111 is used to identify the ROI or ROIs of the image from which the immune context score will be calculated. In cases where the object identifier 110 is not applied to the whole image, the ROI or ROIs generated by the ROI generator 111 may also be used to define a subset of the image on which object identifier 110 is executed.

In one embodiment, ROI generator 111 may be accessed through user-interface module 112. An image of the biomarker-stained sample (or a morphologically-stained serial section of the biomarker-stained sample) is displayed on a graphic user interface of the user interface module 112, and the user annotates one or more region(s) in the image to be considered ROIs. ROI annotation can take a number of forms in this example. For example, the user may manually define the ROI (referred to hereafter as "manual ROI annotation"). In other examples, the ROI generator 111 may assist the user in annotating the ROI (termed, "semi-automated ROI annotation") as described above in section III.F.

In some embodiments, ROI generator 111 may also include a registration function, whereby an ROI annotated in one section of a set of serial sections is automatically transferred to other sections of the set of serial sections. This functionality is especially useful when there are multiple biomarkers being analyzed, or when an H&E-stained serial section is provided along with the biomarker-labeled sections.

Figure 3A:
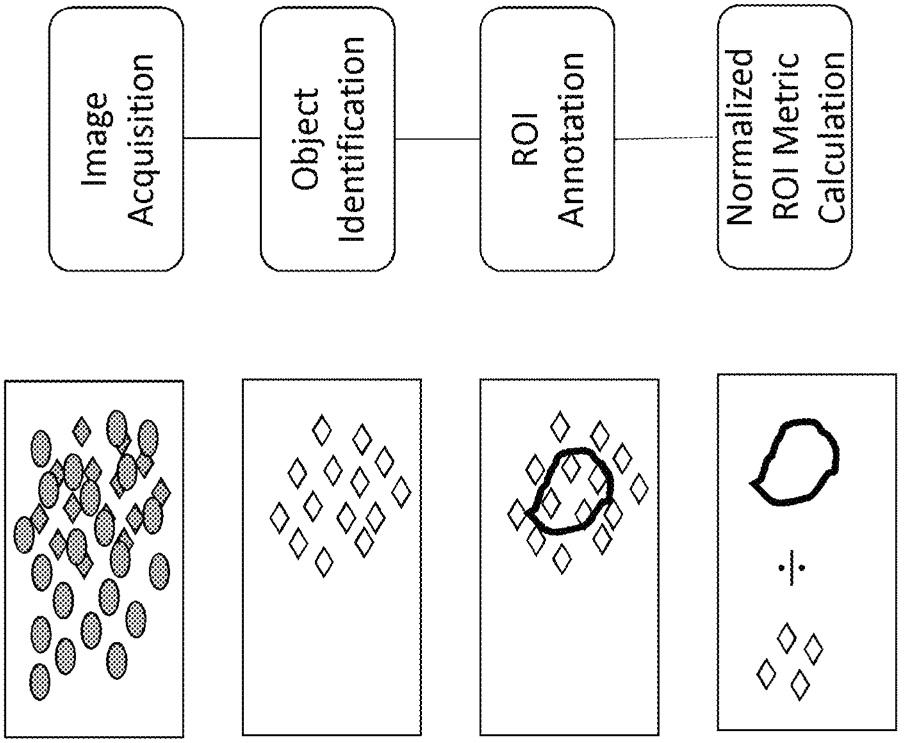
FIG. 3A illustrates an exemplary workflow implemented on an image analysis system as disclosed herein, wherein the object identification function is executed on the whole image before the ROI generator function is executed.
Figure 3B:
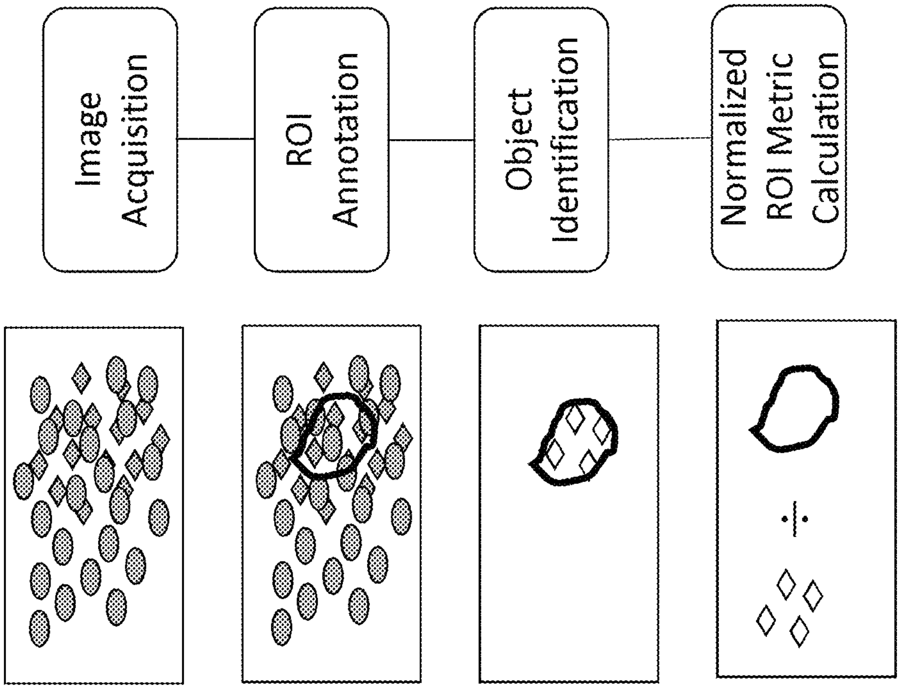
FIG. 3B illustrates an exemplary workflow implemented on an image analysis system as disclosed herein, wherein the object identification function is executed on only the ROI after the ROI generator function is executed.

The object identifier 110 and the ROI generator 111 may be implemented in any order. For example, the object identifier 110 may be applied to the entire image first. The positions and features of the identified objects can then be stored and recalled later when the ROI generator 111 is implemented. In such an arrangement, a score can be generated by the scoring engine 113 immediately upon generation of the ROI. Such a workflow is illustrated at FIG. 3A. As can be seen at FIG. 3A, an image is obtained having a mixture of different objects (illustrated by dark ovals and dark diamonds). After object identification task is implemented, all diamonds in the image are identified (illustrated by open diamonds). When the ROI is appended to the image (illustrated by the dashed line), only the diamonds located in the ROI region are included in the metric calculation for the ROI. A feature vector is then calculated including the feature metric and any additional metrics used by a non-continuous scoring function as described below. Alternatively, the ROI generator 111 can be implemented first. In this work flow, the object identifier 110 may be implemented only on the ROI (which minimizes computation time), or it may still be implemented on the whole image (which would allow on-the-fly adjustments without re-running the object identifier 110). Such a workflow is illustrated at FIG. 3B. As can be seen at FIG. 3B, an image is obtained having a mixture of different object (illustrated by dark ovals and dark diamonds). The ROI is appended to the image (illustrated by the dashed line), but no objects have been marked yet. After object identification task is implemented on the ROI, all diamonds in the ROI are identified (illustrated by open diamonds) and included in the feature metric calculation for the ROI. A feature vector is then calculated including the feature metric(s) and any additional metrics used by the non-continuous scoring function. It may also be possible to implement the object identifier 110 and ROI generator 111 simultaneously.

After both the object identifier 110 and ROI generator 111 have been implemented, a scoring engine 112 is implemented. The scoring engine 112 calculates feature metric(s) for the ROI from at least one ROI metric (such as ROI area or linear length of an ROI edge), relevant metrics for objects in the ROI (such as number CD8+ cells in the ROI), and, if being used, pre-determined maximum and/or minimum cut-offs and/or normalization factors. Where the feature metric is a global metric, the scoring engine 112 may also include a function that overlays a plurality of control regions in the ROI for calculating the CR metric.

As depicted in FIG. 2, in some embodiments image analysis system 100 may be communicatively coupled to an image acquisition system 120. Image acquisition system 120 may obtain images of samples and provide those images to image analysis system 100 for analysis and presentation to the user.

Figure 4:
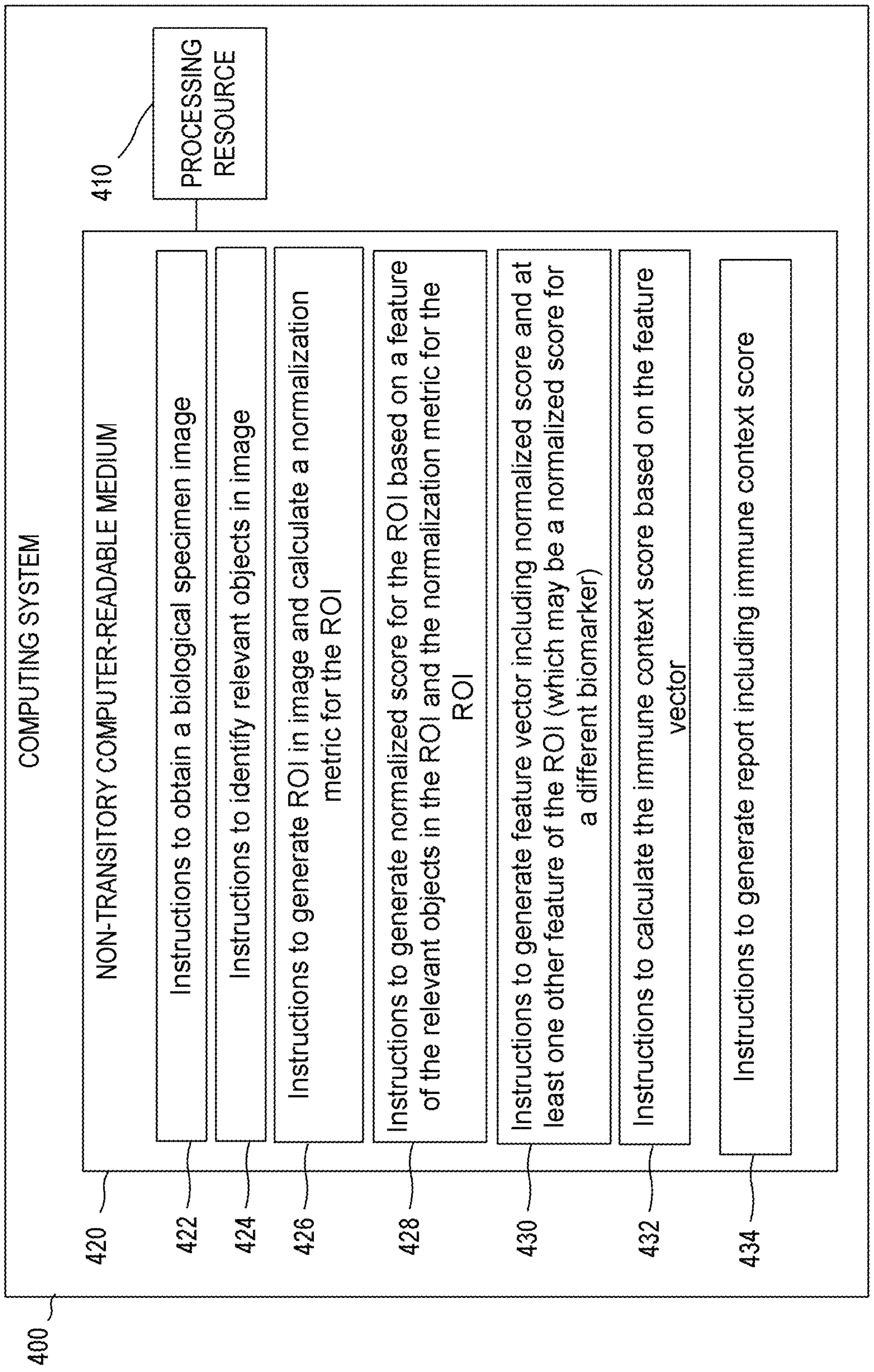
FIG. 4 illustrates an exemplary computing system that may form part of an image analysis system as disclosed herein.

As illustrated in FIG. 4, the image analysis system may include a computing system 400 for implementing the various functions, the computing system 400 comprising a processing resource 410 and a non-transitory computer readable medium 420. The non-transitory computer readable medium 420 includes, for example, instructions to execute function(s) that: obtain a biological specimen image 422; identify relevant objects in the image 424; generate an ROI in the image 426; calculate an ROI metric for the ROI 426; generate a feature metric based on the relevant objects in the ROI, the ROI metric 428, and other optional factors being used, such as normalization factors and/or maximum and/or minimum feature values; generate a feature vector including the feature metric and at least one other feature metric of the sample (which may be, for example, an additional feature metric for a different biomarker) 430; calculate immune context score based on the feature vector 432; and generate a report including the immune context score 434.

Image acquisition system 120 may also include a scanning platform 125 such as a slide scanner that can scan the stained slides at 20×, 40×, or other magnifications to produce high resolution whole-slide digital images, including for example slide scanners as discussed above at section IV. At a basic level, the typical slide scanner includes at least: (1) a microscope with lens objectives, (2) a light source (such as halogen, light emitting diode, white light, and/or multispectral light sources, depending on the dye), (3) robotics to move glass slides around (or to move the optics around the slide), (4) one or more digital cameras for image capture, (5) a computer and associated software to control the robotics and to manipulate, manage, and view digital slides. Digital data at a number of different X-Y locations (and in some cases, at multiple Z planes) on the slide are captured by the camera's charge-coupled device (CCD), and the images are joined together to form a composite image of the entire scanned surface. Common methods to accomplish this include:

(1) Tile based scanning, in which the slide stage or the optics are moved in very small increments to capture square image frames, which overlap adjacent squares to a slight degree. The captured squares are then automatically matched to one another to build the composite image; and (2) Line-based scanning, in which the slide stage moves in a single axis during acquisition to capture a number of composite image "strips." The image strips can then be matched with one another to form the larger composite image.

A detailed overview of various scanners (both fluorescent and brightfield) can be found at Farahani et al., Whole slide imaging in pathology: advantages, limitations, and emerging perspectives, Pathology and Laboratory Medicine Int'l, Vol. 7, p. 23-33 (June 2015), the content of which is incorporated by reference in its entirety. Examples of commercially available slide scanners include: 3DHistech PAN- NORAMIC SCAN II; DigiPath PATHSCOPE; Hamamatsu NANOZOOMER RS, HT, and XR; Huron TISSUESCOPE 4000, 4000XT, and HS; Leica SCANSCOPE AT, AT2, CS, FL, and SCN400; Mikroscan D2; Olympus VS120-SL; Omnyx VL4, and VL120; PerkinElmer LAMINA; Philips ULTRA-FAST SCANNER; Sakura Finetek VISIONTEK; Unic PRECICE 500, and PRECICE 600x; VENTANA ISCAN COREO and ISCAN HT; and Zeiss AXIO SCAN.Z1. Other exemplary systems and features can be found in, for example, WO2011-049608) or in U.S. Patent Application No. 61/533,114, filed on Sep. 9, 2011, entitled IMAGING SYSTEMS, CASSETTES, AND METHODS OF USING THE SAME the content of which is incorporated by reference in its entirety.

Images generated by scanning platform 125 may be transferred to image analysis system 100 or to a server or database accessible by image analysis system 100. In some embodiments, the images may be transferred automatically via one or more local-area networks and/or wide-area networks. In some embodiments, image analysis system 100 may be integrated with or included in scanning platform 125 and/or other modules of image acquisition system 120, in which case the image may be transferred to image analysis system, e.g., through a memory accessible by both platform 125 and system 120. In some embodiments, image acquisition system 120 may not be communicatively coupled to image analysis system 100, in which case the images may be stored on a non-volatile storage medium of any type (e.g., a flash drive) and downloaded from the medium to image analysis system 100 or to a server or database communicatively coupled thereto. In any of the above examples, image analysis system 100 may obtain an image of a biological sample, where the sample may have been affixed to a slide and stained by histochemical staining platform 123, and where the slide may have been scanned by a slide scanner or another type of scanning platform 125. It is appreciated, however, that in other embodiments, below-described techniques may also be applied to images of biological samples acquired and/or stained through other means.

Image acquisition system 120 may also include an automated histochemical staining platform 123, such as an automated IHC/ISH slide stainer. Automated IHC/ISH slide stainers typically include at least: reservoirs of the various reagents used in the staining protocols, a reagent dispense unit in fluid communication with the reservoir(s) for dispensing reagent to onto a slide, a waste removal system for removing used reagents and other waste from the slide, and a control system that coordinates the actions of the reagent dispense unit and waste removal system. In addition to performing staining steps, many automated slide stainers can also perform steps ancillary to staining (or are compatible with separate systems that perform such ancillary steps), including: slide baking (for adhering the sample to the slide), dewaxing (also referred to as deparaffinization), antigen retrieval, counterstaining, dehydration and clearing, and coverslipping. Prichard, *Overview of Automated Immunohistochemistry*, Arch Pathol Lab Med., Vol. 138, pp. 1578-1582 (2014), incorporated herein by reference in its entirety, describes several specific examples of automated IHC/ISH slide stainers and their various features, including the intelliPATH (Biocare Medical), WAVE (Celerus Diagnostics), DAKO OMNIS and DAKO AUTOSTAINER LINK 48 (Agilent Technologies), BENCHMARK (Ventana Medical Systems, Inc.), Leica BOND, and Lab Vision Autostainer (Thermo Scientific) automated slide stainers. Additionally, Ventana Medical Systems, Inc. is the assignee of a number of United States patents disclosing systems and methods for performing automated analyses, including U.S. Pat. Nos. 5,650,327, 5,654,200, 6,296,809, 6,352,861, 6,827,901 and 6,943,029, and U.S. Published patents application Nos. 20030211630 and 20040052685, each of which is incorporated herein by reference in its entirety. Commercially-available staining units typically operate on one of the following principles: (1) open individual slide staining, in which slides are positioned horizontally and reagents are dispensed as a puddle on the surface of the slide containing a tissue sample (such as implemented on the DAKO AUTOSTAINER Link 48 (Agilent Technologies) and intelliPATH (Biocare Medical) stainers); (2) liquid overlay technology, in which reagents are either covered with or dispensed through an inert fluid layer deposited over the sample (such as implemented on VENTANA BenchMark and DISCOVERY stainers); (3) capillary gap staining, in which the slide surface is placed in proximity to another surface (which may be another slide or a coverplate) to create a narrow gap, through which capillary forces draw up and keep liquid reagents in contact with the samples (such as the staining principles used by DAKO TECHMATE, Leica BOND, and DAKO OMNIS stainers). Some iterations of capillary gap staining do not mix the fluids in the gap (such as on the DAKO TECHMATE and the Leica BOND). In variations of capillary gap staining termed dynamic gap staining, capillary forces are used to apply sample to the slide, and then the parallel surfaces are translated relative to one another to agitate the reagents during incubation to effect reagent mixing (such as the staining principles implemented on DAKO OMNIS slide stainers (Agilent)). In translating gap staining, a translatable head is positioned over the slide. A lower surface of the head is spaced apart from the slide by a first gap sufficiently small to allow a meniscus of liquid to form from liquid on the slide during translation of the slide. A mixing extension having a lateral dimension less than the width of a slide extends from the lower surface of the translatable head to define a second gap smaller than the first gap between the mixing extension and the slide. During translation of the head, the lateral dimension of the mixing extension is sufficient to generate lateral movement in the liquid on the slide in a direction generally extending from the second gap to the first gap. See WO 2011-139978 A1. It has recently been proposed to use inkjet technology to deposit reagents on slides. See WO 2016-170008 A1. This list of staining technologies is not intended to be comprehensive, and any fully or semi-automated system for performing biomarker staining may be incorporated into the histochemical staining platform 123.

Image acquisition system 120 may also include an automated H&E staining platform 124. Automated systems for performing H&E staining typically operate on one of two staining principles: batch staining (also referred to as "dip 'n dunk") or individual slide staining. Batch stainers generally use vats or baths of reagents in which many slides are immersed at the same time. Individual slide stainers, on the other hand, apply reagent directly to each slide, and no two slides share the same aliquot of reagent. Examples of commercially available H&E stainers include the VENTANA SYMPHONY (individual slide stainer) and VENTANA HE 600 (individual slide stainer) series H&E stainers from Roche; the Dako CoverStainer (batch stainer) from Agilent Technologies; the Leica ST4020 Small Linear Stainer (batch stainer), Leica ST5020 Multistainer (batch stainer), and the Leica ST5010 Autostainer XL series (batch stainer) H&E stainers from Leica Biosystems Nussloch GmbH. H&E staining platform 124 is typically used in workflows in which a morphologically-stained serial section of the biomarker-stained section(s) is desired.

The immune context scoring system may further include a laboratory information system (LIS) 130. LIS 130 typically performs one or more functions selected from: recording and tracking processes performed on samples and on slides and images derived from the samples, instructing different components of the immune context scoring system to perform specific processes on the samples, slides, and/or images, and track information about specific reagents applied to samples and or slides (such as lot numbers, expiration dates, volumes dispensed, etc.). LIS 130 usually comprises at least a database containing information about samples; labels associated with samples, slides, and/or image files (such as barcodes (including 1-dimensional barcodes and 2-dimensional barcodes), radio frequency identification (RFID) tags, alpha-numeric codes affixed to the sample, and the like); and a communication device that reads the label on the sample or slide and/or communicates information about the slide between the LIS 130 and the other components of the immune context scoring system. Thus, for example, a communication device could be placed at each of a sample processing station, automated histochemical stainer 123, H&E staining platform 124, and scanning platform 125. When the sample is initially processed into sections, information about the sample (such as patient ID, sample type, processes to be performed on the section(s)) may be entered into the communication device, and a label is created for each section generated from the sample. At each subsequent station, the label is entered into the communication device (such as by scanning a barcode or RFID tag or by manually entering the alpha-numeric code), and the station electronically communicates with the database to, for example, instruct the station or station operator to perform a specific process on the section and/or to record processes being performed on the section. At scanning platform 125, the scanning platform 125 may also encode each image with a computer-readable label or code that correlates back to the section or sample from which the image is derived, such that when the image is sent to the image analysis system 100, image processing steps to be performed may be sent from the database of LIS 130 to the image analysis system and/or image processing steps performed on the image by image analysis system 100 are recorded by database of LIS 130. Commercially available LIS systems useful in the present methods and systems include, for example, VENTANA Vantage Workflow system (Roche).

V. In View of the Above, the Following Embodiments are Particularly Envisaged Embodiment 1. A method of treating a subject having a stage IV colorectal cancer, said method comprising:

(a) obtaining an immune context score (ICS) from a tissue sample collected from a colorectal tumor of the subject by:

(i) identifying a tumor core (CT) region of interest (ROI) of a test sample of a tumor from said subject;

(ii) detecting $CD8^+$ cells in at least a portion of the ROI; and (iii) obtaining a $CD8^+$ cell density within the ROI to calculate the ICS; and (b) selecting a treatment for the subject based upon the ICS.

Embodiment 2. The method of embodiment 1, wherein said stage IV colorectal cancer has been diagnosed as having deficient DNA mismatch repair and/or microsatellite instability (MSI).

Embodiment 3. The method of embodiment 1 or 2, wherein:

(b1) if the ICS is low, selecting a treatment comprising a full course of adjuvant chemotherapy and optionally a checkpoint inhibitor-directed therapy; and (b2) if the ICS is high, selecting a treatment comprising a checkpoint inhibitor-directed therapy and optionally a reduced course of an adjuvant chemotherapy.

Embodiment 4. The method of embodiment 3, wherein (b2) comprises no adjuvant chemotherapy.

Embodiment 5. The method of embodiment 3, wherein the optional adjuvant chemotherapy of (b2) is reduced in duration, dose, or toxicity relative to a chemotherapy regimen in the absence of checkpoint inhibitor-directed therapy.

Embodiment 6. The method of embodiment 3, wherein the checkpoint inhibitor-directed therapy comprises a PD-1-axis directed therapy.

Embodiment 7. The method of any of embodiment 3, wherein the checkpoint inhibitor-directed therapy comprises a PD-1 or PD-L1-directed therapy.

Embodiment 8. The method of embodiments 6 or 7, wherein the checkpoint inhibitor-directed therapy is selected from nivolumab, pembrolizumab, cemiplimab, tislelizumab, spartalizumab, MEDI0680, JS001, IBI308, JNJ-63723283, atezolizumab, durvalumab, and avelumab.

Embodiment 9. The method of embodiment 1, wherein the CD8+ cell density is an area cell density obtained by dividing the quantity of the detected cells in the ROI by the area of the ROI.

Embodiment 10. The method of embodiment 1, wherein the CD8+ cell density is derived from a mean or median area cell density of a plurality of control regions of the ROI.

Embodiment 11. The method of any of embodiments 1-10, wherein step (a) (ii) further comprises detecting $CD3^+$ cells in at least a portion of the ROI and wherein the ICS is calculated based on the combination of the CD8+ cell density and the CD3+ cell density.

Embodiment 12. The method any of embodiments 1-10, wherein:

the ROI is annotated on a digital image of a first serial section of the sample, the first serial section being stained with hematoxylin and eosin (H&E); and the calculation of (a) comprises:

registering the first ROI to a digital image of a second serial section of the sample, the second serial section being histochemically stained for human CD8; and calculating the density of human CD8+ cells from the ROI registered to the digital image of the second serial section.

Embodiment 13. The method of embodiment 12, wherein the calculation of (a) further comprises:

registering the first ROI to a digital image of a third serial section of the sample, the third serial section being histochemically stained for human CD3; and calculating the density of human CD3+ cells from the ROI registered to the digital image of the third serial section.

Embodiment 14. The method of embodiments 12 or 13, wherein multiple ROIs are annotated, wherein at least one ROI includes a portion of a CT region and a separate ROI includes a portion of the IM region.

Embodiment 15. A computer-implemented method comprising causing a computer processor to execute a set of computer-executable functions stored on a memory, the set of computer-executable functions comprising:

(a) obtaining a digital image of at least one tissue section of a stage IV colorectal tumor; and (b) executing on the digital image a method of any of embodiments 1-14.

Embodiment 16. A system for scoring an immune context of a tissue sample, the system comprising:

(a) a processor; and (b) a memory coupled to the processor, the memory to store computer-executable instructions that, when executed by the processor, cause the processor to perform operations comprising the method of any of embodiments 1-14.

Embodiment 17. The system of embodiment 16, further comprising a scanner or microscope adapted to capture a digital image of a section of the tissue sample and to communicate the image to the computer apparatus.

Embodiment 18. The system of embodiments 16 or 17, further comprising an automated slide stainer programmed to histochemically stain one or more sections of the tissue sample for the CD8 and the CD3 markers.

Embodiment 19. The system of embodiment 18, further comprising an automated hematoxylin and eosin stainer programmed to stain one or more serial sections of the sections stained by the automated slide stainer.

Embodiment 20. The system of any of embodiments 16-19, further comprising a laboratory information system (LIS) for tracking sample and image workflow, the LIS comprising a central database configured to receive and store information related to the tissue sample, the information comprising at least one of the following:

(a) processing steps to be carried out on the tumor tissue sample, (b) processing steps to be carried out on digital images of sections of the tumor tissue sample, and (c) processing history of the tumor tissue sample and digital images.

Embodiment 21. A non-transitory computer readable storage medium for storing computer-executable instructions that are executed by a processor to perform operations, the operations comprising the method of any of embodiments 1-14.

Embodiment 22. A method for obtaining an immune context score (ICS) from a tissue sample collected from a stage IV colorectal tumor comprising (i) identifying a tumor core (CT) region of interest (ROI) of said tissue sample;

(ii) detecting CD8+ cells in at least a portion of the ROI; and iii) obtaining a density of CD8+ cells within the ROI to calculate the ICS.

Embodiment 23. A computer-implemented method comprising causing a computer processor to execute a set of computer-executable functions stored on a memory, the set of computer-executable functions comprising:

(A) obtaining a digital image of a tissue section of a stage IV colorectal tumor, wherein the tissue section is histochemically stained for at least human CD8;

(B) annotating one or more regions of interest (ROI) in the digital image, the ROI comprising a tumor core (CT); and (C) applying a scoring function to the ROI, wherein the scoring function comprises calculating a feature vector comprising a density of CD8+ cells in the CT to obtain an immune context score for the tissue section.

Embodiment 24. A method comprising:

(a) annotating a one or more region(s) of interest (ROI) on a digital image of a tumor tissue section, wherein at least one of the ROIs includes at least a portion of a tumor core (CT) region;

(b) detecting and quantitating cells expressing human CD8 in the ROI;

(c) calculating a density of CD8+ cells within the ROI, and optionally normalizing the CD8+ cell density or tumor-infiltrating lymphocyte (TIL) cell density to the feature vector to obtain an immune context score (ICS) for the tumor.

Embodiment 25. The method of any one of embodiments 22 to 24, wherein step (i) is preceded by labeling a tissue section of said tissue sample with a human CD8 protein biomarker-specific reagent in combination with appropriate detection reagents.

Embodiment 26. A method for obtaining an immune context score (ICS) from a human tissue sample collected from a stage IV colorectal tumor comprising (i) labeling a tissue section of said tissue sample with a human CD8 protein biomarker-specific reagent in combination with appropriate detection reagents;

(ii) identifying a tumor core (CT) region of interest (ROI) of said tissue sample;

(iii) detecting CD8+ cells in at least a portion of the ROI; and (iv) obtaining a density of CD8+ cells within the ROI to calculate the ICS.

Embodiment 27. The method of any one of embodiments 22 to 26, wherein said density of CD8+ cells is an area density or a linear density.

Embodiment 28. The method of any one of embodiments 22 to 27, wherein said ICS corresponds to, in an embodiment is, a normalized CD8+ cell density within the ROI, in an embodiment is the normalized CD8+ cell density within the ROI after application of one or more normalization factor(s), maximum cutoff and/or minimum cutoff.

Embodiment 29. The method of any one of embodiments 22 to 28, wherein said ICS is used for determining whether an immune checkpoint-directed therapy is indicated.

Embodiment 30. The method of any one of embodiments 22 to 29, wherein said method further comprises detecting CD3+ cells and obtaining a CD3+ cell density within the ROI, and wherein optionally the ICS is calculated based on the combination of the CD8+ cell density and the CD3+ cell density.

Embodiment 31. The method of any one of embodiments 22 to 30, wherein said method further comprises determining DNA mismatch repair (MMR) status.

Embodiment 32. The method of any one of embodiments 22 to 31, wherein said determining MMR status comprises determining expression and/or methylation status the hPMS2 gene, the hMLH1 gene, the hMSH2 gene, and the hMSH6 gene.

Embodiment 33. The method of embodiment 31 or 32, wherein a tissue sample having deficient expression of any one of the genes as specified in embodiment 32 is determined to have deficient MMR.

Embodiment 34. The method of any one of embodiments 31 to 33, wherein said determining MMR status comprises determining expression by a protein-based assay, in an embodiment an immunoassay, in a further embodiment a solid-phase enzyme immunoassay or immunohistochemical assay; or by a polymerase chain reaction (PCR) assay, in an embodiment a real-time reverse transcriptase PCR assay.

Embodiment 35. The method of any one of embodiments 22 to 35, wherein said method further comprises determining microsatellite instability (MSI).

Embodiment 36. The method of any one of embodiments 22 to 35, wherein the ROI is identified manually, semi-automatically, or automatically, in an embodiment is identified automatically.

Embodiment 37. A method for determining whether an immune checkpoint-directed therapy is indicated for a patient suffering from a stage IV colorectal cancer with defective mismatch repair (dMMR), comprising obtaining an immune context score (ICS) according to a method according to any one of embodiments 22 to 36, and determining that an immune checkpoint-directed therapy is indicated in case a high ICS is determined.

Embodiment 38. A checkpoint inhibitor for use in treating a subject with defective DNA mismatch repair (dMMR) stage IV colorectal cancer, wherein said subject has a high immune context score (ICS), in an embodiment determined according to a method according to any one of embodiments 22 to 36.

Embodiment 39. The checkpoint inhibitor for use of embodiment 38, wherein said treatment comprises reduced course of chemotherapy in combination with said immune checkpoint-directed therapy.

Embodiment 40. The checkpoint inhibitor for use of embodiment 39, wherein said reduced course of chemotherapy is a reduction in the number of different chemotherapy agents used, of the dose of one or more chemotherapy agent(s), and/or of the duration of treatment with the one or more chemotherapy agent(s); and/or comprises selection of a chemotherapy agent that has a lower toxicity profile relative to other chemotherapy agents for the treatment of stage IV colorectal cancer.

Embodiment 41. The subject matter of any one of embodiments 37 to 40, wherein said checkpoint inhibitor is a checkpoint inhibitor targeting PD-1, PD-L1, CTLA-4, or IDO, in an embodiment is a checkpoint inhibitor targeting PD-1 or PD-L1.

Embodiment 42. The subject matter of any one of embodiments 37 to 41, wherein said checkpoint inhibitor is pembrolizumab, nivolumab, cemiplimab, tislelizumab, spartalizumab, MEDI0680, JS001, IBI308, JNJ-63723283, atezolizumab, durvalumab, avelumab, ipilimumab, or NLG919, in an embodiment is pembrolizumab, nivolumab, cemiplimab, tislelizumab, spartalizumab, MEDI0680, JS001, IBI308, JNJ-63723283, atezolizumab, durvalumab, or avelumab, in a further embodiment is pembrolizumab.

Embodiment 43. A system for scoring an immune context of a tumor tissue sample, the system including at least a computer processor and a memory, wherein the memory stores a set of computer executable instructions to be executed by the computer processor, the set of computer executable instructions including a method according to any of the previous embodiments referring to a method.

VI. Experimental Examples

VI.A. Patients and Methods

Twelve patients with dMMR metastatic colorectal cancer (mCRC) who were treated with pembrolizumab (at a dose of 10 mg/Kg intravenously every 3 weeks) were identified. Electronic medical records were reviewed to obtain information on patient and tumor characteristics, MMR test results, KRAS and BRAF status, prior treatment regimens, and pembrolizumab treatment response data (best response, time to best response, number of cycles, duration of disease control). Tumor response was assessed using National Cancer Institute response evaluation criteria in solid tumors (RECIST) version 1.1 criteria. See Eisenhauer et al. (2009).

DNA mismatch repair (MMR) status had been analyzed in tumor tissue by immunohistochemistry (IHC) for MMR proteins (MLH1, MSH2, MSH6, PMS2) or using a PCR-based assay for microsatellite instability (MSI), as previously described. See Sinicrope et al. (2013). In formalin-fixed and paraffin-embedded tumor tissues, CD3+ and CD8+ T lymphocyte staining was performed by immunohistochemical analysis (VENTANA BenchMark ULTRA autostainer; Ventana Medical Systems, Inc.).

Briefly, H&E-stained sections along with the immunostained slides were scanned. Independent pathologists manually annotated H&E sections to outline the entire tumor region containing invasive cancer (i.e., core of the tumor; CT) using a whole-tumor section approach. They further demarcated the invasive margin (IM) without knowledge of clinical characteristics or outcome by indicating sections of the tumor outline involved in the invasive process. A registration algorithm (Sarkar et al. 2014) automatically transferred pathologist-derived annotations from the H&E onto the adjacent CD3 and CD8 IHC images.

From the IM demarcation, an algorithm automatically generated the IM area as 0.5 mm extending into the tumor core and 1.0 mm beyond the tumor. Fully automated computer vision and cell classification (Lorsakul et al. 2018) captured CD3-positive and CD8-positive cells in the CT and IM areas with algorithm parameters fixed for all slides in the study. Multiple quality steps were employed to ensure fidelity of tissue slides, digital images, registration, and cell detection. Digital image analysis reports the tissue area and number of detected T cells in the two observed compartments. CD3+ and CD8+ TIL densities at the IM and CT were quantified by image analysis and normalized to establish semi-continuous density scores (0-100 scale).

TIL analysis was performed blinded to patient outcomes. Calculation of semicontinuous density scores (0-100 scale) CD3 and CD8 counts were determined at the tumor core and invasive margin. The density of each marker (CD3+IM, CD3+CT, CD8+IM, CD8+CT) was calculated by dividing the count by the area of its tumor compartment. Given the potential right-skew in density distributions, biologically meaningful maximum values were established by truncating large densities, as follows: (i), Density values were categorized starting from zero in incremental steps of 250 cells/$mm^2$; (ii), Patients with the highest density values were identified ("edge effect" group); (iii), The density value that represented the cutoff value for the "edge effect" group was identified; (iv), The incremental step corresponding to the "edge effect" cutoff value was established as the truncation value. Densities larger than this truncation value were assigned the truncation value. Density values were then standardized to generate a Density Score ranging from 0 to 100:

$$\text{Density score} = \frac{\text{Density} * 100}{\text{truncation value}}$$

MMR tumor status was determined by immunohistochemical analysis (IHC) or by MSI testing when IHC findings were indeterminate, as previously described (Sinicrope et al. 2013). Tumors with a dMMR phenotype were defined as showing loss of expression of 1 or more MMR proteins by IHC or exhibiting high-level tumor DNA MSI on MSI testing by polymerase chain reaction (PCR). Tumor DNA was extracted from formalin-fixed, paraffin embedded tissue specimens containing more than 50% tumor cells using the QIAamp DNA Mini Kit (Qiagen).

For comparisons of baseline characteristics, categorical factors were analyzed with $\chi^2$ tests, and continuous factors were compared with Wilcoxon rank-sum tests. For each T-cell subtype, densities between tumor compartments were compared using median pairwise differences (Wilcoxon Sign Rank tests). A Cox regression model was used to estimate hazard ratios (HR) and 95% confidence intervals (CI) and to calculate P values. Analyses were conducted in each MMR group separately. Each immune variable (CD3+ IM, CD3+CT, CD8+IM, and CD8+CT) was analyzed as a continuous variable with regard to overall survival (OS) in univariate and multivariable analysis. Covariates were pre-specified as T3 or T4 (vs. T1-2),N2 (vs. N1), grade high (vs. low), tumor side left (vs. right), smoking ever (vs. never), and age for each 5 years increase. No interactions were observed in adjusted analysis between any two of the immune markers on OS in either MMR group. Any individual immune variable demonstrating an association with OS at P<0.10 adjusting for common clinicopathological features was then included in a backward selection model. For immune variables with a statistically significant association with OS after backward selection, an optimal cutoff point that distinguished OS was identified using Cox Model Hazard Ratio and Wald P value methods. OS was defined as the time between randomization and any-cause death. Time to recurrence (TTR; i.e., time between randomization and local or metastatic tumor recurrence) was analyzed as a secondary endpoint. Two-sided P values are reported; P<0.05 was considered statistically significant. Analyses were performed using SAS software (v9.4, SAS Institute Inc.).

VI.B. Results

Patient and tumor characteristics, details of prior treatment, and pembrolizumab response data are summarized in Table 1. Median number of prior chemotherapy regimens received was 1 (range 1-4, one in 7 patients, 2 in 3 patients and 4 in 2 patients). Median follow-up of the study cohort since initiation of pembrolizumab was 19.5 months (range 9-41). Patient radiographic response data, determined by RECIST version 1.1, were as follows: 2 complete responses (CR), 5 partial responses (PR), 4 stable diseases (SD) and 1 progressive disease (PD). The objective response rate was 58.3% (7/12). Among pembrolizumab-treated patients who had a CR or PR (n=7), median time to response was 12 weeks (range 9-20).

TABLE 1

Patient characteristics, treatment and response data in dMMR metastatic colorectal cancer patients

| Age/Sex | Primary tumor site | RAS/BRAF status | MMR protein loss | No. of prior regimens | Best response | Time to best response (weeks) | Number of Anti-PD-1 cycles | Duration of disease control (months) |
|---|---|---|---|---|---|---|---|---|
| 59/M | Sigmoid | RAS WT/ BRAF$^{V600E}$ | MLH1, PMS2 | 1 | SD | 6 | 15 | 16 |
| 30/M | Sigmoid | Both WT | MSH2, MSH6 | 1 | PR | 20 | 15 | 13, ongoing[a] |
| 85/F | Hepatic flexure | UNK | MSI-H* | 1 | PR | 9 | 12 | 9 |
| 66/M | Transverse colon | Both WT | MLH1, PMS2 | 2 | PR | 16 | 19 | 11 |
| 76/F | Hepatic flexure | Both WT | MLH1, PMS2 | 1 | SD | 20 | 15 | 16, ongoing |
| 42/F | Cecum | Both WT | MLH1, PMS2 | 4 | SD | 12 | 7 | 5 |
| 62/M | Sigmoid | KRAS MUT, BRAF WT | MLH1, PMS2 | 4 | PD | 11 | 4 | 0 |
| 49/M | Ascending colon | Both WT | MLH1, PMS2 | 2 | CR | 9 | 31 | 27, ongoing[b] |
| 73/F | Sigmoid | Both WT | MLH1, PMS2 | 1 | PR | 12 | 20 | 16, ongoing |
| 54/F | Ascending colon | Both WT | MLH1, PMS2 | 2 | CR | 40 | 28 | 41, ongoing[c] |
| 75/F | Ascending colon | RAS WT/ BRAF$^{V600E}$ | MLH1, PMS2 | 1 | SD | 11 | 33 | 23, ongoing |
| 61/M | Splenic flexure | Both WT | MLH1, PMS2 | 1 | PR | 16 | 27 | 21, ongoing[d] |

Abbreviations: M, male; F, female; dMMR, deficient DNA mismatch repair; PR, partial response; CR, complete response; PD, progressive disease; SD, stable disease; WT, wild type; MT, mutant; anti-PD-1 (pembrolizumab) given at the dose of 10 mg/Kg every 3 weeks. UNK, unknown.

[a]Primary and liver metastasis resected following 6 months of Pembrolizumab. Had pathological CR in liver.

[b]Pembrolizumab discontinued after 2 years of therapy.

[c]PR after 12 weeks, converted to CR at 40 weeks. Pembrolizumab discontinued after 2 years of therapy.

[d]Resection of liver metastases after 1 year of pembrolizumab with pathological CR in liver.

*Determined by a PCR-based test

Figure 5:
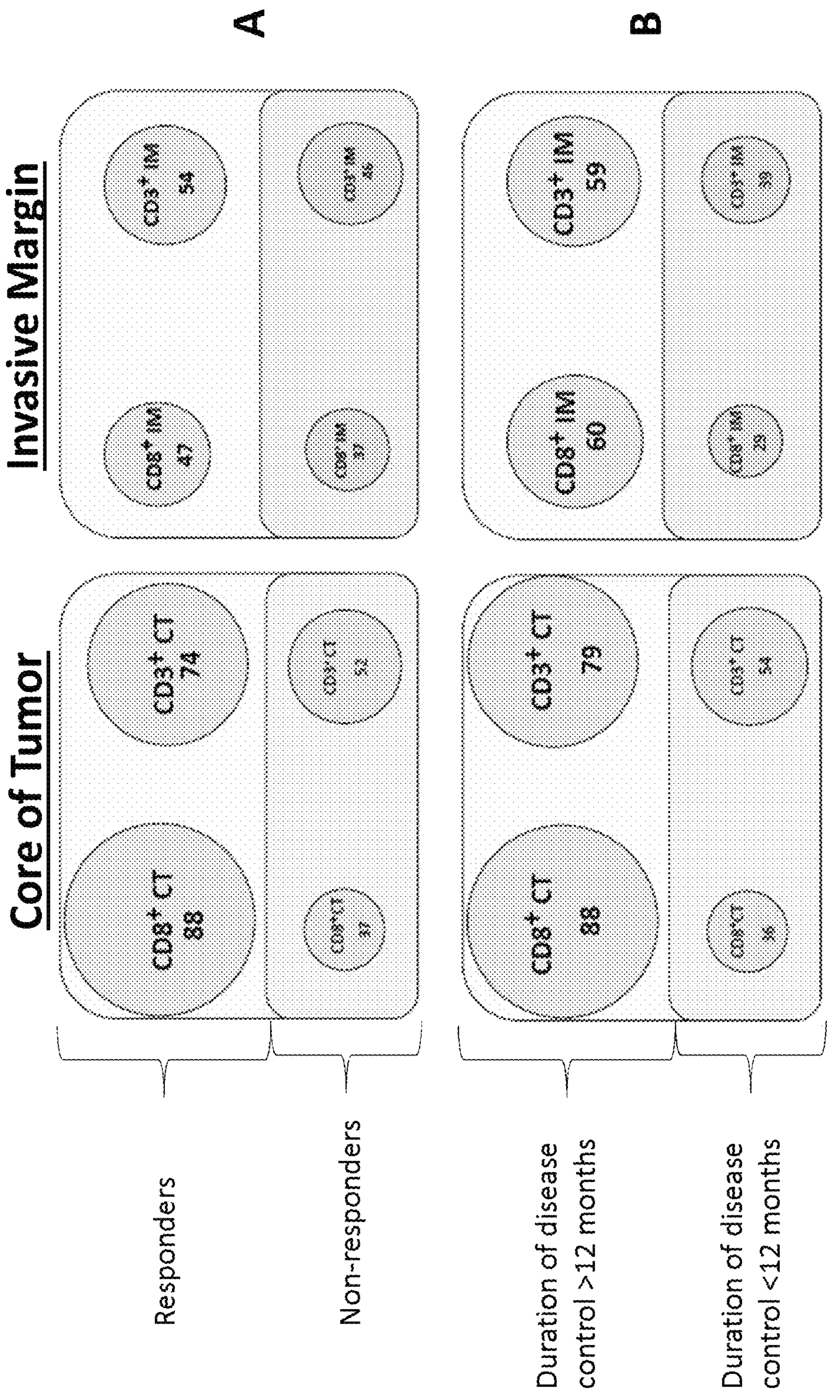
FIG. 5 depicts the distribution of CD8+ and CD3+ T-cell density (score 0-100) at the core of tumor (CT) and invasive margin (IM) among the (A) responders (top panel) and non-responders (bottom panel), and (B) among the patients with duration of disease control for more than 12 months (top panel) and less than 12 months (bottom panel). The median density of each T-cell subtype is reflected by the size of the circles within which are their density scores. Responders represent patients with complete and partial responses; non-responders represent patients with stable disease and progressive disease.

To examine the relationship between T-cell density scores and treatment response, patients were divided into responders (CR and PR, n=7) versus non-responders (SD and PD, n=5) to pembrolizumab. Median values and range of CD3+ and CD8+ T-cell density scores at the invasive margin (CD3+ IM, CD8+ IM) and the tumor core (CD3+ CT, CD8+ CT) in each response category are shown in FIG. 5A and Table 2. All median T-cell density scores were higher in responders (R) than in non-responders (NR) with differences that were greatest for CD3+ CT (74 vs 52) and CD8+ CT (88 vs 37), as shown in FIG. 5A. Analysis based on the duration of disease control was performed by dividing patients into two groups: a group with disease control for more than 12 months; and a group with disease control with less than 12 months. Median and range of density scores for T-cell markers based on duration of disease control are shown in FIG. 5B and Table 2. All median T-cell density scores were higher in the patient group where disease control was achieved for more than 12 months, with the greatest difference seen for CD8+ CT (88 vs 36) (FIG. 5B).

TABLE 2

CD3+ and CD8+ density scores at the invasive margin (IM) and the tumor core (CT) in responders and non-responders and by duration of disease control

| | Responders (CR + PR), n = 7 | Non-responders (SD + PD), n = 5 | Disease control, >12 months n = 8 | Disease control, <12 months n = 4 |
|---|---|---|---|---|
| CD3 IM, median (range) | 54 (15-100) | 46 (9-96) | 59 (9-96) | 39 (18-51) |
| CD3 CT, median (range) | 74 (34-98) | 52 (7-100) | 79 (8-98) | 54 (34-83) |
| CD8 IM, median (range) | 47 (13-89) | 37 (11-83) | 60 (11-89) | 29 (15-54) |
| CD8 CT, median (range) | 88 (31-100) | 37 (10-94) | 88 (10-100) | 36 (31-66) |
| PD-L1 (%, tumor cells) median (range) | 2 (1-40) | 1 (0-60) | 2 (1-60) | 1.5 (0-10) |
| PD-L1 (immune cells) median (range) | 5 (2-25) | 5 (1-10) | 5 (1-25) | 7.5 (3-10) |

Median PD-L1 expression on tumor cells was 2% (range, 1-40) and 1% (range, 0-60) among the responders and non-responders, respectively. Median PD-L1 expression in the intra-tumoral immune cells was similar at 5% among responders (range, 2-25) and non-responders (range 1-10).

In summary, there were higher CD3+ and CD8+ T-cell densities in dMMR tumors from patients with mCRC who were responders versus non-responders to pembrolizumab. These data suggest a potential association of dichotomized T-cell marker densities with tumor responsiveness that could explain, in part, differential responsiveness to anti-PD-1 antibodies in dMMR mCRCs.

REFERENCES

1. Anitei et al., Prognostic and Predictive Values of the Immunoscore in Patients with Rectal Cancer, Clinical Cancer Res., Vol. 20, Issue 7, pp. 1891-1899 (2014).
2. Chen & Srinivas, Automatic Lymphocyte Detection in H&E Images with Deep Neural Networks, arXiv: 1612.03217v1 (submitted 9 Dec. 2016).
3 Forrest et al., Comparison of visual and automated assessment of tumour inflammatory infiltrates in patients with colorectal cancer, European J. Cancer, Vol. 50, Issue 3, pp. 544-552 (2014).
4. Galon et al., Towards the introduction of the 'Immunoscore' in the classification of malignant tumours, J. Pathol., Vol. 232, Issue 2, pp. 199-209 (2014).
5. Galon et al., Validation of the Immunoscore (IM) as a prognostic marker in stage I/II/III colon cancer: Results of a worldwide consortium-based analysis of 1,336 patients., J. Clin. Oncol., Vol. 34, suppl. Abstract No. 3500 (2016).
6. Galon et al., Validation of the Immunoscore (IM) as a prognostic marker in stage I/II/III colon cancer: Results of a worldwide consortium-based analysis of 1,336 patients. Powerpoint presentation (2016).
7. Jass, Lymphocytic infiltration and survival in rectal cancer, J. Clin. Pathol., Vol. 39, Issue 6, pp. 585-589 (1986).
8. Jass et al., A new prognostic classification of rectal cancer, The Lancet, Vol. 329, Issue 8545, pp. 1303-1306 (1987).
9. Mei et al., Tumour-infiltrating inflammation and prognosis in colorectal cancer: systematic review and meta-analysis, British J. Cancer, Vol. 110, pp. 11595-1605 (2014).
10. Pages et al., Immune infiltration in human tumors: a prognostic factor that should not be ignored, Oncogene, Vol. 29, pp. 1093-1102 (2010).
11. Zou W, Wolchok J D, Chen L. PD-L1 (B7-H1) and PD-1 pathway blockade for cancer therapy: Mechanisms, response biomarkers, and combinations. Sci Transl Med. 2016; 8(328):328rv324.
12. Llosa N J, Cruise M, Tam A, et al. The vigorous immune microenvironment of microsatellite instable colon cancer is balanced by multiple counter-inhibitory checkpoints. Cancer discovery. 2015; 5(1):43-51.
13. Le D T, Durham J N, Smith K N, et al. Mismatch repair deficiency predicts response of solid tumors to PD-1 blockade. Science. 2017; 357(6349):409-413.
14. Pages F, Mlecnik B, Marliot F, et al. International validation of the consensus Immunoscore for the classification of colon cancer: a prognostic and accuracy study. The Lancet. 2018; 391(10135):2128-2139.
15. Yoon H H, Shi Q, Heying E N, et al. Inter-tumoral heterogeneity of CD3 (+) and CD8 (+) T-cell densities in the microenvironment of DNA mismatch repair-deficient colon cancers: implications for prognosis. Clin Cancer Res. 2019; 25(1):125-133.
16. Eisenhauer E A, Therasse P, Bogaerts J, et al. New response evaluation criteria in solid tumours: revised RECIST guideline (version 1.1). Eur J Cancer. 2009; 45(2):228-247.
17. Sinicrope F A, Mahoney M R, Smyrk T C, et al. Prognostic impact of deficient DNA mismatch repair in patients with stage III colon cancer from a randomized trial of FOLFOX-based adjuvant chemotherapy. J Clin Oncol. 2013; 31(29):3664-3672.
18. El Jabbour T, Ross J S, Sheehan C E, et al. PD-L1 protein expression in tumour cells and immune cells in mismatch repair protein-deficient and -proficient colorectal cancer: the foundation study using the SP142 antibody and whole section immunohistochemistry. J Clin Pathol. 2018; 71(1):46-51.

19. Sarkar A, Yuan Q, Srinivas C. A robust method for inter-marker whole slide registration of digital pathology images using lines based features. IEEE 11th International Symposium on Biomedical Imaging (ISBI)2014:762-5

20. Lorsakul A, Bredno J, Ochs R L, Morrison L, Day W. Validation of multiplex immunohistochemistry assays using automated image analysis. Int Soc Optics Photonics Med Imaging 2018; Digital Pathology: doi: 10.1117/12.2293168

The invention claimed is:

1. A method for calculating an immune context score (ICS) from a human tissue sample collected from a stage IV colorectal tumor previously diagnosed as having deficient DNA mismatch repair, the method comprising:

(i) labeling a first serial section of the human tissue sample collected from the stage IV colorectal tumor previously diagnosed as having deficient DNA mismatch repair with a human CD8 protein biomarker-specific reagent in combination with appropriate detection reagents;

(ii) annotating a tumor core (CT) region of interest (ROI) in a digital image of a second serial section of the human tissue sample, wherein the second serial section is stained with hematoxylin and eosin, and wherein the annotated ROI is automatically registered to a digital image of at least the first serial section of the human tissue sample;

(iii) detecting CD8+ cells in at least a portion of the ROI in the digital image of the at least the first serial section of the human tissue sample;

(iv) obtaining a CD8+ cell density within the ROI, wherein the CD8+ cell density is an area cell density obtained by dividing a quantity of the detected CD8+ cells in the ROI by the area of the ROI; and (v) applying a non-continuous scoring function to a feature vector comprising the obtained CD8+ cell density, wherein the non-continuous scoring function assigns the obtained CD8+ cell density to a pre-determined bin and calculates the ICS for the human tissue sample based on the assigned bin.

2. The method of claim 1, further comprising determining whether an immune checkpoint-directed therapy is indicated based on the calculated ICS.

3. The method of claim 1, wherein said method further comprises detecting CD3+ cells and obtaining a CD3+ cell density within the ROI, and wherein optionally the ICS is calculated based on the combination of the CD8+ cell density and the CD3+ cell density.

4. The method of claim 1, wherein said method further comprises determining microsatellite instability (MSI).

5. The method of claim 1, wherein the ROI is annotated manually, semi-automatically, or automatically, in an embodiment is identified automatically.

6. A method for determining whether an immune checkpoint-directed therapy is indicated for a patient suffering from a stage IV colorectal cancer with defective mismatch repair (dMMR), the method comprising obtaining an immune context score (ICS) according to the method according to claim 1 and determining that an immune checkpoint-directed therapy is indicated in case a high ICS is determined.

7. A method of treating a subject having a defective DNA mismatch repair (dMMR) stage IV colorectal cancer, the method comprising:

(i) labeling a first serial section of the human tissue sample collected from the stage IV colorectal tumor previously diagnosed as having deficient DNA mismatch repair with a human CD8 protein biomarker-specific reagent in combination with appropriate detection reagents;

(ii) annotating a tumor core (CT) region of interest (ROI) in a digital image of a second serial section of the human tissue sample, wherein the second serial section is stained with hematoxylin and eosin, and wherein the annotated ROI is automatically registered to a digital image of at least the first serial section of the human tissue sample;

(iii) detecting CD8+ cells in at least a portion of the ROI in the digital image of the at least the first serial section of the human tissue sample;

(iv) obtaining a CD8+ cell density within the ROI, wherein the CD8+ cell density is an area cell density obtained by dividing a quantity of the detected CD8+ cells in the ROI by the area of the ROI;

(v) applying a non-continuous scoring function to a feature vector comprising the obtained CD8+ cell density, wherein the non-continuous scoring function assigns the obtained CD8+ cell density to a pre-determined bin and calculates the ICS for the human tissue sample based on the assigned bin; and (vi) administering a treatment comprising a checkpoint inhibitor to the subject.

8. The method of claim 7, wherein said treatment further comprises reduced course of chemotherapy.

9. The method of claim 8, wherein said reduced course of chemotherapy is a reduction in the number of different chemotherapy agents used, of the dose of one or more chemotherapy agent(s), and/or of the duration of treatment with the one or more chemotherapy agent(s); and/or comprises selection of a chemotherapy agent that has a lower toxicity profile relative to other chemotherapy agents for the treatment of stage IV colorectal cancer.

10. The method of claim 7, wherein said checkpoint inhibitor is a checkpoint inhibitor targeting PD-1, PD-L1, CTLA-4, or indoleamine 2,3-dioxygenase (IDO), in an embodiment is a checkpoint inhibitor targeting PD-1 or PD-L1.

11. The method of claim 7, wherein said checkpoint inhibitor is pembrolizumab, nivolumab, cemiplimab, tislelizumab, spartalizumab, MEDI0680, JS001, IBI308, JNJ-63723283, atezolizumab, durvalumab, avelumab, ipilimumab, or NLG919.

12. The method of claim 1, further comprising normalizing the obtained CD8+ density by applying a normalization factor to the obtained CD8+ density; and wherein the feature vector comprises the normalized CD8+ cell density.

* * * * *

SEQUENCE LISTING

<160> NUMBER OF SEQ ID NOS: 14

<210> SEQ ID NO 1
<211> LENGTH: 182
<212> TYPE: PRT
<213> ORGANISM: Homo sapiens

<400> SEQUENCE: 1

Met Glu Gln Gly Lys Gly Leu Ala Val Leu Ile Leu Ala Ile Ile Leu
1 5 10 15

Leu Gln Gly Thr Leu Ala Gln Ser Ile Lys Gly Asn His Leu Val Lys
20 25 30

Val Tyr Asp Tyr Gln Glu Asp Gly Ser Val Leu Leu Thr Cys Asp Ala
35 40 45

Glu Ala Lys Asn Ile Thr Trp Phe Lys Asp Gly Lys Met Ile Gly Phe
50 55 60

Leu Thr Glu Asp Lys Lys Lys Trp Asn Leu Gly Ser Asn Ala Lys Asp
65 70 75 80

Pro Arg Gly Met Tyr Gln Cys Lys Gly Ser Gln Asn Lys Ser Lys Pro
85 90 95

Leu Gln Val Tyr Tyr Arg Met Cys Gln Asn Cys Ile Glu Leu Asn Ala
100 105 110

Ala Thr Ile Ser Gly Phe Leu Phe Ala Glu Ile Val Ser Ile Phe Val
115 120 125

Leu Ala Val Gly Val Tyr Phe Ile Ala Gly Gln Asp Gly Val Arg Gln
130 135 140

Ser Arg Ala Ser Asp Lys Gln Thr Leu Leu Pro Asn Asp Gln Leu Tyr
145 150 155 160

Gln Pro Leu Lys Asp Arg Glu Asp Asp Gln Tyr Ser His Leu Gln Gly
165 170 175

Asn Gln Leu Arg Arg Asn
180

<210> SEQ ID NO 2
<211> LENGTH: 171
<212> TYPE: PRT
<213> ORGANISM: Homo sapiens

<400> SEQUENCE: 2

Met Glu His Ser Thr Phe Leu Ser Gly Leu Val Leu Ala Thr Leu Leu
1 5 10 15

Ser Gln Val Ser Pro Phe Lys Ile Pro Ile Glu Glu Leu Glu Asp Arg
20 25 30

Val Phe Val Asn Cys Asn Thr Ser Ile Thr Trp Val Glu Gly Thr Val
35 40 45

Gly Thr Leu Leu Ser Asp Ile Thr Arg Leu Asp Leu Gly Lys Arg Ile
50 55 60

Leu Asp Pro Arg Gly Ile Tyr Arg Cys Asn Gly Thr Asp Ile Tyr Lys
65 70 75 80

Asp Lys Glu Ser Thr Val Gln Val His Tyr Arg Met Cys Gln Ser Cys
85 90 95

```
Val Glu Leu Asp Pro Ala Thr Val Ala Gly Ile Ile Val Thr Asp Val
            100                 105                 110

Ile Ala Thr Leu Leu Leu Ala Leu Gly Val Phe Cys Phe Ala Gly His
        115                 120                 125

Glu Thr Gly Arg Leu Ser Gly Ala Ala Asp Thr Gln Ala Leu Leu Arg
    130                 135                 140

Asn Asp Gln Val Tyr Gln Pro Leu Arg Asp Arg Asp Asp Ala Gln Tyr
145                 150                 155                 160

Ser His Leu Gly Gly Asn Trp Ala Arg Asn Lys
                165                 170


<210> SEQ ID NO 3
<211> LENGTH: 207
<212> TYPE: PRT
<213> ORGANISM: Homo sapiens

<400> SEQUENCE: 3

Met Gln Ser Gly Thr His Trp Arg Val Leu Gly Leu Cys Leu Leu Ser
1               5                   10                  15

Val Gly Val Trp Gly Gln Asp Gly Asn Glu Glu Met Gly Gly Ile Thr
            20                  25                  30

Gln Thr Pro Tyr Lys Val Ser Ile Ser Gly Thr Thr Val Ile Leu Thr
        35                  40                  45

Cys Pro Gln Tyr Pro Gly Ser Glu Ile Leu Trp Gln His Asn Asp Lys
    50                  55                  60

Asn Ile Gly Gly Asp Glu Asp Asp Lys Asn Ile Gly Ser Asp Glu Asp
65                  70                  75                  80

His Leu Ser Leu Lys Glu Phe Ser Glu Leu Glu Gln Ser Gly Tyr Tyr
                85                  90                  95

Val Cys Tyr Pro Arg Gly Ser Lys Pro Glu Asp Ala Asn Phe Tyr Leu
            100                 105                 110

Tyr Leu Arg Ala Arg Val Cys Glu Asn Cys Met Glu Met Asp Val Met
        115                 120                 125

Ser Val Ala Thr Ile Val Ile Val Asp Ile Cys Ile Thr Gly Gly Leu
    130                 135                 140

Leu Leu Leu Val Tyr Tyr Trp Ser Lys Asn Arg Lys Ala Lys Ala Lys
145                 150                 155                 160

Pro Val Thr Arg Gly Ala Gly Ala Gly Gly Arg Gln Arg Gly Gln Asn
                165                 170                 175

Lys Glu Arg Pro Pro Pro Val Pro Asn Pro Asp Tyr Glu Pro Ile Arg
            180                 185                 190

Lys Gly Gln Arg Asp Leu Tyr Ser Gly Leu Asn Gln Arg Arg Ile
        195                 200                 205


<210> SEQ ID NO 4
<211> LENGTH: 164
<212> TYPE: PRT
<213> ORGANISM: Homo sapiens

<400> SEQUENCE: 4

Met Lys Trp Lys Ala Leu Phe Thr Ala Ala Ile Leu Gln Ala Gln Leu
1               5                   10                  15

Pro Ile Thr Glu Ala Gln Ser Phe Gly Leu Leu Asp Pro Lys Leu Cys
            20                  25                  30

Tyr Leu Leu Asp Gly Ile Leu Phe Ile Tyr Gly Val Ile Leu Thr Ala
        35                  40                  45
```

```
Leu Phe Leu Arg Val Lys Phe Ser Arg Ser Ala Asp Ala Pro Ala Tyr
    50                  55                  60

Gln Gln Gly Gln Asn Gln Leu Tyr Asn Glu Leu Asn Leu Gly Arg Arg
65                  70                  75                  80

Glu Glu Tyr Asp Val Leu Asp Lys Arg Arg Gly Arg Asp Pro Glu Met
                85                  90                  95

Gly Gly Lys Pro Gln Arg Arg Lys Asn Pro Gln Glu Gly Leu Tyr Asn
            100                 105                 110

Glu Leu Gln Lys Asp Lys Met Ala Glu Ala Tyr Ser Glu Ile Gly Met
        115                 120                 125

Lys Gly Glu Arg Arg Arg Gly Lys Gly His Asp Gly Leu Tyr Gln Gly
    130                 135                 140

Leu Ser Thr Ala Thr Lys Asp Thr Tyr Asp Ala Leu His Met Gln Ala
145                 150                 155                 160

Leu Pro Pro Arg


<210> SEQ ID NO 5
<211> LENGTH: 235
<212> TYPE: PRT
<213> ORGANISM: Homo sapiens

<400> SEQUENCE: 5

Met Ala Leu Pro Val Thr Ala Leu Leu Leu Pro Leu Ala Leu Leu Leu
1               5                   10                  15

His Ala Ala Arg Pro Ser Gln Phe Arg Val Ser Pro Leu Asp Arg Thr
            20                  25                  30

Trp Asn Leu Gly Glu Thr Val Glu Leu Lys Cys Gln Val Leu Leu Ser
        35                  40                  45

Asn Pro Thr Ser Gly Cys Ser Trp Leu Phe Gln Pro Arg Gly Ala Ala
    50                  55                  60

Ala Ser Pro Thr Phe Leu Leu Tyr Leu Ser Gln Asn Lys Pro Lys Ala
65                  70                  75                  80

Ala Glu Gly Leu Asp Thr Gln Arg Phe Ser Gly Lys Arg Leu Gly Asp
                85                  90                  95

Thr Phe Val Leu Thr Leu Ser Asp Phe Arg Arg Glu Asn Glu Gly Tyr
            100                 105                 110

Tyr Phe Cys Ser Ala Leu Ser Asn Ser Ile Met Tyr Phe Ser His Phe
        115                 120                 125

Val Pro Val Phe Leu Pro Ala Lys Pro Thr Thr Thr Pro Ala Pro Arg
    130                 135                 140

Pro Pro Thr Pro Ala Pro Thr Ile Ala Ser Gln Pro Leu Ser Leu Arg
145                 150                 155                 160

Pro Glu Ala Cys Arg Pro Ala Ala Gly Gly Ala Val His Thr Arg Gly
                165                 170                 175

Leu Asp Phe Ala Cys Asp Ile Tyr Ile Trp Ala Pro Leu Ala Gly Thr
            180                 185                 190

Cys Gly Val Leu Leu Leu Ser Leu Val Ile Thr Leu Tyr Cys Asn His
        195                 200                 205

Arg Asn Arg Arg Arg Val Cys Lys Cys Pro Arg Pro Val Val Lys Ser
    210                 215                 220

Gly Asp Lys Pro Ser Leu Ser Ala Arg Tyr Val
225                 230                 235


<210> SEQ ID NO 6
<211> LENGTH: 210
```

<212> TYPE: PRT
<213> ORGANISM: Homo sapiens

<400> SEQUENCE: 6

Met Arg Pro Arg Leu Trp Leu Leu Leu Ala Ala Gln Leu Thr Val Leu
1 5 10 15

His Gly Asn Ser Val Leu Gln Gln Thr Pro Ala Tyr Ile Lys Val Gln
20 25 30

Thr Asn Lys Met Val Met Leu Ser Cys Glu Ala Lys Ile Ser Leu Ser
35 40 45

Asn Met Arg Ile Tyr Trp Leu Arg Gln Arg Gln Ala Pro Ser Ser Asp
50 55 60

Ser His His Glu Phe Leu Ala Leu Trp Asp Ser Ala Lys Gly Thr Ile
65 70 75 80

His Gly Glu Glu Val Glu Gln Glu Lys Ile Ala Val Phe Arg Asp Ala
85 90 95

Ser Arg Phe Ile Leu Asn Leu Thr Ser Val Lys Pro Glu Asp Ser Gly
100 105 110

Ile Tyr Phe Cys Met Ile Val Gly Ser Pro Glu Leu Thr Phe Gly Lys
115 120 125

Gly Thr Gln Leu Ser Val Val Asp Phe Leu Pro Thr Thr Ala Gln Pro
130 135 140

Thr Lys Lys Ser Thr Leu Lys Lys Arg Val Cys Arg Leu Pro Arg Pro
145 150 155 160

Glu Thr Gln Lys Gly Pro Leu Cys Ser Pro Ile Thr Leu Gly Leu Leu
165 170 175

Val Ala Gly Val Leu Val Leu Leu Val Ser Leu Gly Val Ala Ile His
180 185 190

Leu Cys Cys Arg Arg Arg Arg Ala Arg Leu Arg Phe Met Lys Gln Phe
195 200 205

Tyr Lys
210

<210> SEQ ID NO 7
<211> LENGTH: 431
<212> TYPE: PRT
<213> ORGANISM: Homo sapiens

<400> SEQUENCE: 7

Met Pro Asn Pro Arg Pro Gly Lys Pro Ser Ala Pro Ser Leu Ala Leu
1 5 10 15

Gly Pro Ser Pro Gly Ala Ser Pro Ser Trp Arg Ala Ala Pro Lys Ala
20 25 30

Ser Asp Leu Leu Gly Ala Arg Gly Pro Gly Gly Thr Phe Gln Gly Arg
35 40 45

Asp Leu Arg Gly Gly Ala His Ala Ser Ser Ser Ser Leu Asn Pro Met
50 55 60

Pro Pro Ser Gln Leu Gln Leu Pro Thr Leu Pro Leu Val Met Val Ala
65 70 75 80

Pro Ser Gly Ala Arg Leu Gly Pro Leu Pro His Leu Gln Ala Leu Leu
85 90 95

Gln Asp Arg Pro His Phe Met His Gln Leu Ser Thr Val Asp Ala His
100 105 110

Ala Arg Thr Pro Val Leu Gln Val His Pro Leu Glu Ser Pro Ala Met
115 120 125

```
Ile Ser Leu Thr Pro Pro Thr Thr Ala Thr Gly Val Phe Ser Leu Lys
    130                 135                 140

Ala Arg Pro Gly Leu Pro Pro Gly Ile Asn Val Ala Ser Leu Glu Trp
145                 150                 155                 160

Val Ser Arg Glu Pro Ala Leu Leu Cys Thr Phe Pro Asn Pro Ser Ala
                165                 170                 175

Pro Arg Lys Asp Ser Thr Leu Ser Ala Val Pro Gln Ser Ser Tyr Pro
            180                 185                 190

Leu Leu Ala Asn Gly Val Cys Lys Trp Pro Gly Cys Glu Lys Val Phe
        195                 200                 205

Glu Glu Pro Glu Asp Phe Leu Lys His Cys Gln Ala Asp His Leu Leu
    210                 215                 220

Asp Glu Lys Gly Arg Ala Gln Cys Leu Leu Gln Arg Glu Met Val Gln
225                 230                 235                 240

Ser Leu Glu Gln Gln Leu Val Leu Glu Lys Glu Lys Leu Ser Ala Met
                245                 250                 255

Gln Ala His Leu Ala Gly Lys Met Ala Leu Thr Lys Ala Ser Ser Val
            260                 265                 270

Ala Ser Ser Asp Lys Gly Ser Cys Cys Ile Val Ala Ala Gly Ser Gln
        275                 280                 285

Gly Pro Val Val Pro Ala Trp Ser Gly Pro Arg Glu Ala Pro Asp Ser
    290                 295                 300

Leu Phe Ala Val Arg Arg His Leu Trp Gly Ser His Gly Asn Ser Thr
305                 310                 315                 320

Phe Pro Glu Phe Leu His Asn Met Asp Tyr Phe Lys Phe His Asn Met
                325                 330                 335

Arg Pro Pro Phe Thr Tyr Ala Thr Leu Ile Arg Trp Ala Ile Leu Glu
            340                 345                 350

Ala Pro Glu Lys Gln Arg Thr Leu Asn Glu Ile Tyr His Trp Phe Thr
        355                 360                 365

Arg Met Phe Ala Phe Phe Arg Asn His Pro Ala Thr Trp Lys Asn Ala
    370                 375                 380

Ile Arg His Asn Leu Ser Leu His Lys Cys Phe Val Arg Val Glu Ser
385                 390                 395                 400

Glu Lys Gly Ala Val Trp Thr Val Asp Glu Leu Glu Phe Arg Lys Lys
                405                 410                 415

Arg Ser Gln Arg Pro Ser Arg Cys Ser Asn Pro Thr Pro Gly Pro
            420                 425                 430


<210> SEQ ID NO 8
<211> LENGTH: 288
<212> TYPE: PRT
<213> ORGANISM: Homo sapiens

<400> SEQUENCE: 8

Met Gln Ile Pro Gln Ala Pro Trp Pro Val Val Trp Ala Val Leu Gln
1               5                   10                  15

Leu Gly Trp Arg Pro Gly Trp Phe Leu Asp Ser Pro Asp Arg Pro Trp
            20                  25                  30

Asn Pro Pro Thr Phe Ser Pro Ala Leu Leu Val Val Thr Glu Gly Asp
        35                  40                  45

Asn Ala Thr Phe Thr Cys Ser Phe Ser Asn Thr Ser Glu Ser Phe Val
    50                  55                  60

Leu Asn Trp Tyr Arg Met Ser Pro Ser Asn Gln Thr Asp Lys Leu Ala
65                  70                  75                  80
```

```
Ala Phe Pro Glu Asp Arg Ser Gln Pro Gly Gln Asp Cys Arg Phe Arg
                85                  90                  95

Val Thr Gln Leu Pro Asn Gly Arg Asp Phe His Met Ser Val Val Arg
            100                 105                 110

Ala Arg Arg Asn Asp Ser Gly Thr Tyr Leu Cys Gly Ala Ile Ser Leu
        115                 120                 125

Ala Pro Lys Ala Gln Ile Lys Glu Ser Leu Arg Ala Glu Leu Arg Val
    130                 135                 140

Thr Glu Arg Arg Ala Glu Val Pro Thr Ala His Pro Ser Pro Ser Pro
145                 150                 155                 160

Arg Pro Ala Gly Gln Phe Gln Thr Leu Val Val Gly Val Val Gly Gly
                165                 170                 175

Leu Leu Gly Ser Leu Val Leu Leu Val Trp Val Leu Ala Val Ile Cys
            180                 185                 190

Ser Arg Ala Ala Arg Gly Thr Ile Gly Ala Arg Arg Thr Gly Gln Pro
        195                 200                 205

Leu Lys Glu Asp Pro Ser Ala Val Pro Val Phe Ser Val Asp Tyr Gly
    210                 215                 220

Glu Leu Asp Phe Gln Trp Arg Glu Lys Thr Pro Glu Pro Pro Val Pro
225                 230                 235                 240

Cys Val Pro Glu Gln Thr Glu Tyr Ala Thr Ile Val Phe Pro Ser Gly
                245                 250                 255

Met Gly Thr Ser Ser Pro Ala Arg Arg Gly Ser Ala Asp Gly Pro Arg
            260                 265                 270

Ser Ala Gln Pro Leu Arg Pro Glu Asp Gly His Cys Ser Trp Pro Leu
        275                 280                 285


<210> SEQ ID NO 9
<211> LENGTH: 290
<212> TYPE: PRT
<213> ORGANISM: Homo sapiens

<400> SEQUENCE: 9

Met Arg Ile Phe Ala Val Phe Ile Phe Met Thr Tyr Trp His Leu Leu
1               5                   10                  15

Asn Ala Phe Thr Val Thr Val Pro Lys Asp Leu Tyr Val Val Glu Tyr
            20                  25                  30

Gly Ser Asn Met Thr Ile Glu Cys Lys Phe Pro Val Glu Lys Gln Leu
        35                  40                  45

Asp Leu Ala Ala Leu Ile Val Tyr Trp Glu Met Glu Asp Lys Asn Ile
    50                  55                  60

Ile Gln Phe Val His Gly Glu Glu Asp Leu Lys Val Gln His Ser Ser
65                  70                  75                  80

Tyr Arg Gln Arg Ala Arg Leu Leu Lys Asp Gln Leu Ser Leu Gly Asn
                85                  90                  95

Ala Ala Leu Gln Ile Thr Asp Val Lys Leu Gln Asp Ala Gly Val Tyr
            100                 105                 110

Arg Cys Met Ile Ser Tyr Gly Gly Ala Asp Tyr Lys Arg Ile Thr Val
        115                 120                 125

Lys Val Asn Ala Pro Tyr Asn Lys Ile Asn Gln Arg Ile Leu Val Val
    130                 135                 140

Asp Pro Val Thr Ser Glu His Glu Leu Thr Cys Gln Ala Glu Gly Tyr
145                 150                 155                 160

Pro Lys Ala Glu Val Ile Trp Thr Ser Ser Asp His Gln Val Leu Ser
```

```
                165                 170                 175

Gly Lys Thr Thr Thr Thr Asn Ser Lys Arg Glu Glu Lys Leu Phe Asn
            180                 185                 190

Val Thr Ser Thr Leu Arg Ile Asn Thr Thr Thr Asn Glu Ile Phe Tyr
        195                 200                 205

Cys Thr Phe Arg Arg Leu Asp Pro Glu Glu Asn His Thr Ala Glu Leu
    210                 215                 220

Val Ile Pro Glu Leu Pro Leu Ala His Pro Pro Asn Glu Arg Thr His
225                 230                 235                 240

Leu Val Ile Leu Gly Ala Ile Leu Leu Cys Leu Gly Val Ala Leu Thr
                245                 250                 255

Phe Ile Phe Arg Leu Arg Lys Gly Arg Met Met Asp Val Lys Lys Cys
            260                 265                 270

Gly Ile Gln Asp Thr Asn Ser Lys Lys Gln Ser Asp Thr His Leu Glu
        275                 280                 285

Glu Thr
    290


<210> SEQ ID NO 10
<211> LENGTH: 403
<212> TYPE: PRT
<213> ORGANISM: Homo sapiens

<400> SEQUENCE: 10

Met Ala His Ala Met Glu Asn Ser Trp Thr Ile Ser Lys Glu Tyr His
1               5                   10                  15

Ile Asp Glu Glu Val Gly Phe Ala Leu Pro Asn Pro Gln Glu Asn Leu
            20                  25                  30

Pro Asp Phe Tyr Asn Asp Trp Met Phe Ile Ala Lys His Leu Pro Asp
        35                  40                  45

Leu Ile Glu Ser Gly Gln Leu Arg Glu Arg Val Glu Lys Leu Asn Met
    50                  55                  60

Leu Ser Ile Asp His Leu Thr Asp His Lys Ser Gln Arg Leu Ala Arg
65                  70                  75                  80

Leu Val Leu Gly Cys Ile Thr Met Ala Tyr Val Trp Gly Lys Gly His
                85                  90                  95

Gly Asp Val Arg Lys Val Leu Pro Arg Asn Ile Ala Val Pro Tyr Cys
            100                 105                 110

Gln Leu Ser Lys Lys Leu Glu Leu Pro Pro Ile Leu Val Tyr Ala Asp
        115                 120                 125

Cys Val Leu Ala Asn Trp Lys Lys Lys Asp Pro Asn Lys Pro Leu Thr
    130                 135                 140

Tyr Glu Asn Met Asp Val Leu Phe Ser Phe Arg Asp Gly Asp Cys Ser
145                 150                 155                 160

Lys Gly Phe Phe Leu Val Ser Leu Leu Val Glu Ile Ala Ala Ala Ser
                165                 170                 175

Ala Ile Lys Val Ile Pro Thr Val Phe Lys Ala Met Gln Met Gln Glu
            180                 185                 190

Arg Asp Thr Leu Leu Lys Ala Leu Leu Glu Ile Ala Ser Cys Leu Glu
        195                 200                 205

Lys Ala Leu Gln Val Phe His Gln Ile His Asp His Val Asn Pro Lys
    210                 215                 220

Ala Phe Phe Ser Val Leu Arg Ile Tyr Leu Ser Gly Trp Lys Gly Asn
225                 230                 235                 240
```

-continued

```
Pro Gln Leu Ser Asp Gly Leu Val Tyr Glu Gly Phe Trp Glu Asp Pro
                245                 250                 255

Lys Glu Phe Ala Gly Gly Ser Ala Gly Gln Ser Ser Val Phe Gln Cys
            260                 265                 270

Phe Asp Val Leu Leu Gly Ile Gln Gln Thr Ala Gly Gly Gly His Ala
        275                 280                 285

Ala Gln Phe Leu Gln Asp Met Arg Arg Tyr Met Pro Pro Ala His Arg
    290                 295                 300

Asn Phe Leu Cys Ser Leu Glu Ser Asn Pro Ser Val Arg Glu Phe Val
305                 310                 315                 320

Leu Ser Lys Gly Asp Ala Gly Leu Arg Glu Ala Tyr Asp Ala Cys Val
                325                 330                 335

Lys Ala Leu Val Ser Leu Arg Ser Tyr His Leu Gln Ile Val Thr Lys
            340                 345                 350

Tyr Ile Leu Ile Pro Ala Ser Gln Gln Pro Lys Glu Asn Lys Thr Ser
        355                 360                 365

Glu Asp Pro Ser Lys Leu Glu Ala Lys Gly Thr Gly Gly Thr Asp Leu
    370                 375                 380

Met Asn Phe Leu Lys Thr Val Arg Ser Thr Thr Glu Lys Ser Leu Leu
385                 390                 395                 400

Lys Glu Gly


<210> SEQ ID NO 11
<211> LENGTH: 862
<212> TYPE: PRT
<213> ORGANISM: Homo sapiens

<400> SEQUENCE: 11

Met Glu Arg Ala Glu Ser Ser Ser Thr Glu Pro Ala Lys Ala Ile Lys
1               5                   10                  15

Pro Ile Asp Arg Lys Ser Val His Gln Ile Cys Ser Gly Gln Val Val
            20                  25                  30

Leu Ser Leu Ser Thr Ala Val Lys Glu Leu Val Glu Asn Ser Leu Asp
        35                  40                  45

Ala Gly Ala Thr Asn Ile Asp Leu Lys Leu Lys Asp Tyr Gly Val Asp
    50                  55                  60

Leu Ile Glu Val Ser Asp Asn Gly Cys Gly Val Glu Glu Glu Asn Phe
65                  70                  75                  80

Glu Gly Leu Thr Leu Lys His His Thr Ser Lys Ile Gln Glu Phe Ala
                85                  90                  95

Asp Leu Thr Gln Val Glu Thr Phe Gly Phe Arg Gly Glu Ala Leu Ser
            100                 105                 110

Ser Leu Cys Ala Leu Ser Asp Val Thr Ile Ser Thr Cys His Ala Ser
        115                 120                 125

Ala Lys Val Gly Thr Arg Leu Met Phe Asp His Asn Gly Lys Ile Ile
    130                 135                 140

Gln Lys Thr Pro Tyr Pro Arg Pro Arg Gly Thr Thr Val Ser Val Gln
145                 150                 155                 160

Gln Leu Phe Ser Thr Leu Pro Val Arg His Lys Glu Phe Gln Arg Asn
                165                 170                 175

Ile Lys Lys Glu Tyr Ala Lys Met Val Gln Val Leu His Ala Tyr Cys
            180                 185                 190

Ile Ile Ser Ala Gly Ile Arg Val Ser Cys Thr Asn Gln Leu Gly Gln
        195                 200                 205
```

```
Gly Lys Arg Gln Pro Val Val Cys Thr Gly Gly Ser Pro Ser Ile Lys
    210                 215                 220

Glu Asn Ile Gly Ser Val Phe Gly Gln Lys Gln Leu Gln Ser Leu Ile
225                 230                 235                 240

Pro Phe Val Gln Leu Pro Pro Ser Asp Ser Val Cys Glu Glu Tyr Gly
                245                 250                 255

Leu Ser Cys Ser Asp Ala Leu His Asn Leu Phe Tyr Ile Ser Gly Phe
            260                 265                 270

Ile Ser Gln Cys Thr His Gly Val Gly Arg Ser Ser Thr Asp Arg Gln
        275                 280                 285

Phe Phe Phe Ile Asn Arg Arg Pro Cys Asp Pro Ala Lys Val Cys Arg
    290                 295                 300

Leu Val Asn Glu Val Tyr His Met Tyr Asn Arg His Gln Tyr Pro Phe
305                 310                 315                 320

Val Val Leu Asn Ile Ser Val Asp Ser Glu Cys Val Asp Ile Asn Val
                325                 330                 335

Thr Pro Asp Lys Arg Gln Ile Leu Leu Gln Glu Glu Lys Leu Leu Leu
            340                 345                 350

Ala Val Leu Lys Thr Ser Leu Ile Gly Met Phe Asp Ser Asp Val Asn
        355                 360                 365

Lys Leu Asn Val Ser Gln Gln Pro Leu Leu Asp Val Glu Gly Asn Leu
    370                 375                 380

Ile Lys Met His Ala Ala Asp Leu Glu Lys Pro Met Val Glu Lys Gln
385                 390                 395                 400

Asp Gln Ser Pro Ser Leu Arg Thr Gly Glu Glu Lys Lys Asp Val Ser
                405                 410                 415

Ile Ser Arg Leu Arg Glu Ala Phe Ser Leu Arg His Thr Thr Glu Asn
            420                 425                 430

Lys Pro His Ser Pro Lys Thr Pro Glu Pro Arg Arg Ser Pro Leu Gly
        435                 440                 445

Gln Lys Arg Gly Met Leu Ser Ser Ser Thr Ser Gly Ala Ile Ser Asp
    450                 455                 460

Lys Gly Val Leu Arg Pro Gln Lys Glu Ala Val Ser Ser Ser His Gly
465                 470                 475                 480

Pro Ser Asp Pro Thr Asp Arg Ala Glu Val Glu Lys Asp Ser Gly His
                485                 490                 495

Gly Ser Thr Ser Val Asp Ser Glu Gly Phe Ser Ile Pro Asp Thr Gly
            500                 505                 510

Ser His Cys Ser Ser Glu Tyr Ala Ala Ser Ser Pro Gly Asp Arg Gly
        515                 520                 525

Ser Gln Glu His Val Asp Ser Gln Glu Lys Ala Pro Lys Thr Asp Asp
    530                 535                 540

Ser Phe Ser Asp Val Asp Cys His Ser Asn Gln Glu Asp Thr Gly Cys
545                 550                 555                 560

Lys Phe Arg Val Leu Pro Gln Pro Thr Asn Leu Ala Thr Pro Asn Thr
                565                 570                 575

Lys Arg Phe Lys Lys Glu Glu Ile Leu Ser Ser Ser Asp Ile Cys Gln
            580                 585                 590

Lys Leu Val Asn Thr Gln Asp Met Ser Ala Ser Gln Val Asp Val Ala
        595                 600                 605

Val Lys Ile Asn Lys Lys Val Val Pro Leu Asp Phe Ser Met Ser Ser
    610                 615                 620

Leu Ala Lys Arg Ile Lys Gln Leu His His Glu Ala Gln Gln Ser Glu
```

```
625                 630                 635                 640

Gly Glu Gln Asn Tyr Arg Lys Phe Arg Ala Lys Ile Cys Pro Gly Glu
                645                 650                 655

Asn Gln Ala Ala Glu Asp Glu Leu Arg Lys Glu Ile Ser Lys Thr Met
            660                 665                 670

Phe Ala Glu Met Glu Ile Ile Gly Gln Phe Asn Leu Gly Phe Ile Ile
        675                 680                 685

Thr Lys Leu Asn Glu Asp Ile Phe Ile Val Asp Gln His Ala Thr Asp
    690                 695                 700

Glu Lys Tyr Asn Phe Glu Met Leu Gln Gln His Thr Val Leu Gln Gly
705                 710                 715                 720

Gln Arg Leu Ile Ala Pro Gln Thr Leu Asn Leu Thr Ala Val Asn Glu
                725                 730                 735

Ala Val Leu Ile Glu Asn Leu Glu Ile Phe Arg Lys Asn Gly Phe Asp
            740                 745                 750

Phe Val Ile Asp Glu Asn Ala Pro Val Thr Glu Arg Ala Lys Leu Ile
        755                 760                 765

Ser Leu Pro Thr Ser Lys Asn Trp Thr Phe Gly Pro Gln Asp Val Asp
    770                 775                 780

Glu Leu Ile Phe Met Leu Ser Asp Ser Pro Gly Val Met Cys Arg Pro
785                 790                 795                 800

Ser Arg Val Lys Gln Met Phe Ala Ser Arg Ala Cys Arg Lys Ser Val
                805                 810                 815

Met Ile Gly Thr Ala Leu Asn Thr Ser Glu Met Lys Lys Leu Ile Thr
            820                 825                 830

His Met Gly Glu Met Asp His Pro Trp Asn Cys Pro His Gly Arg Pro
        835                 840                 845

Thr Met Arg His Ile Ala Asn Leu Gly Val Ile Ser Gln Asn
    850                 855                 860


<210> SEQ ID NO 12
<211> LENGTH: 756
<212> TYPE: PRT
<213> ORGANISM: Homo sapiens

<400> SEQUENCE: 12

Met Ser Phe Val Ala Gly Val Ile Arg Arg Leu Asp Glu Thr Val Val
1               5                   10                  15

Asn Arg Ile Ala Ala Gly Glu Val Ile Gln Arg Pro Ala Asn Ala Ile
            20                  25                  30

Lys Glu Met Ile Glu Asn Cys Leu Asp Ala Lys Ser Thr Ser Ile Gln
        35                  40                  45

Val Ile Val Lys Glu Gly Gly Leu Lys Leu Ile Gln Ile Gln Asp Asn
    50                  55                  60

Gly Thr Gly Ile Arg Lys Glu Asp Leu Asp Ile Val Cys Glu Arg Phe
65                  70                  75                  80

Thr Thr Ser Lys Leu Gln Ser Phe Glu Asp Leu Ala Ser Ile Ser Thr
                85                  90                  95

Tyr Gly Phe Arg Gly Glu Ala Leu Ala Ser Ile Ser His Val Ala His
            100                 105                 110

Val Thr Ile Thr Thr Lys Thr Ala Asp Gly Lys Cys Ala Tyr Arg Ala
        115                 120                 125

Ser Tyr Ser Asp Gly Lys Leu Lys Ala Pro Pro Lys Pro Cys Ala Gly
    130                 135                 140
```

Asn Gln Gly Thr Gln Ile Thr Val Glu Asp Leu Phe Tyr Asn Ile Ala
145 150 155 160

Thr Arg Arg Lys Ala Leu Lys Asn Pro Ser Glu Glu Tyr Gly Lys Ile
165 170 175

Leu Glu Val Val Gly Arg Tyr Ser Val His Asn Ala Gly Ile Ser Phe
180 185 190

Ser Val Lys Lys Gln Gly Glu Thr Val Ala Asp Val Arg Thr Leu Pro
195 200 205

Asn Ala Ser Thr Val Asp Asn Ile Arg Ser Ile Phe Gly Asn Ala Val
210 215 220

Ser Arg Glu Leu Ile Glu Ile Gly Cys Glu Asp Lys Thr Leu Ala Phe
225 230 235 240

Lys Met Asn Gly Tyr Ile Ser Asn Ala Asn Tyr Ser Val Lys Lys Cys
245 250 255

Ile Phe Leu Leu Phe Ile Asn His Arg Leu Val Glu Ser Thr Ser Leu
260 265 270

Arg Lys Ala Ile Glu Thr Val Tyr Ala Ala Tyr Leu Pro Lys Asn Thr
275 280 285

His Pro Phe Leu Tyr Leu Ser Leu Glu Ile Ser Pro Gln Asn Val Asp
290 295 300

Val Asn Val His Pro Thr Lys His Glu Val His Phe Leu His Glu Glu
305 310 315 320

Ser Ile Leu Glu Arg Val Gln Gln His Ile Glu Ser Lys Leu Leu Gly
325 330 335

Ser Asn Ser Ser Arg Met Tyr Phe Thr Gln Thr Leu Leu Pro Gly Leu
340 345 350

Ala Gly Pro Ser Gly Glu Met Val Lys Ser Thr Thr Ser Leu Thr Ser
355 360 365

Ser Ser Thr Ser Gly Ser Ser Asp Lys Val Tyr Ala His Gln Met Val
370 375 380

Arg Thr Asp Ser Arg Glu Gln Lys Leu Asp Ala Phe Leu Gln Pro Leu
385 390 395 400

Ser Lys Pro Leu Ser Ser Gln Pro Gln Ala Ile Val Thr Glu Asp Lys
405 410 415

Thr Asp Ile Ser Ser Gly Arg Ala Arg Gln Gln Asp Glu Glu Met Leu
420 425 430

Glu Leu Pro Ala Pro Ala Glu Val Ala Ala Lys Asn Gln Ser Leu Glu
435 440 445

Gly Asp Thr Thr Lys Gly Thr Ser Glu Met Ser Glu Lys Arg Gly Pro
450 455 460

Thr Ser Ser Asn Pro Arg Lys Arg His Arg Glu Asp Ser Asp Val Glu
465 470 475 480

Met Val Glu Asp Asp Ser Arg Lys Glu Met Thr Ala Ala Cys Thr Pro
485 490 495

Arg Arg Arg Ile Ile Asn Leu Thr Ser Val Leu Ser Leu Gln Glu Glu
500 505 510

Ile Asn Glu Gln Gly His Glu Val Leu Arg Glu Met Leu His Asn His
515 520 525

Ser Phe Val Gly Cys Val Asn Pro Gln Trp Ala Leu Ala Gln His Gln
530 535 540

Thr Lys Leu Tyr Leu Leu Asn Thr Thr Lys Leu Ser Glu Glu Leu Phe
545 550 555 560

Tyr Gln Ile Leu Ile Tyr Asp Phe Ala Asn Phe Gly Val Leu Arg Leu

```
                565                 570                 575

Ser Glu Pro Ala Pro Leu Phe Asp Leu Ala Met Leu Ala Leu Asp Ser
            580                 585                 590

Pro Glu Ser Gly Trp Thr Glu Glu Asp Gly Pro Lys Glu Gly Leu Ala
        595                 600                 605

Glu Tyr Ile Val Glu Phe Leu Lys Lys Lys Ala Glu Met Leu Ala Asp
    610                 615                 620

Tyr Phe Ser Leu Glu Ile Asp Glu Glu Gly Asn Leu Ile Gly Leu Pro
625                 630                 635                 640

Leu Leu Ile Asp Asn Tyr Val Pro Pro Leu Glu Gly Leu Pro Ile Phe
                645                 650                 655

Ile Leu Arg Leu Ala Thr Glu Val Asn Trp Asp Glu Glu Lys Glu Cys
            660                 665                 670

Phe Glu Ser Leu Ser Lys Glu Cys Ala Met Phe Tyr Ser Ile Arg Lys
        675                 680                 685

Gln Tyr Ile Ser Glu Glu Ser Thr Leu Ser Gly Gln Gln Ser Glu Val
    690                 695                 700

Pro Gly Ser Ile Pro Asn Ser Trp Lys Trp Thr Val Glu His Ile Val
705                 710                 715                 720

Tyr Lys Ala Leu Arg Ser His Ile Leu Pro Pro Lys His Phe Thr Glu
                725                 730                 735

Asp Gly Asn Ile Leu Gln Leu Ala Asn Leu Pro Asp Leu Tyr Lys Val
            740                 745                 750

Phe Glu Arg Cys
        755


<210> SEQ ID NO 13
<211> LENGTH: 934
<212> TYPE: PRT
<213> ORGANISM: Homo sapiens

<400> SEQUENCE: 13

Met Ala Val Gln Pro Lys Glu Thr Leu Gln Leu Glu Ser Ala Ala Glu
1               5                   10                  15

Val Gly Phe Val Arg Phe Phe Gln Gly Met Pro Glu Lys Pro Thr Thr
            20                  25                  30

Thr Val Arg Leu Phe Asp Arg Gly Asp Phe Tyr Thr Ala His Gly Glu
        35                  40                  45

Asp Ala Leu Leu Ala Ala Arg Glu Val Phe Lys Thr Gln Gly Val Ile
    50                  55                  60

Lys Tyr Met Gly Pro Ala Gly Ala Lys Asn Leu Gln Ser Val Val Leu
65                  70                  75                  80

Ser Lys Met Asn Phe Glu Ser Phe Val Lys Asp Leu Leu Leu Val Arg
                85                  90                  95

Gln Tyr Arg Val Glu Val Tyr Lys Asn Arg Ala Gly Asn Lys Ala Ser
            100                 105                 110

Lys Glu Asn Asp Trp Tyr Leu Ala Tyr Lys Ala Ser Pro Gly Asn Leu
        115                 120                 125

Ser Gln Phe Glu Asp Ile Leu Phe Gly Asn Asn Asp Met Ser Ala Ser
    130                 135                 140

Ile Gly Val Val Gly Val Lys Met Ser Ala Val Asp Gly Gln Arg Gln
145                 150                 155                 160

Val Gly Val Gly Tyr Val Asp Ser Ile Gln Arg Lys Leu Gly Leu Cys
                165                 170                 175
```

```
Glu Phe Pro Asp Asn Asp Gln Phe Ser Asn Leu Glu Ala Leu Leu Ile
            180                 185                 190

Gln Ile Gly Pro Lys Glu Cys Val Leu Pro Gly Gly Glu Thr Ala Gly
        195                 200                 205

Asp Met Gly Lys Leu Arg Gln Ile Ile Gln Arg Gly Gly Ile Leu Ile
    210                 215                 220

Thr Glu Arg Lys Lys Ala Asp Phe Ser Thr Lys Asp Ile Tyr Gln Asp
225                 230                 235                 240

Leu Asn Arg Leu Leu Lys Gly Lys Lys Gly Glu Gln Met Asn Ser Ala
                245                 250                 255

Val Leu Pro Glu Met Glu Asn Gln Val Ala Val Ser Ser Leu Ser Ala
            260                 265                 270

Val Ile Lys Phe Leu Glu Leu Leu Ser Asp Asp Ser Asn Phe Gly Gln
        275                 280                 285

Phe Glu Leu Thr Thr Phe Asp Phe Ser Gln Tyr Met Lys Leu Asp Ile
    290                 295                 300

Ala Ala Val Arg Ala Leu Asn Leu Phe Gln Gly Ser Val Glu Asp Thr
305                 310                 315                 320

Thr Gly Ser Gln Ser Leu Ala Ala Leu Leu Asn Lys Cys Lys Thr Pro
                325                 330                 335

Gln Gly Gln Arg Leu Val Asn Gln Trp Ile Lys Gln Pro Leu Met Asp
            340                 345                 350

Lys Asn Arg Ile Glu Glu Arg Leu Asn Leu Val Glu Ala Phe Val Glu
        355                 360                 365

Asp Ala Glu Leu Arg Gln Thr Leu Gln Glu Asp Leu Leu Arg Arg Phe
    370                 375                 380

Pro Asp Leu Asn Arg Leu Ala Lys Lys Phe Gln Arg Gln Ala Ala Asn
385                 390                 395                 400

Leu Gln Asp Cys Tyr Arg Leu Tyr Gln Gly Ile Asn Gln Leu Pro Asn
                405                 410                 415

Val Ile Gln Ala Leu Glu Lys His Glu Gly Lys His Gln Lys Leu Leu
            420                 425                 430

Leu Ala Val Phe Val Thr Pro Leu Thr Asp Leu Arg Ser Asp Phe Ser
        435                 440                 445

Lys Phe Gln Glu Met Ile Glu Thr Thr Leu Asp Met Asp Gln Val Glu
    450                 455                 460

Asn His Glu Phe Leu Val Lys Pro Ser Phe Asp Pro Asn Leu Ser Glu
465                 470                 475                 480

Leu Arg Glu Ile Met Asn Asp Leu Glu Lys Lys Met Gln Ser Thr Leu
                485                 490                 495

Ile Ser Ala Ala Arg Asp Leu Gly Leu Asp Pro Gly Lys Gln Ile Lys
            500                 505                 510

Leu Asp Ser Ser Ala Gln Phe Gly Tyr Tyr Phe Arg Val Thr Cys Lys
        515                 520                 525

Glu Glu Lys Val Leu Arg Asn Asn Lys Asn Phe Ser Thr Val Asp Ile
    530                 535                 540

Gln Lys Asn Gly Val Lys Phe Thr Asn Ser Lys Leu Thr Ser Leu Asn
545                 550                 555                 560

Glu Glu Tyr Thr Lys Asn Lys Thr Glu Tyr Glu Glu Ala Gln Asp Ala
                565                 570                 575

Ile Val Lys Glu Ile Val Asn Ile Ser Ser Gly Tyr Val Glu Pro Met
            580                 585                 590

Gln Thr Leu Asn Asp Val Leu Ala Gln Leu Asp Ala Val Val Ser Phe
```

```
        595                 600                 605

Ala His Val Ser Asn Gly Ala Pro Val Pro Tyr Val Arg Pro Ala Ile
    610                 615                 620

Leu Glu Lys Gly Gln Gly Arg Ile Ile Leu Lys Ala Ser Arg His Ala
625                 630                 635                 640

Cys Val Glu Val Gln Asp Glu Ile Ala Phe Ile Pro Asn Asp Val Tyr
                645                 650                 655

Phe Glu Lys Asp Lys Gln Met Phe His Ile Ile Thr Gly Pro Asn Met
            660                 665                 670

Gly Gly Lys Ser Thr Tyr Ile Arg Gln Thr Gly Val Ile Val Leu Met
        675                 680                 685

Ala Gln Ile Gly Cys Phe Val Pro Cys Glu Ser Ala Glu Val Ser Ile
    690                 695                 700

Val Asp Cys Ile Leu Ala Arg Val Gly Ala Gly Asp Ser Gln Leu Lys
705                 710                 715                 720

Gly Val Ser Thr Phe Met Ala Glu Met Leu Glu Thr Ala Ser Ile Leu
                725                 730                 735

Arg Ser Ala Thr Lys Asp Ser Leu Ile Ile Ile Asp Glu Leu Gly Arg
            740                 745                 750

Gly Thr Ser Thr Tyr Asp Gly Phe Gly Leu Ala Trp Ala Ile Ser Glu
        755                 760                 765

Tyr Ile Ala Thr Lys Ile Gly Ala Phe Cys Met Phe Ala Thr His Phe
    770                 775                 780

His Glu Leu Thr Ala Leu Ala Asn Gln Ile Pro Thr Val Asn Asn Leu
785                 790                 795                 800

His Val Thr Ala Leu Thr Thr Glu Glu Thr Leu Thr Met Leu Tyr Gln
                805                 810                 815

Val Lys Lys Gly Val Cys Asp Gln Ser Phe Gly Ile His Val Ala Glu
            820                 825                 830

Leu Ala Asn Phe Pro Lys His Val Ile Glu Cys Ala Lys Gln Lys Ala
        835                 840                 845

Leu Glu Leu Glu Glu Phe Gln Tyr Ile Gly Glu Ser Gln Gly Tyr Asp
    850                 855                 860

Ile Met Glu Pro Ala Ala Lys Lys Cys Tyr Leu Glu Arg Glu Gln Gly
865                 870                 875                 880

Glu Lys Ile Ile Gln Glu Phe Leu Ser Lys Val Lys Gln Met Pro Phe
                885                 890                 895

Thr Glu Met Ser Glu Glu Asn Ile Thr Ile Lys Leu Lys Gln Leu Lys
            900                 905                 910

Ala Glu Val Ile Ala Lys Asn Asn Ser Phe Val Asn Glu Ile Ile Ser
        915                 920                 925

Arg Ile Lys Val Thr Thr
    930
```

<210> SEQ ID NO 14
<211> LENGTH: 1360
<212> TYPE: PRT
<213> ORGANISM: Homo sapiens

<400> SEQUENCE: 14

```
Met Ser Arg Gln Ser Thr Leu Tyr Ser Phe Phe Pro Lys Ser Pro Ala
1               5                   10                  15

Leu Ser Asp Ala Asn Lys Ala Ser Ala Arg Ala Ser Arg Glu Gly Gly
            20                  25                  30
```

```
Arg Ala Ala Ala Ala Pro Gly Ala Ser Pro Ser Pro Gly Gly Asp Ala
        35                  40                  45

Ala Trp Ser Glu Ala Gly Pro Gly Pro Arg Pro Leu Ala Arg Ser Ala
    50                  55                  60

Ser Pro Pro Lys Ala Lys Asn Leu Asn Gly Gly Leu Arg Arg Ser Val
65                  70                  75                  80

Ala Pro Ala Ala Pro Thr Ser Cys Asp Phe Ser Pro Gly Asp Leu Val
                85                  90                  95

Trp Ala Lys Met Glu Gly Tyr Pro Trp Trp Pro Cys Leu Val Tyr Asn
            100                 105                 110

His Pro Phe Asp Gly Thr Phe Ile Arg Glu Lys Gly Lys Ser Val Arg
        115                 120                 125

Val His Val Gln Phe Phe Asp Asp Ser Pro Thr Arg Gly Trp Val Ser
    130                 135                 140

Lys Arg Leu Leu Lys Pro Tyr Thr Gly Ser Lys Ser Lys Glu Ala Gln
145                 150                 155                 160

Lys Gly Gly His Phe Tyr Ser Ala Lys Pro Glu Ile Leu Arg Ala Met
                165                 170                 175

Gln Arg Ala Asp Glu Ala Leu Asn Lys Asp Lys Ile Lys Arg Leu Glu
            180                 185                 190

Leu Ala Val Cys Asp Glu Pro Ser Glu Pro Glu Glu Glu Glu Glu Met
        195                 200                 205

Glu Val Gly Thr Thr Tyr Val Thr Asp Lys Ser Glu Glu Asp Asn Glu
    210                 215                 220

Ile Glu Ser Glu Glu Glu Val Gln Pro Lys Thr Gln Gly Ser Arg Arg
225                 230                 235                 240

Ser Ser Arg Gln Ile Lys Lys Arg Arg Val Ile Ser Asp Ser Glu Ser
                245                 250                 255

Asp Ile Gly Gly Ser Asp Val Glu Phe Lys Pro Asp Thr Lys Glu Glu
            260                 265                 270

Gly Ser Ser Asp Glu Ile Ser Ser Gly Val Gly Asp Ser Glu Ser Glu
        275                 280                 285

Gly Leu Asn Ser Pro Val Lys Val Ala Arg Lys Arg Lys Arg Met Val
    290                 295                 300

Thr Gly Asn Gly Ser Leu Lys Arg Lys Ser Ser Arg Lys Glu Thr Pro
305                 310                 315                 320

Ser Ala Thr Lys Gln Ala Thr Ser Ile Ser Ser Glu Thr Lys Asn Thr
                325                 330                 335

Leu Arg Ala Phe Ser Ala Pro Gln Asn Ser Glu Ser Gln Ala His Val
            340                 345                 350

Ser Gly Gly Gly Asp Asp Ser Ser Arg Pro Thr Val Trp Tyr His Glu
        355                 360                 365

Thr Leu Glu Trp Leu Lys Glu Glu Lys Arg Arg Asp Glu His Arg Arg
    370                 375                 380

Arg Pro Asp His Pro Asp Phe Asp Ala Ser Thr Leu Tyr Val Pro Glu
385                 390                 395                 400

Asp Phe Leu Asn Ser Cys Thr Pro Gly Met Arg Lys Trp Trp Gln Ile
                405                 410                 415

Lys Ser Gln Asn Phe Asp Leu Val Ile Cys Tyr Lys Val Gly Lys Phe
            420                 425                 430

Tyr Glu Leu Tyr His Met Asp Ala Leu Ile Gly Val Ser Glu Leu Gly
        435                 440                 445

Leu Val Phe Met Lys Gly Asn Trp Ala His Ser Gly Phe Pro Glu Ile
```

```
    450                 455                 460

Ala Phe Gly Arg Tyr Ser Asp Ser Leu Val Gln Lys Gly Tyr Lys Val
465                 470                 475                 480

Ala Arg Val Glu Gln Thr Glu Thr Pro Glu Met Met Glu Ala Arg Cys
                485                 490                 495

Arg Lys Met Ala His Ile Ser Lys Tyr Asp Arg Val Val Arg Arg Glu
            500                 505                 510

Ile Cys Arg Ile Ile Thr Lys Gly Thr Gln Thr Tyr Ser Val Leu Glu
        515                 520                 525

Gly Asp Pro Ser Glu Asn Tyr Ser Lys Tyr Leu Leu Ser Leu Lys Glu
    530                 535                 540

Lys Glu Glu Asp Ser Ser Gly His Thr Arg Ala Tyr Gly Val Cys Phe
545                 550                 555                 560

Val Asp Thr Ser Leu Gly Lys Phe Phe Ile Gly Gln Phe Ser Asp Asp
                565                 570                 575

Arg His Cys Ser Arg Phe Arg Thr Leu Val Ala His Tyr Pro Pro Val
            580                 585                 590

Gln Val Leu Phe Glu Lys Gly Asn Leu Ser Lys Glu Thr Lys Thr Ile
        595                 600                 605

Leu Lys Ser Ser Leu Ser Cys Ser Leu Gln Glu Gly Leu Ile Pro Gly
    610                 615                 620

Ser Gln Phe Trp Asp Ala Ser Lys Thr Leu Arg Thr Leu Leu Glu Glu
625                 630                 635                 640

Glu Tyr Phe Arg Glu Lys Leu Ser Asp Gly Ile Gly Val Met Leu Pro
                645                 650                 655

Gln Val Leu Lys Gly Met Thr Ser Glu Ser Asp Ser Ile Gly Leu Thr
            660                 665                 670

Pro Gly Glu Lys Ser Glu Leu Ala Leu Ser Ala Leu Gly Gly Cys Val
        675                 680                 685

Phe Tyr Leu Lys Lys Cys Leu Ile Asp Gln Glu Leu Leu Ser Met Ala
    690                 695                 700

Asn Phe Glu Glu Tyr Ile Pro Leu Asp Ser Asp Thr Val Ser Thr Thr
705                 710                 715                 720

Arg Ser Gly Ala Ile Phe Thr Lys Ala Tyr Gln Arg Met Val Leu Asp
                725                 730                 735

Ala Val Thr Leu Asn Asn Leu Glu Ile Phe Leu Asn Gly Thr Asn Gly
            740                 745                 750

Ser Thr Glu Gly Thr Leu Leu Glu Arg Val Asp Thr Cys His Thr Pro
        755                 760                 765

Phe Gly Lys Arg Leu Leu Lys Gln Trp Leu Cys Ala Pro Leu Cys Asn
    770                 775                 780

His Tyr Ala Ile Asn Asp Arg Leu Asp Ala Ile Glu Asp Leu Met Val
785                 790                 795                 800

Val Pro Asp Lys Ile Ser Glu Val Val Glu Leu Leu Lys Lys Leu Pro
                805                 810                 815

Asp Leu Glu Arg Leu Leu Ser Lys Ile His Asn Val Gly Ser Pro Leu
            820                 825                 830

Lys Ser Gln Asn His Pro Asp Ser Arg Ala Ile Met Tyr Glu Glu Thr
        835                 840                 845

Thr Tyr Ser Lys Lys Lys Ile Ile Asp Phe Leu Ser Ala Leu Glu Gly
    850                 855                 860

Phe Lys Val Met Cys Lys Ile Ile Gly Ile Met Glu Glu Val Ala Asp
865                 870                 875                 880
```

```
Gly Phe Lys Ser Lys Ile Leu Lys Gln Val Ile Ser Leu Gln Thr Lys
                885                 890                 895

Asn Pro Glu Gly Arg Phe Pro Asp Leu Thr Val Glu Leu Asn Arg Trp
            900                 905                 910

Asp Thr Ala Phe Asp His Glu Lys Ala Arg Lys Thr Gly Leu Ile Thr
        915                 920                 925

Pro Lys Ala Gly Phe Asp Ser Asp Tyr Asp Gln Ala Leu Ala Asp Ile
    930                 935                 940

Arg Glu Asn Glu Gln Ser Leu Leu Glu Tyr Leu Glu Lys Gln Arg Asn
945                 950                 955                 960

Arg Ile Gly Cys Arg Thr Ile Val Tyr Trp Gly Ile Gly Arg Asn Arg
                965                 970                 975

Tyr Gln Leu Glu Ile Pro Glu Asn Phe Thr Thr Arg Asn Leu Pro Glu
            980                 985                 990

Glu Tyr Glu Leu Lys Ser Thr Lys  Lys Gly Cys Lys Arg  Tyr Trp Thr
        995                 1000                1005

Lys Thr  Ile Glu Lys Lys Leu  Ala Asn Leu Ile Asn  Ala Glu Glu
    1010                 1015                 1020

Arg Arg  Asp Val Ser Leu Lys  Asp Cys Met Arg Arg  Leu Phe Tyr
    1025                 1030                 1035

Asn Phe  Asp Lys Asn Tyr Lys  Asp Trp Gln Ser Ala  Val Glu Cys
    1040                 1045                 1050

Ile Ala  Val Leu Asp Val Leu  Leu Cys Leu Ala Asn  Tyr Ser Arg
    1055                 1060                 1065

Gly Gly  Asp Gly Pro Met Cys  Arg Pro Val Ile Leu  Leu Pro Glu
    1070                 1075                 1080

Asp Thr  Pro Pro Phe Leu Glu  Leu Lys Gly Ser Arg  His Pro Cys
    1085                 1090                 1095

Ile Thr  Lys Thr Phe Phe Gly  Asp Asp Phe Ile Pro  Asn Asp Ile
    1100                 1105                 1110

Leu Ile  Gly Cys Glu Glu Glu  Glu Gln Glu Asn Gly  Lys Ala Tyr
    1115                 1120                 1125

Cys Val  Leu Val Thr Gly Pro  Asn Met Gly Gly Lys  Ser Thr Leu
    1130                 1135                 1140

Met Arg  Gln Ala Gly Leu Leu  Ala Val Met Ala Gln  Met Gly Cys
    1145                 1150                 1155

Tyr Val  Pro Ala Glu Val Cys  Arg Leu Thr Pro Ile  Asp Arg Val
    1160                 1165                 1170

Phe Thr  Arg Leu Gly Ala Ser  Asp Arg Ile Met Ser  Gly Glu Ser
    1175                 1180                 1185

Thr Phe  Phe Val Glu Leu Ser  Glu Thr Ala Ser Ile  Leu Met His
    1190                 1195                 1200

Ala Thr  Ala His Ser Leu Val  Leu Val Asp Glu Leu  Gly Arg Gly
    1205                 1210                 1215

Thr Ala  Thr Phe Asp Gly Thr  Ala Ile Ala Asn Ala  Val Val Lys
    1220                 1225                 1230

Glu Leu  Ala Glu Thr Ile Lys  Cys Arg Thr Leu Phe  Ser Thr His
    1235                 1240                 1245

Tyr His  Ser Leu Val Glu Asp  Tyr Ser Gln Asn Val  Ala Val Arg
    1250                 1255                 1260

Leu Gly  His Met Ala Cys Met  Val Glu Asn Glu Cys  Glu Asp Pro
    1265                 1270                 1275
```

-continued

```
Ser Gln Glu Thr Ile Thr Phe Leu Tyr Lys Phe Ile Lys Gly Ala
    1280                1285                1290

Cys Pro Lys Ser Tyr Gly Phe Asn Ala Ala Arg Leu Ala Asn Leu
    1295                1300                1305

Pro Glu Glu Val Ile Gln Lys Gly His Arg Lys Ala Arg Glu Phe
    1310                1315                1320

Glu Lys Met Asn Gln Ser Leu Arg Leu Phe Arg Glu Val Cys Leu
    1325                1330                1335

Ala Ser Glu Arg Ser Thr Val Asp Ala Glu Ala Val His Lys Leu
    1340                1345                1350

Leu Thr Leu Ile Lys Glu Leu
    1355                1360
```